US012781243B2

(12) United States Patent
Shang et al.

(10) Patent No.: US 12,781,243 B2
(45) Date of Patent: Nov. 3, 2026

(54) MODIFIED IMMUNE EFFECTOR CELL AND PREPARATION METHOD THEREFOR

(71) Applicant: NINGBO T-MAXIMUM BIOPHARMACEUTICALS CO., LTD., Ningbo (CN)

(72) Inventors: Xiaoyun Shang, Suzhou (CN); Haijuan Jiang, Suzhou (CN); Dan Wang, Suzhou (CN); Hui Shen, Suzhou (CN); Li Ma, Suzhou (CN); Yu Xin, Suzhou (CN); Fanli Xu, Suzhou (CN); Jialu Li, Suzhou (CN); Shaowen Ma, Suzhou (CN); Dan Zhao, Suzhou (CN)

(73) Assignee: NINGBO T-MAXIMUM BIOPHARMACEUTICALS CO., LTD., Ningbo (CN)

( * ) Notice: Subject to any disclaimer, the term of this patent is extended or adjusted under 35 U.S.C. 154(b) by 1332 days.

(21) Appl. No.: 17/563,804

(22) Filed: Dec. 28, 2021

(65) Prior Publication Data

US 2022/0193135 A1 Jun. 23, 2022

Related U.S. Application Data

(63) Continuation of application No. PCT/CN2020/140799, filed on Dec. 29, 2020.

(30) Foreign Application Priority Data

Jan. 2, 2020 (CN) ......................... 202010002929.3

(51) Int. Cl.

*C12N 15/00* (2006.01)
*A61K 40/11* (2025.01)

(Continued)

(52) U.S. Cl.

CPC .............. *C12N 15/85* (2013.01); *A61K 40/11* (2025.01); *A61K 40/31* (2025.01);

(Continued)

(58) Field of Classification Search

None

See application file for complete search history.

(56) References Cited

U.S. PATENT DOCUMENTS

| | | | |
|---|---|---|---|
| 10,391,126 | B2 | 8/2019 | Cooper et al. |
| 10,729,725 | B2 | 8/2020 | Terrett et al. |

(Continued)

FOREIGN PATENT DOCUMENTS

| | | |
|---|---|---|
| CN | 107206024 A | 9/2017 |
| CN | 107630006 A | 1/2018 |

(Continued)

OTHER PUBLICATIONS

WIPO English translation of WO-2019052577 (Year: 2020).*

(Continued)

*Primary Examiner* — M Franco G Salvoza

(74) *Attorney, Agent, or Firm* — Merchant & Gould P.C.; Daniel J. Pereira

(57) ABSTRACT

Provided is a modified immune effector cell, wherein compared with the expression and/or activity of the corresponding gene in a corresponding unmodified cell, the expression and/or activity of the TRAC gene and the HLA-A gene are down-regulated, the expression and/or activity of the B2M gene is not down-regulated, and the expression and/or activity of the CIITA gene is not down-regulated. Also provided is a method for preparing the modified immune effector cell.

18 Claims, 19 Drawing Sheets

Specification includes a Sequence Listing.

SEQ ID NO:97

SEQ ID NO:98

(51) Int. Cl.

| | |
|---|---|
| ***A61K 40/31*** | (2025.01) |
| ***A61K 40/42*** | (2025.01) |
| ***A61P 35/02*** | (2006.01) |
| ***C07K 14/435*** | (2006.01) |
| ***C12N 5/0783*** | (2010.01) |
| ***C12N 9/14*** | (2006.01) |
| ***C12N 15/85*** | (2006.01) |
| ***C12N 15/87*** | (2006.01) |
| *A61K 40/50* | (2025.01) |

(52) U.S. Cl.

CPC ...... *A61K 40/4211* (2025.01); *A61K 40/4215* (2025.01); *A61K 40/4221* (2025.01); *A61P 35/02* (2018.01); *C07K 14/435* (2013.01); *C12N 5/0636* (2013.01); *C12N 9/14* (2013.01); *C12N 15/87* (2013.01); *A61K 40/50* (2025.01)

(56) References Cited

U.S. PATENT DOCUMENTS

| | | | | |
|---|---|---|---|---|
| 10,736,919 | B2 | 8/2020 | Terrett et al. | |
| 10,857,184 | B2 | 12/2020 | Terrett et al. | |
| 2014/0349402 | A1 | 11/2014 | Cooper et al. | |
| 2018/0325955 | A1 | 11/2018 | Terrett et al. | |
| 2018/0362926 | A1 * | 12/2018 | Conway | A61K 40/11 |
| 2019/0314413 | A1 | 10/2019 | Terrett et al. | |
| 2019/0314414 | A1 | 10/2019 | Terrett et al. | |
| 2019/0365808 | A1 | 12/2019 | Terrett et al. | |
| 2019/0365809 | A1 | 12/2019 | Terrett et al. | |
| 2019/0388472 | A1 | 12/2019 | Cooper et al. | |
| 2020/0330518 | A1 | 10/2020 | Terrett et al. | |

FOREIGN PATENT DOCUMENTS

| | | | | |
|---|---|---|---|---|
| CN | 107723275 | A | 2/2018 | |
| CN | 109456942 | A | 3/2019 | |
| CN | 109456943 | A | 3/2019 | |
| CN | 109750035 | A | 5/2019 | |
| WO | 2013074916 | A1 | 5/2013 | |
| WO | WO-2015095410 | A1 * | 6/2015 | A61P 35/00 |
| WO | WO-2015161276 | A2 * | 10/2015 | C12N 15/113 |
| WO | WO 2017/093969 | A1 | 6/2017 | |
| WO | WO-2017193107 | A2 * | 11/2017 | A61P 35/00 |
| WO | 2019047899 | A1 | 3/2019 | |
| WO | WO-2019052577 | A1 * | 3/2019 | A61K 48/005 |
| WO | WO 2019/097305 | A2 | 5/2019 | |
| WO | WO-2019160077 | A1 * | 8/2019 | G01N 33/56977 |

OTHER PUBLICATIONS

WIPO English translation of WO2019160077 (Year: 2019).*

Office Action issued Mar. 22, 2024, in corresponding Australian Patent Application No. 2020418199.

Zhao, J. et al., "Universal CARs, universal T cells, and universal CAR T cells", *Journal of Hematology & Oncology* (2018) 11:132, 9 pages.

European Search Report dated Apr. 17, 2024 for EP Application No. 20911252.3 (10 pages).

International Search Report issued Mar. 29, 2021 in PCT/CN2020/140799, filed on Dec. 29, 2020, 5 pages.

Canadian Office Action issued Aug. 16, 2023 in Canadian Patent Application No. 3,163,304, 7 pages.

* cited by examiner

Negative control group

WT control group

Group in which the TRAC gene is knockout

MODIFIED IMMUNE EFFECTOR CELL AND PREPARATION METHOD THEREFOR

This application is a continuation of PCT/CN2020/140799, filed Dec. 29, 2020, which claims the benefit of CN application 202010002929.3 (CN), filed Jan. 2, 2020, the contents of both are incorporated herein by reference.

TECHNICAL FIELD

The present application relates to the biomedical field, in particular to a modified immunologic effector cell and a preparation method thereof.

SEQUENCE LISTING

In accordance with 37 CFR § 1.833-1835 and 37 CFR§ 1.77(b)(5), the specification makes reference to a Sequence Listing submitted electronically as a .xml file named "20250916_01310PA-013US_updated_suquence_listing.xml". The .xml file was generated on Sep. 16, 2025 and is 200,000 bytes in size. The entire contents of the Sequence Listing are hereby incorporated by reference.

BACKGROUND

Anti-tumor immunotherapies can cause long-term and strong response in a variety of malignant tumors, can be used to treat many different types of cancers, and exhibit a broad potential. Currently, anti-tumor immunotherapies mainly include two types of immunotherapies: immunocyte targeted monoclonal antibody (mAb) therapy and adoptive cell therapy (ACT). Of those, ACT refers to a therapy relying on returning autologous or allogeneic lymphocytes which are stimulated and amplified in vitro back into the human body so as to achieve an anti-tumor effect, but such a therapy only produces a relatively good effect in patients with MHC polymorphism consistency. The CAR-T is anew and effective MHC-independent adoptive cell therapy. CAR, also known as chimeric antigen receptor, is an artificial receptor that mimics the function of TCR. It can specifically recognize an antigen on the surface of tumor cells, so as to target and kill the tumor cells. However, timely and successful production and infusion of autologous CAR T cells is the biggest obstacle to implement an effective CAR T cell therapy. For example, if patients were previously treated with a chemotherapy regimen, the chemotherapy drugs can result in difficult expansion or decreased function of the T cells of the patients in vitro, resulting in insufficient or poor-quality CAR-T cell products. Moreover, autologous CAR-T is commonly used in ALL or CLL patients at present, and its application in solid tumor patients is facing great challenges. For example, the heterogeneity of tumor antigen limits the application of autologous CAR-T. In order to increase the flexibility of CAR and broaden the scope of antigen recognition, universal CAR-T emerges. The main design principle of universal CAR-T cells is to produce tumor antigen-specific T cells from allogeneic healthy donors. The so-obtained CAR-T cells exhibit increased amplification efficiency and activity. However, the endogenous TCR of allogeneic T cells can recognize the allogeneic antigen of receptor, which will lead to a graft-versus-host disease (GVHD). At the same time, the expression of HLA on the surface of allogeneic T cells will lead to a rapid rejection of host immune system (HVGR). Therefore, the problem of immune rejection response caused by allogeneic cell therapy needs to be further addressed.

SUMMARY OF THE INVENTION

The present application provides a modified immunologic effector cell, wherein the expression and/or activity of a TRAC gene and a HLA-A gene are/is down-regulated, the expression and/or activity of a B2M gene are/is not down-regulated, and the expression and/or activity of a CIITA gene are/is not down-regulated, as compared with the expression and/or activity of the corresponding gene in the corresponding cell which is not modified.

In some embodiments, the modification results in down-regulation of expression and/or activity of two genes, wherein the two genes consist of the TRAC gene and the HLA-A gene.

In some embodiments, the expression and/or activity of the TRAC gene and the HLA-A gene are/is down-regulated, the expression and/or activity of the B2M gene are/is not down-regulated, and the expression and/or activity of the CIITA gene are/is not down-regulated, as compared with the corresponding wild type cell.

In some embodiments, as compared with the corresponding wild type cell, the expression and/or activity of the two genes are/is down-regulated, wherein the two genes consist of the TRAC gene and the HLA-A gene.

In some embodiments, the immunologic effector cell includes T cell.

In some embodiments, the down-regulation of the expression level and/or activity of the genes includes a down-regulation of expression and/or activity of a nucleic acid molecule encoding the genes; and/or a down-regulation of expression and/or activity of a protein product encoded by the genes.

In some embodiments, the modification includes gene mutation and/or gene silencing.

In some embodiments, the modification includes administering one or more substances selected from the group consisting of antisense RNA, siRNA, shRNA, and CRISPR/Cas9 system to the immunologic effector cell.

In some embodiments, the modification includes administering CRISPR/Cas9 system to the immunologic effector cell.

In some embodiments, the allele of the HLA-A gene is selected from the group consisting of A*02, A*11, A*24, A*30, A*33, A*03, A*01 and A*26.

In some embodiments, the expression level and/or activity of at most 2 alleles of the HLA-A gene are/is down-regulated.

In some embodiments, the expression level and/or activity of 1 allele of the HLA-A gene are/is down-regulated.

In some embodiments, the modification includes administering an sgRNA targeting an exon of the HLA-A gene to the immunologic effector cell.

In some embodiments, the sgRNA targeting the exon of the HLA-A gene includes a nucleotide sequence shown in any one of SEQ ID No. 16-54 and 91-92.

In some embodiments, the modification further includes administering an sgRNA targeting an exon of the TRAC gene to the immunologic effector cell.

In some embodiments, the sgRNA targeting the exon of the TRAC gene includes a nucleotide sequence shown in any one of SEQ ID No. 1-15.

In some embodiments, the antisense RNA includes a nucleotide sequence as shown in any one of SEQ ID No. 93-96.

In some embodiments, the modification further includes administering Cas protein to the cell.

In some embodiments, the Cas protein includes a Cas9 protein.

In some embodiments, the immunologic effector cells include a nucleic acid encoding a chimeric antigen receptor (CAR), and the CAR includes an antigen binding domain, a hinge region, a transmembrane domain, a costimulatory structure, and a primary signal transduction domain.

In some embodiments, the antigen binding domain specifically binds to a tumor antigen.

In some embodiments, the tumor antigen is selected from the group consisting of: CD19, CD133, CD123, CD22, CD30, CD171, CA125, C-met, L1CAM, EC, DLL3, CD99, CS1, 5T4, CD138, CS-1 (also known as CD2 subclass 1, CRACC, SLAMF7, CD319 or 19A24), C-type lectin-like molecule-1 (CLL-1 or CLECL1), CD33, epidermal growth factor receptor variant III (EGFRvIII), ganglioside G2 (GD2), ganglioside GD3, TNF receptor family member B cell mature antigen (BCMA), Tn antigen (e.g., Tn Ag, GalNAca-Ser/Thr), prostate-specific membrane antigen (PSMA); receptor tyrosine kinase-like orphan receptor 1 (ROR1), Fms-like tyrosine kinase 3 (FLT3); tumor-associated glycoprotein 72 (TAG72), CD38, CD44v6, carcinoembryonic antigen (CEA), epithelial cell adhesion molecule (EPCAM), B7H3 (CD276), KIT (CD117), interleukin-13 receptor subunit α-2 (IL-13Ra2 or CD213A2), mesothelin, interleukin 11 receptor α (IL-11Ra), prostate stem cell antigen (PSCA), protease serine 21, vascular endothelial growth factor receptor 2 (VEGFR2), Lewis (Y) antigen, CD24, platelet-derived growth factor receptor β (PDGFR-β), stage-specific embryonic antigen-4 (SSEA-4), CD20, folate receptor α, receptor tyrosine-protein kinase ERBB2 (Her2/neu), cell surface-associated mucoprotein 1 (MUC1), epidermal growth factor receptor (EGFR), neurocyte adhesion molecule (NCAM), Prostase, prostate acid phosphatase (PAP), elongation factor 2 mutant (ELF2M), ephrin B2, fibroblast activated protein α (FAP), insulin-like growth factor 1 receptor (IGF-I receptor), carbonic anhydrase IX (CAIX), proteasome (e.g., proteasome, giantin factor) subunit B-type 9 (LMP2), glycoprotein 100 (gp100), oncogene fusion protein (bcr-abl) composed of breakpoint cluster region (BCR) and Abelson murine leukemia virus oncogene homolog 1 (Abl), tyrosinase, ephrin A-type receptor 2 (EphA2), fucosyl GM1; sialyl Lewis adhesion molecule (sLe), transglutaminase 5 (TGS5), high molecular weight-melanoma-associated antigen (HMWMAA), o-acetyl-GD2 ganglioside (OAcGD2), folate receptor β, tumor endothelial marker 1 (TEM1/CD248), tumor endothelial marker 7-associated (TEM7R), tight junction protein 6 (CLDN6), thyrotropin receptor (TSHR), G-protein-coupled receptor C-class Group 5 Member D (GPRC5D), chromosome X ORF 61 (CXORF61), CD97, CD179a, anaplastic lymphoma kinase (ALK), polysialic acid, placental specificity 1 (PLAC1), hexose moiety of globoH glycoceramide (GloboH), mammary gland differentiation antigen (NY-BR-1), uroplakin 2 (UPK2), hepatitis virus A cell receptor 1 (HAVCR1), adrenaline receptor 03 (ADRB3), pannexin 3 (PANX3), G-protein-coupled receptor 20 (GPR20), lymphocyte antigen 6 complex loci K9 (LY6K), olfactory receptor 51E2 (OR51E2), TCRγ variable ORF protein (TARP), Wilm tumor protein (WT1); cancer/testis antigen 1 (NY-ESO-1), cancer/testis antigen 2 (LAGE-1a), melanoma-associated antigen 1 (MAGE-A1), ETS translocation variant gene 6 located on chromosome 12p (ETV6-AML), sperm protein 17 (SPA17), X antigen family member 1A (XAGE1), angiogenin cell surface receptor 2 (Tie 2), melanoma cancer/testis antigen-1 (MAD-CT-1), melanoma cancer/testis antigen-2 (MAD-CT-2), Fos-associated antigen 1, p53, p53 mutant, prostate-specific protein (prostein), prostate cancer tumor antigen-1 (PCTA-1 or galectin 8), T cell-recognized melanoma antigen 1 (MelanA or MART1); rat sarcoma (Ras) mutant, human telomerase reverse transcriptase (hTERT), sarcoma translocation breakpoint, melanoma anti-apoptosis protein (ML-IAP), ERG (transmembrane protease, serine 2 (TMPRSS2) ETS fusion gene), N-acetylglucosaminyltransferase V (NA17), paired frame protein Pax-3 (PAX3), androgen receptor, cyclin B1, v-myc avian myelocytosis virus oncogene neuroblastoma-derived homologs (MYCN), Ras homolog family member C (RhoC), tyrosinase-associated protein 2 (TRP-2), cytochrome P450 1B1 (CYP1B1), T cell-recognized squamous cell cancer antigen 3 (SART3), paired frame protein Pax-5 (PAX5), proacrosomal protein binding protein sp32 (OY-TES1), lymphocyte-specific protein tyrosine kinase (LCK), A kinase anchorin 4 (AKAP-4), synovial sarcoma X breakpoint 2 (SSX2), receptor of advanced glycation end products (RAGE-1), legumain, human papilloma virus E6 (HPV E6), human papilloma virus E7 (HPV E7), intestinal carboxylesterase, mutated heat shock protein 70-2 (mut hsp70-2), CD79a, CD79b, CD72, leukocyte-associated immunoglobulin-like receptor 1 (LAIR1), Fc fragment of IgA receptor (FCAR or CD890), leukocyte immunoglobin-like receptor superfamily A member 2 (LILRA2), CD300 molecule-like family member f (CD300LF), C-type lectin domain family 12 member A (CLEC12A), bone marrow stromal cell antigen 2 (BST2), EGF-like modulus-containing mucoprotein-like hormone receptor-like 2 (EMR2), lymphocyte antigen 75 (LY75), glypican-3 (GPC3), Fc receptor-like 5 (FCRL5) and/or immunoglobulin λ-like peptide 1.

In some embodiments, the antigen binding domain is selected from the group consisting of a monoclonal antibody, a polyclonal antibody, a human antibody, a humanized antibody, a single domain antibody, and an antigen binding fragment.

In some embodiments, the antigen binding domain targets a solid tumor.

In some embodiments, the solid tumor is selected from the group consisting of: lung cancer, breast cancer, colon cancer, renal cell carcinoma, liver cancer, non-small cell lung cancer, small intestine cancer, esophagus cancer, osteosarcoma, pancreatic cancer, skin cancer, head or neck cancer, cutaneous or intraocular malignant melanoma, uterus cancer, ovarian cancer, rectal cancer, anal cancer, stomach cancer, testis cancer, fallopian tube carcinoma, endometrial cancer, cervical cancer, vaginal cancer, vulval cancer, Hodgkin's disease, non-Hodgkin's lymphoma, carcinoma of endocrine system, thyroid cancer, parathyroid cancer, adrenal carcinoma, soft tissue sarcoma, urethral carcinoma, carcinoma of penis, pediatric solid tumor, bladder cancer, renal or ureteral cancer, carcinoma of renal pelvis, central nervous system (CNS) tumor, primary CNS lymphoma, tumor angiogenesis, spinal tumor, brainstem glioma, pituitary adenoma, Kaposi sarcoma, epidermoid, squamous cell carcinoma, and T cell lymphoma.

In some embodiments, the antigen binding domain targets a non-solid tumor.

In some embodiments, the non-solid tumor is selected from the group consisting of chronic lymphoblastic leukemia (CLL), acute leukemia, acute lymphoblastic leukemia (ALL), B cell acute lymphoblastic leukemia (B-ALL), T cell acute lymphoblastic leukemia (T-ALL), chronic myeloid leukemia (CML), acute myeloid leukemia (AML), B cell prolymphocytic leukemia, blast cell plasmacytoid dendritic cytoma, Burkitt's lymphoma, diffuse large B cell lymphoma, follicular lymphoma, hairy cell leukemia, small or large cell follicular lymphoma, malignant lymphoproliferative conditions, MALT lymphoma, mantle cell lymphoma, marginal zone lymphoma, multiple myeloma, myelodysplasia and myelodysplastic syndrome, Hodgkin's lymphoma, plasmablast lymphoma, Plasmacytoid dendritic cytoma, B lymphocytoma, and Waldenstrom macroglobulinemia.

In some embodiments, the transmembrane domain includes one protein derived from a protein selected from the group consisting of CD28, CD3e, CD27, CD3c, CD45, CD4, CD5, CD8, CD9, CD16, CD22, CD33, CD37, CD64, CD80, CD86, CD134, CD137, CD154, CD19, IL2RP, IL2Rγ, IL7Rα, ITGAD, CD11d, ITGAE, CD103, ITGAL, CD11a, LFA-1, ITGAM, CDTTb, ITGAX, CDTTc, ITGB1, CD29, ITGB2, CD18, LFA-1, ITGB7, TNFR2.

In some embodiments, the costimulatory domain includes a costimulatory domain of protein selected from the group consisting of: CD137, CD28, CD27, OX40, CD30, CD40, PD-1, ICOS, LFA-1, CD2, CD7, CD160(BY55), LIGHT, NKG2C, B7-H3, CDS, ICAM-1, GITR, BAFFR, HVEM (LIGHTR), SLAMF7, NKp80(KLRF1), CD19, CD4, CD8u, CD80, IL2RP, IL2Rγ, IL7 Rα, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, ITGB7, TNFR2, TRANCE/RANKL, DNAM1(CD226), SLAMF4(CD244, 2B4), CD84, CD96(Tactile), CEACAM1, CRTAM, Ly9(CD229), CD160, PSGL1, CD100(SEMA4D), CD69, SLAMF6(NTB-A, Ly108), SLAM(SLAMF1, CD150, IPO-3), BLAME(SLAMF8), SELPLG(CD162), LTBR, LAT, GADS, SLP-76, PAG/Cbp, NKp44, NKp30, NKp46 and/or NKG2D.

In some embodiments, the primary intracellular signal transduction domain includes a functional signal transduction domain of protein selected from the group consisting of CD3ζ, FcRγ(FCER1G), FcγRIIa, FcRβ(FcεR1b), CD3γ, CD3δ, CD3ε, CD79a, CD79b, DAP10 and/or DAP12.

In some embodiments, the hinge region connects the antigen binding domain with the transmembrane domain, and includes a hinge region of protein selected from the group consisting of human Ig (immunoglobulin) hinge region, a GS linker, a KIR2DS2 hinge region, or a CD8a hinge region.

The present application further provides a method of preparing the modified immunologic effector cell of the present application, including the following steps: as compared with the expression and/or activity of the corresponding genes in corresponding cells which are not modified, down-regulating the expression and/or activity of the TRAC gene and the HLA-A gene in the immunologic effector cell, not down-regulating the expression and/or activity of the B2M gene, and not down-regulating the expression and/or activity of the CIITA gene.

In some embodiments, the modification results in down-regulation of expression and/or activity of two genes, wherein the two genes consist of the TRAC gene and the HLA-A gene.

In some embodiments, the expression and/or activity of the TRAC gene and the HLA-A gene are/is down-regulated, the expression and/or activity of the B2M gene are/is not down-regulated, and the expression and/or activity of the CIITA gene are/is not down-regulated, as compared with the corresponding wild type cell.

In some embodiments, as compared with the corresponding wild type cell, the expression and/or activity of the two genes are down-regulated, wherein the two genes consist of the TRAC gene and the HLA-A gene.

In some embodiments, the down-regulation of the expression level and/or activity of the genes include a down-regulation of expression and/or activity of a nucleic acid molecule encoding the genes; and/or a down-regulation of expression and/or activity of a protein product encoded by the genes.

In some embodiments, the modification includes gene mutation and/or gene silencing.

In some embodiments, the modification includes administering one or more substances selected from the group consisting of: antisense RNA, siRNA, shRNA, and CRISPR/Cas9 system to the immunologic effector cell.

In some embodiments, the modification includes administering CRISPR/Cas9 system to the immunologic effector cell.

In some embodiments, the modification includes administering an sgRNA targeting an exon of the HLA-A gene to the immunologic effector cell.

In some embodiments, the sgRNA targeting the exon of the HLA-A gene includes a nucleotide sequence shown in any one of SEQ ID No. 16-54 and 91-92.

In some embodiments, the modification includes administering an sgRNA targeting an exon of the TRAC gene to the immunologic effector cell.

In some embodiments, the sgRNA targeting the exon of the TRAC gene includes a nucleotide sequence shown in any one of SEQ ID No. 1-15.

In some embodiments, the antisense RNA includes a nucleotide sequence as shown in any one of SEQ ID No. 93-96.

In some embodiments, the modification further includes administering Cas protein to the cell.

In some embodiments, the Cas protein includes Cas9 protein.

The present application further provides a composition including the immunologic effector cells of the present application and a pharmaceutically acceptable carrier.

In some embodiments, the composition includes a cell population, wherein the cell population includes the modified immunologic effector cell of the present application.

The present application further provides use of the modified immunologic effector cells of the present application for preparing a CAR-T cell.

The present application further provides use of the modified immunologic effector cells of the present application in manufacture of a drug for allogeneic therapy.

The present application further provides a method of allogeneic therapy, including administering the modified immunologic effector cell of the present application to a patient or subject.

The present application further provides use of the modified immunologic effector cell of the present application for allogeneic therapy.

The present application further provides use of the modified immunologic effector cell of the present application in manufacture of a drug for treating tumors.

The present application further provides a method of treating tumor, including administering the modified immunologic effector cell of the present application to a patient or subject.

The present application further provides the modified immunologic effector cell for treating a tumor.

In some embodiments, the tumor includes solid and non-solid tumors.

In some embodiments, the tumor is selected from the group consisting of lung cancer, breast cancer, colon cancer, renal cell carcinoma, liver cancer, non-small cell lung cancer, small intestine cancer, esophagus cancer, osteosarcoma, pancreatic cancer, skin cancer, head or neck cancer, cutaneous or intraocular malignant melanoma, uterus cancer, ovarian cancer, rectal cancer, anal cancer, stomach cancer, testis cancer, fallopian tube carcinoma, endometrial cancer, cervical cancer, vaginal cancer, vulval cancer, Hodgkin's disease, non-Hodgkin's lymphoma, carcinoma of endocrine system, thyroid cancer, parathyroid cancer, adrenal carcinoma, soft tissue sarcoma, urethral carcinoma, carcinoma of penis, pediatric solid tumor, bladder cancer, renal or ureteral cancer, carcinoma of renal pelvis, central nervous system (CNS) tumor, primary CNS lymphoma, tumor angiogenesis, spinal tumor, brainstem glioma, pituitary adenoma, Kaposi sarcoma, epidermoid, squamous cell carcinoma, and T cell lymphoma.

Persons skilled in the art can easily recognize other aspects and advantages of the present application from the following detailed description.

The following detailed description only shows and describes exemplary embodiments of the present application. As persons skilled in the art will appreciate, the present application enables persons skilled in the art to make modifications to the disclosed embodiments without departing the spirit and scope of the invention involved in the present application. Correspondingly, the accompany drawings and description in the specification of the present application are only illustrative, rather than restrictive.

BRIEF DESCRIPTION OF THE DRAWINGS

The specific features of the invention involved in the present application are shown in the appended claims. By referring to the exemplary embodiments as detailedly described below and the accompanying drawings, the features and advantages of the invention involved in the present application can be better understood. The accompany drawings are briefly described as follows:

DETAILED DESCRIPTION OF THE EMBODIMENTS

Figure 1:
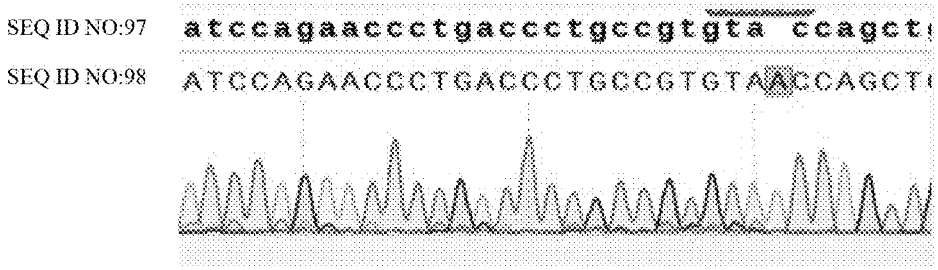
FIG. 1 shows the Sanger sequencing results of the TRAC gene of the present application after Sg9RNA editing.

Hereinafter the embodiments of the present application are described by reference to particular examples. Persons skilled in the art can readily understand other advantages and effects of the inventions of the present application from the disclosure of the present specification.

Hereinafter the present application will be further described. In the present invention, unless otherwise specified, the scientific and technical terms as used herein will have meanings commonly understood by persons skilled in the art. Moreover, all the terms and laboratory operation steps associated with protein and nucleic acid chemistry, molecular biology, cell and tissue culture, microbiology and immunology used herein are widely used terms and conventional steps in the corresponding fields. Meanwhile, in order to better understand the present invention, definitions and explanations of related terms are provided below.

In the present application, the term "immune effector cells" generally refers to immune cells that take part in the immune response and perform the effector function. For example, the performing effector function can include clearing a foreign antigen or promoting a response of immune effector, etc. Immune effector cells can include plasmacytes, T cells, B cells, natural killer (NK) cells, natural killer T (NKT) cells, mastocytes, and bone marrow-derived phagocytes.

In the present application, the term "modification/modified" generally refers to changing cell status or structure and/or change of cell status or structure. The change is usually in relation to the status or structure of the corresponding cells that are not modified. The change can include changes in the expression level or function of endogenous cell genes, e.g., down-regulating, up-regulating the expression level of endogenous cell genes or not expressing the endogenous cell genes by means of genetic engineering. The genetic engineering means can include homologous recombination, CRISPR/Cas9 system gene editing, etc. The change can also include changes in cell protein expression, structure or function, e.g., changes in protein expression, structure or function realized by changing the expression level or function of corresponding endogenous genes, such as, changes in protein expression, structure or function realized by regulating protein translation and post-translational modification. The changes can also include introduction of foreign gene, expression of foreign protein and so on.

In the present application, the term "TRAC" generally refers to T cell receptor α chain constant region (T cell receptor alpha constant). T cell receptor (TCR) generally refers to a specific receptor located on the surface of T cell that can recognize an antigen binding to a major histocompatibility complex (MHC) molecule. TCR is commonly composed of two different protein chains (i.e., a heterogeneous dimer). In humans, the TCR in a majority of T cells is composed of one alpha-chain and a beta-chain (which are encoded by TRA and TRB, respectively), and such T cells are called α,β-T cells. In a minority of T cells, the TCR is composed of γ-chain and δ-chain (which are encoded by TRG and TRD, respectively), and such T cells are called γ,δ-T cells. Generally, α,β-T cells account for about 95% of the total T cells, while γ,δ-T cells account for about 5% of the total T cells. This ratio varies during the development of individuals and in diseased states, such as leukemia, and varies between species. Each chain of TCR contains variable regions and constant regions. In humans, the gene encoding the α chain (TRA, e.g., information as shown by HGNC: 12027) is located on chromosome 14 and consists of multiple gene fragments, including a variable fragment (V), a junction fragment (J) and a constant region (C). The TRAC gene generally refers to a gene sequence encoding the constant region (C) of α chain of T cell receptor (e.g., information as shown by HGNC:12029), which is located on chromosome 14 (14q11.2; 14: 22,547,505-22,552,131). Generally, one of the genes of the variable fragments (V) encoding the N-fragment of antigen recognition domain is rearranged with one of the junction fragments (J) to produce a functional V-region exon, which is transcribed and linked to the constant region (C) by splicing, thereby forming a coding sequence of α chain of the T cell receptor.

In the present application, "HLA-A" generally refers to a class of polypeptide chains of human leukocyte antigens which are encoded by the HLA-A gene located at human chromosome 6p21.3 (e.g., information as shown by HGNC: 4931). HLA-A is one of the three major types of polypeptides that constitute MHC Class I molecules on the surface of human cells, and others further include HLA-B and HLA-C. A heterodimer composed of an α chain encoded by HLA-A gene and a β chain encoded by B2M gene (β2-microglobulin) is an HLA-A class MHC I molecule. The α chain encoded by HLA-A gene can include an α1 domain, an α2 domain, an α3 domain, a transmembrane region, and a cytoplasmic region, wherein the α1 domain, and the α2 domain can be combined with a peptide fragment so as to present the peptide fragment to the immune cells by the MHC I molecules (e.g., HLA-A class). In humans, similar to most mammals, the α chain of MHC I molecule is polymorphic, and there are many variations in the primary structure thereof. By December 2013, there are 2432 known HLA-A alleles in total, which encode 1740 active proteins and 117 inactive proteins. In the present application, HLA-A alleles can include sequence information of different HLA-A alleles included in the IMGT/HLA Database Version 3.38.0 (www.ebi.ac.uk/ipd/imgt/hla/) and named by the WHO HLA Factor Nomenclature Committee.

In the present application, the term "B2M" generally refers to 02-microglobulin that is one of the components of the MHC Class I molecule. 02 microglobulin (also known as 3 chain) can form an MHC Class I molecule, together with an α chain encoded by HLA. B2M is generally expressed in all karyocytes. In humans, 02 microglobulin is encoded by the B2M gene located at 15q21.1 (e.g., information as shown by HGNC:914).

In the present application, the term "CIITA" generally refers to a transactivator of major histocompatibility complex Class II (MHC II). The transactivator can be a protein including an acid transcription activation domain, four LRRs (a leucine-enriched repetitive sequence) and a GTP binding domain. The protein can be located within the cell nucleus as a positive modulator of gene transcription of the major histocompatibility complex Class II (MHCII), and called as "primary control factor" for the expression of these genes. The protein can also bind to GTP and transport itself to the nucleus by binding to GTP, where it usually functions by acetyltransferase (AT) activity in a coactivator-like manner. In humans, the protein is encoded by the gene located at 16p13.13 (e.g., information as shown by HGNC:7067), which can produce several isoform transcript variants encoding different isoforms.

In the present application, the term "wild-type cell" generally refers to naturally-occurring or naturally derived cells.

In the present application, the term "T cells" generally refers to thymus-derived cells that participate in immune responses mediated by various cells.

In the present application, the term "nucleic acid" or "polynucleotide" or "nucleic acid molecule" generally refers to deoxyribonucleic acid (DNA) or ribonucleic acid (RNA) and a polymer of single stranded or double stranded formats. Unless specifically defined, the term may include nucleic acids which include naturally-occurring nucleotide analogues that have similar binding properties to a reference nucleic acid (e.g., showing the sequence information) and are metabolized in a manner similar to naturally occurring nucleotides. Unless otherwise specified, the sequence of a nucleic acid can include conservatively modified variants thereof, such as, degenerate codon substitution, alleles, direct homologs, SNPs and complementary sequences, as well as explicitly specified sequences.

In the present application, the term "expression" generally refers to the transcription and/or translation of a specific nucleotide sequence.

In the present application, the term "gene mutation" generally refers to a variation in the composition or arrangement sequence of base pairs in the structure of a gene, e.g., point mutations caused by change of a single base, or deletion, duplication, insertion of a plurality of bases, etc.

In the present application, the term "gene silencing" generally refers to blocking the expression of certain genes through regulatory mechanisms. It includes primarily two types: one is transcriptional gene silencing (TGS) caused by factors like DNA methylation, heterochromatin, location effect, etc., and the other is post-transcriptional gene silencing (PTGS), i.e., affecting the expression of gene at the post-transcriptional level by specific intervention of target RNA. Generally, when a gene is silenced, the expression of the corresponding gene is down-regulated/reduced. When a gene is knocked out, it is usually no expressed. For example, the expression of a certain gene disappears in cells if all alleles of a certain gene are knocked out. Gene silencing is usually considered as a mechanism of gene knockdown, and the general method for gene silencing can be, e.g., RNAi.

In the present application, the term "endogenous" refers to any substance derived from or generated within organisms, cells, tissues, or systems.

In the present application, the term "exogenous" refers to any substance introduced from or generated outside organisms, cells, tissues, or systems.

In the present application, the term "antisense RNA" generally refers to a single stranded RNA complementary to a transcript mRNA (messenger RNA). The antisense RNA can inhibit the expression of gene by binding to mRNA. For example, the binding of antisense RNA with target mRNA results in an increased sensitivity of the double stranded RNA molecule to RNA enzyme III, and causes the degradation of the double stranded RNA molecule. For example, the antisense RNA binds to the upstream untranslated region of mRNA, so as to directly inhibit the translation of target mRNA.

In the present application, the term "siRNA" generally refers to an abbreviation of Small Interfering RNA or Short Interfering RNA. SiRNA is a class of double stranded, noncoding RNA molecules with a length of about 18-28 base pairs, which can cause the degradation of mRNA by the complementary binding with mRNA, thereby interfering with the expression of specific genes. In some embodiments, siRNA can be a product obtained by treating a long double stranded RNA or shRNA with Dicer enzyme. In some embodiments, siRNA enters a cell and forms an RNA induced silencing complex (RISC) with another protein, the sense strand is degraded, and the antisense strand binds to a complementary target sequence, thereby achieving gene silencing.

In the present application, the term "shRNA" generally refers to an abbreviation of short hairpin RNA, that is, "short hairpin RNA". ShRNA usually includes two short reverse repeat sequences spaced by a loop sequence to form a hairpin structure. Generally, it can further include 5-6 T bases as the transcription terminator of RNA polymerase III. In some embodiments, shRNA can enter cells via viral vectors or plasmids, and be transcribed under the action of polymerase II or polymerase III. The transcripts are exported from the nucleus (usually through Exportin 5), and then transported to RISC after Dicer treatment. The sense strand is degraded, and the antisense strand can be combined with a complementary target sequence, thereby achieving gene silencing.

In the present application, the term "CRISPR/Cas system" generally refers to a group of molecules including RNA-directed nuclease or other effector molecules and gRNA molecules, which can direct and realize the modification of nucleic acid at the site of targeting sequence by RNA-directed nuclease or other effector molecules, e.g., inducing degradation of the target sequence. In some embodiments, the CRISPR system includes gRNA and a Cas protein, e.g., a Cas9 protein. The system including Cas9 or a functional variant thereof is called "Cas9 system" or "CRISPR/Cas9 system" in the present application. In some embodiments, the gRNA molecule can be complexed with the Cas molecule to form a ribonucleoprotein (RNP) complex.

In the present application, the terms "gRNA molecule" or "guide RNA", "instruction RNA", "direct RNA", "guide RNA molecule", "gRNA" can be used interchangeably, and generally refer to a nucleic acid molecule that can promote directing the RNA-directed nuclease or other effector molecules (generally combined with gRNA molecules) specifically to the target sequence. In some embodiments, the directing is achieved by the hybridization of a portion of gRNA with DNA (e.g., via a gRNA guide domain) and the binding of a portion of gRNA molecule with an RNA directed nuclease or other effector molecules (e.g., at least through gRNAtracr). In some embodiments, the gRNA molecule consists of a single continuous polynucleotide molecule, which is herein referred to as a "single guide RNA" or "sgRNA" or the like. In other embodiments, the gRNA molecule consists of a plurality of (e.g., two) polynucleotide molecules that can be associated with themselves (generally by hybridization), which is herein referred to as "double guide RNA" or "dgRNA", etc.

In the present application, the term "Cas protein" generally refers to an enzyme responsible for cutting DNA in the CRISPR/Cas system. It can include enzymes from CRISPR/Cas system Types I, II, and III, e.g., Cas3, Cas9, Cas10.

In the present application, the term "Cas9 protein" generally refers to an enzyme from the bacterial type II CRISPR/Cas system and responsible for cutting DNA. Cas9 can include the wild-type protein and functional variants thereof.

In the present application, "allele" generally refers to various forms of variations in gene sequences on loci. Locus, also known as gene site or site, refers to a fixed position on a chromosome, such as the location of a gene. The arrangement of loci in a genome is called genetic map.

In the present application, the term "chimeric antigen receptor (CAR)" generally refers to an antigen receptor fused by fusing an antigen binding region of an antibody which recognizes a tumor associated antigen (TAA) or a binding fragment of other target molecules with an "immune receptor tyrosine-based activation motifs (ITAM, typically CD3ζ or FcεRIγ) of an intracellular signal domain. For example, the basic structure of CAR can include an antigen binding domain of a tumor-associated antigen (TAA) or other target molecules (typically, an scFv originated from the antigen binding region of a monoclonal antibody), an extracellular hinge region, a transmembrane region, and an immunoreceptor tyrosine-based activation motif (ITAM) of an intracellular immune receptor.

In the present application, the term "binding domain" generally refers to a domain that (specifically) binds to a given target epitope or a given target site of a target molecule (e.g., an antigen), interacts with the given target epitope or the given target site, or recognizes the given target epitope or the given target site.

In the present application, the term "specific binding" generally refers to a measurable and reproducible interaction, such as, the binding between a target and an antibody, which can determine the presence of a target in the presence of heterogeneous populations of molecules (including biomolecules). For example, antibodies that specifically bind to targets (which can be epitopes) are antibodies that bind the target(s) with greater compatibility, affinity, easiness, and/or duration than other targets. In some embodiments, the antibody specifically binds to an epitope on a protein that is conserved in proteins of different species. In another embodiment, the specific binding includes but is not limited to exclusive binding.

In the present application, the term "transmembrane domain" generally refers to a polypeptide or protein which is encoded at a DNA level by an exon including at least an extracellular region, a transmembrane region, and an intracellular region. The transmembrane domain generally includes three different structural regions: N-terminal extracellular region, middle conserved transmembrane extension region, and C-terminal cytoplasmic region. The transmembrane domain may further include an intracellular region or a cytoplasmic region.

In the present application, the term "hinge region" generally refers to a region located between the binding domain and the transmembrane domain in the CAR structure. The hinge region usually comes from IgG family, such as IgG1 and IgG4, and some from IgD and CD8. Generally, the hinge region has a certain degree of flexibility, which affects the spatial constraints between the CAR molecule and its specific target, thereby affecting the contact between CAR T cells and tumor cells.

In the present application, the term "costimulatory" generally refers to a source of the second signal of lymphocyte activation, which is usually generated by an interaction of costimulatory molecules on the surface of immune cells (between T cells/B cells or between antigen presenting cells/T cells) involved in adaptive immunity with their receptors. For example, the complete activation of T cells depends on dual signaling and the action of cytokine. The first signal of T cell activation is derived from the specific binding of its receptors with the antigens, that is, the recognition of T cells to the antigens; and the second signal of T cell activation is derived from the costimulatory molecule, that is, the interaction of the costimulatory molecules of the antigen presenting cells with the corresponding receptors on the surfaces of T cells.

In the present application, the term "costimulatory domain" generally refers to an intracellular portion of the corresponding receptor of the costimulatory molecule, which can transduce a costimulatory signal (also known as the second signal). For example, in CAR-T cells, the costimulatory domain derived from CD137 (or receptors of other costimulatory molecules) can be activated after the binding of the extracellular binding domain in the CAR structure with the corresponding antigen, thereby transducing a costimulatory signal.

In the present application, the term "primary signal transduction domain" generally refers to an amino acid sequence within a cell that can generate signals which promote the immune effector function of CAR-containing cells such as CAR-T cells. Examples of the immune effector functions in, e.g., CAR-T cells can include cell lysis activity and auxiliary activity, including cytokine secretion. In some embodiments, the primary signal transduction domain transduces the effector functional signals and directs the cells to perform the specialization function. Although the primary signal transduction domain can be used in its entirety, it is not necessary to use the entire chain in many cases. As for the use of a truncated portion of the primary signal transduction domain, such truncated portion can be used to replace the intact chain, as long as it can transduce the effector functional signals. The term "primary signal transduction domain" is thus intended to encompass any truncated portion of an intracellular signal transduction domain that is sufficient to transduce the effector functional signals.

In the present application, the term "tumor antigen" generally refers to a molecule that is expressed on the surface of a tumor cell in its entirety or as a fragment and can be used to preferentially direct a drug to the tumor cell (e.g., proteins, saccharides, or lipids). In some embodiments, the tumor antigen can be a marker expressed by both normal cells and cancer cells, e.g., genealogical markers, such as, CD19 on B cells. In some embodiments, the tumor antigen can be cell surface molecules with over-expression in tumor cells, e.g., 1-fold, 2-fold, 3-fold, or more over-expression, as compared with that in normal cells. In some embodiments, the cell surface molecules are abnormally expressed in tumor cells, e.g., including deletion, addition, or mutation of molecules as compared with the corresponding molecules expressed in normal cells. In some embodiments, the tumor antigen can be exclusively expressed on the surface of tumor cells in its entirety or as a fragment (e.g., MHC/peptide), and not synthesized or expressed on the surface of normal cells. In some embodiments, the CARs in the present application can include an antigen binding domain binding to the MHC-presenting peptide, such as, an antibody or a fragment of antibody. In general, endogenous protein-derived peptides bind to major histocompatibility complex (MHC) Class I molecules, and are recognized by the T cell receptors (TCR) on CD8+ T lymphocytes. MHC Class I complexes are constitutively expressed by all the karyocytes. Virus specific and/or tumor specific peptide/MHC complexes can be used as a unique class of cell surface targets for immunotherapy. (see, e.g., Sastry et al., J Virol. 2011 85(5):1935-1942; Sergeeva et al., Blood, 2011 117(16):4262-4272; Verma et al., J Immunol 2010 184(4):2156-2165; Willemsen et al., Gene Ther 2001 8(21):1601-1608; Dao et al., Sci Transl Med 2013 5(176):176ra33; Tassev et al., Cancer Gene Ther 2012 19(2):84-100).

In the present application, the term "monoclonal antibody" generally refers to antibodies obtained from a population of substantially homogeneous antibodies. Namely, all antibodies constituting the population are the same, except for potential natural mutation and/or post-translational modification (such as isomerization and amidation) that may be present in a very small amount. The monoclonal antibody is highly specific and targets a single antigenic site. Unlike typical polyclonal antibody preparations containing different antibodies targeting different determinants (epitopes), each type of monoclonal antibody targets a single determinant on the antigen. In addition to their specificity, the advantages of monoclonal antibodies rely on that they are synthesized from hybridoma cultures and are not contaminated by other immunoglobulins. The modifier "monoclonal" indicates that the antibody obtains characteristics from a population of substantially homogeneous antibodies, and should not be interpreted as requiring generating an antibody by any specific method.

In the present application, the term "polyclonal antibody" generally refers to a composition of various antibody molecules. The polyclonal antibodies can bind to or be reacted with a plurality of different specific antigen determinants on a single antigen or different antigens. The variation degree of antigenic specificity of the polyclonal antibodies is located within the variable regions of a single antibody constituting the polyclonal antibodies, such as, in the complementary determining region (CDR) 1, CDR2, and CDR3 regions. For example, the polyclonal antibodies can be prepared by immunizing animals with target sFGFR or a part thereof. For example, the polyclonal antibodies can be prepared by mixing multiple monoclonal antibodies with the desired target sFGFR specificity.

In the present application, the term "human antibody" generally refers to an antibody with variable and constant regions derived from the sequence of immunoglobulin of human germ line. Human antibodies are well known in the prior art (e.g., please refer to van Dijk, M. A. and van de Winkel, J. G., Curr. Opin. Chem. Biol. 5(2001)368-374). The human antibodies can also be generated in transgenic animals (e.g., mice) which can generate a complete or selected set of human antibodies in absence of generated endogenous immunoglobulin after immunization (e.g., Jakobovits, A. et al., Proc. Natl. Acad. Sci. USA 90(1993) 2551-2555; Jakobovits, A. et al., Nature 362(1993)255-258; Brueggemann, M. et al., Year Immunol. 7(1993)33-40). The human antibodies can also be generated in a phage display library (e.g., Hoogenboom, H. R. and Winter, G., J. Mol. Biol. 227(1992)381-388; Marks, J. D. et al., J. Mol. Biol. 222(1991)581-597). The term "human antibody" can also include antibodies modified in the constant regions.

In the present application, the term "humanized antibody" generally refers to an antibody which includes sequences of heavy chain variable regions and light chain variable regions derived from non-human species (e.g., mice), but in which at least a portion of the VH and/or VL sequences have been changed to be similar to the human germline variable sequences. For example, the term "humanized antibody" is an antibody or a variant, derivative, analogue or fragment thereof that can bind to a related antigen with immune specificity and includes a framework region (FR) which includes substantially an amino acid sequence of a human antibody and a complementary determining region (CDR) which includes substantially an amino acid sequence of a non-human antibody. In the context of CDR, the term "substantially" means that the amino acid sequence of CDR has at least 80%, e.g., at least 85%, at least 90%, at least 95%, at least 98% or at least 99% identity with an amino acid sequence of CDR of a non-human antibody. The humanized antibodies include substantially at least one, typically two variable domains (Fab, Fab', F(ab')2, FabC, Fv), wherein all or substantially all CDR regions correspond to the CDR region of a non-human immunoglobulin and all or substantially all framework regions are frame regions with consensus sequence of human immunoglobulin. In some embodiments, the humanized antibody can further include at least a portion of a constant region of immunoglobulin (Fc), typically a constant region of human immunoglobulin.

In the present application, the term "single domain antibody" generally refers to a class of antibodies in which a light chain of antibody is deleted and a heavy chain variable region is contained. It is also known as nanobody due to its low molecular weight. Single domain antibodies were initially found in camel family animals, and then similar antibodies were found in nurse shark, big star shark, skate and other cartilaginous fishes. For example, antibody in which the light chain and the CH1 region of the heavy chain constant region of a conventional antibody are deleted is called heavy chain antibody (HcAb), which are ubiquitous in all kinds of camel family. For example, a heavy chain antibody called as Ig new antigen receptor is abbreviated as IgNAR, which is composed of two identical heavy chains including five constant regions and one variable region. The variable regions of the heavy chain antibody are merely composed of the variable region of the heavy chain of the antibody. Like the Fab of a conventional antibody, the variable region can specifically bind to an antigen, so that the heavy antibody can play the same role as a conventional antibody.

In the present application, the term "tumor" generally refers to a neoplasm or solid lesion formed by abnormal cell growth. In the present application, the tumor can be a solid tumor or a non-solid tumor. In some embodiments, a visible lump that can be detected by clinical examinations such as, X-ray radiography, CT scanning, B-ultrasound or palpation can be called solid tumor, while a tumor that cannot be seen or touched by X-ray, CT scanning, B-ultrasound and palpation, such as leukemia, can be called non-solid tumor.

In the present application, the term "CD" (i.e., Cluster of differentiation), also called differentiation population, generally refers to cell surface molecules used to recognize immune antibody labels. CD molecules have many applications, typically as important receptors or ligands of cells. Some CDs can participate in the signal cascade of cells, thereby changing the behavior of cells. Some CDs are independent of cell signal transduction, but have other functions, such as cell adhesion. Until Apr. 21, 2016, the total number of human CD molecules is 371, such as, CD28, CD3e, CD45, CD4, CD5, CD8, CD9, CD16, CD22, CD33, CD37, CD64, CD80, CD86, CD134, CD137 and CD154 used as the source of transmembrane domain, and CD137, CD28, CD134 (OX-40) and CD278 (ICOS) as the source of costimulatory domain in the present application.

In the present application, the term "pharmaceutically acceptable carrier" generally refers to a pharmaceutically acceptable substance, composition, or vehicle involved in carrying, storing, transferring, or administering a cell preparation, e.g., liquids, semi-solid or solid fillers, diluents, osmotic agents, solvent, or encapsulating substances. The pharmaceutically acceptable carrier can include a pharmaceutically acceptable salt, wherein the term "pharmaceutically acceptable salt" includes salts of active compounds prepared by using a relatively nontoxic acid or base, e.g., sodium chloride, depending on the cell nature of the present application. The pharmaceutically acceptable carrier can further include organic acids (e.g., lactic acid), bioactive substances (e.g., polypeptides, antibodies, and the like) and antibiotics (e.g., penicillin, streptomycin), etc. The pharmaceutically acceptable carrier can further include a hydrogel, such as, a hydrogel containing polyacrylamide. The pharmaceutically acceptable carrier can include storage solution, cryopreservation solution, injection, etc., which can be used for cells. In general, the pharmaceutically acceptable carrier can maintain the activity of the cells carried by the carrier without hindering its therapeutic efficacy. The pharmaceutically acceptable carrier can also contribute to the storage, transportation, proliferation and migration of cells, and is suitable for clinical application.

In the present application, the term "composition" generally refers to a composition suitable for administration to patients, human patients. For example, the composition of the present application can include the immunologic effector cells of the present application, and optionally a pharmaceutical acceptable carrier. In some embodiments, the acceptable ingredients of the composition are nontoxic to the recipients at the dose and concentration as used. The composition of the present application includes, but is not limited to, liquid, frozen, and lyophilized compositions.

In the present application, the term "allogeneic therapy" generally refers to a therapy of administering organs, tissues, cells, etc. which do not come from the subject or patient to achieve a therapeutic purpose.

In the present application, the term "include/including" generally refers to encompassing clearly specified features, but does not exclude other elements.

In the present application, the term "about" generally refers to a variation within 0.5% to 10% of a given value, e.g., a variation within 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, or 10% of a given value.

In an aspect, the present application relates to a modified immunologic effector cell, wherein the expression and/or activity of the TRAC gene and the HLA-A gene are/is down-regulated, the expression and/or activity of the B2M gene are/is not down-regulated, and the expression and/or activity of the CIITA gene are/is not down-regulated, as compared with the expression and/or activity of the corresponding genes in corresponding cells which are not modified.

In another aspect, the present application further provides a method of preparing the modified immunologic effector cell of the present application, including the following steps: as compared with the expression and/or activity of the corresponding genes in corresponding cells which are not modified, down-regulating the expression and/or activity of the TRAC gene and the HLA-A gene in the immunologic effector cell, not down-regulating the expression and/or activity of the B2M gene, and not down-regulating the expression and/or activity of the CIITA gene.

In the present application, the modification results in down-regulation of expression and/or activity of two genes, wherein the two genes consist of the TRAC gene and the HLA-A gene.

Immune Effector Cells

In the present application, the immune effector cells can include plasmacytes, T cells, B cells, natural killer (NK) cells, natural killer T (NKT) cells, mastocytes, and/or bone marrow-derived phagocytes.

In the present application, the plasmacytes refer to effector B cells/antibody secreting cells, which can include proto-plasmacytes, proplasmacytes, Russell bodies, Dutcher bodies, flame-like cells, etc.

In the present application, the B cells refer to all types of B cells except plasmacytes, such as, pre-B cells, immature B cells, mature B cells, activated B cells, etc.

In the present application, the T cells can include: helper T cells (Th) that can assist in humoral immune and cellular immunity; suppressor T cells (Ts) that can suppress cellular immunity and humoral immunity; effector T cells (Te) that can release lymphokines; cytotoxic T cells (Tc) that can kill targets; delayed type hypersensitivity T cells (Td) that can participate in the action of Type IV allergy; amplifying T cells (Ta) that can act on Th and Ts to expand the immune effect; virgin or natural T cells that can differentiate into effector T cells or memory T cells upon exposure to an antigen; and memory T cells (Tm) that can remember specific antigen stimulations.

For example, the cytotoxic T cells can include a cell surface marker CD8+.

For example, the helper T cells can include a cell surface marker CD4+.

In the present application, the corresponding cells which are not modified can include wild-type cells and/or engineered cells. The wild-type cells can include naturally occurring cells or naturally derived cells, such as, plasmacytes, T cells, B cells, natural killer (NK) cells, natural killer T (NKT) cells, mastocytes and/or bone marrow-derived phagocytes which are isolated from human body, or immune effector cells which are differentiated by inducing precursor cells or pluripotent cells isolated from human body. The engineered cells can be plasmacytes, T cells, B cells, natural killer (NK) cells, natural killer T (NKT) cells, mastocytes and/or bone marrow-derived phagocytes which are isolated from human body or differentiated by inducing precursor cells or pluripotent cells isolated from human, and further engineered. For example, the human body is a healthy human body. For example, the healthy human body can include those without tumors or immune system-associated diseases or disorders.

In the present application, the artificial engineering can be those which do not target TRAC gene, HLA-A gene, B2M gene and the CIITA gene. For example, the artificial engineering does not affect the expression and/or activity of the TRAC gene, HLA-A gene, B2M gene and the CIITA gene. Said not affecting the expression and/or activity of TRAC gene, HLA-A gene, B2M gene and CIITA gene means that as compared with the corresponding cells which are isolated from human body, or corresponding cells which are differentiated by inducing precursor cells or pluripotent cells isolated from human body and are not further engineered, the expression and/or activity of the TRAC gene, HLA-A gene, B2M gene and the CIITA gene are not changed and not completely consistent. For instance, as measured by conventional technical means in the art, there is no significant difference (P>0.05) in the mRNA quantitative analysis of TRAC gene, HLA-A gene, B2M gene and the CIITA gene between the compared cells. By way of example, as measured by the conventional technical means in the art, there is no significant difference (P>0.05) in the corresponding polypeptide/protein quantitative analysis of TRAC gene, HLA-A gene, B2M gene and the CIITA gene between the compared cells. For example, the artificial engineered cells can include CAR-T cells. For example, the CAR-T cells can include those in which the CAR molecule includes a binding domain targeting a molecule selected from: CD19, PSCA, CD123, CD20, CEA, FAP, CD133, EGFR, EGFRVIII, BCMA, PSMA, Her2, CA125, EphA2, C-met, LiCAM, VEGFR, CS1, ROR1, EC, NY-ESO-1, MUC1, LewisY, GPC3, GD2, DLL3, CD99, 5T4, CD22, CD30, CD33, CD138 and/or CD171, CD19, CD133, CD123, CD22, CD30, CD171, CA125, C-met, LiCAM, EC, DLL3, CD99, CS1, 5T4, CD138, CS-1 (also known as CD2 subclass 1, CRACC, SLAMF7, CD319 or 19A24), C-type lectin-like molecule-1 (CLL-1 or CLECL1), CD33, epidermal growth factor receptor variant III (EGFRvIII), ganglioside G2 (GD2), ganglioside GD3, TNF receptor family member B cell mature antigen (BCMA), Tn antigen (e.g., Tn Ag, GalNAca-Ser/Thr), prostate-specific membrane antigen (PSMA); receptor tyrosine kinase-like orphan receptor 1 (ROR1), Fms-like tyrosine kinase 3 (FLT3); tumor-associated glycoprotein 72 (TAG72), CD38, CD44v6, carcinoembryonic antigen (CEA), epithelial cell adhesion molecule (EPCAM), B7H3 (CD276), KIT (CD117), interleukin-13 receptor subunit α-2 (IL-13Ra2 or CD213A2), mesothelin, interleukin 11 receptor α (IL-11Ra), prostate stem cell antigen (PSCA), protease serine 21, vascular endothelial growth factor receptor 2 (VEGFR2), Lewis (Y) antigen, CD24, platelet-derived growth factor receptor α (PDGFR-β), stage-specific embryonic antigen-4 (SSEA-4), CD20, folate receptor α, receptor tyrosine-protein kinase ERBB2 (Her2/neu), cell surface-associated mucoprotein 1 (MUC1), epidermal growth factor receptor (EGFR), neurocyte adhesion molecule (NCAM), prostase, prostate acid phosphatase (PAP), elongation factor 2 mutant (ELF2M), ephrin B2, fibroblast activated protein α (FAP), insulin-like growth factor 1 receptor (IGF-I receptor), carbonic anhydrase IX (CAIX), proteasome (e.g., proteasome, giantin factor) subunit B-type 9 (LMP2), glycoprotein 100 (gp100), oncogene fusion protein (bcr-abl) composed of breakpoint cluster region (BCR) and Abelson murine leukemia virus oncogene homolog 1 (Abl), tyrosinase, ephrin A-type receptor 2 (EphA2), fucosyl GM1; sialyl Lewis adhesion molecule (sLe), transglutaminase 5 (TGS5), high molecular weight-melanoma-associated antigen (HMWMAA), o-acetyl-GD2 ganglioside (OAcGD2), folate receptor β, tumor endothelial marker 1 (TEM1/CD248), tumor endothelial marker 7-associated (TEM7R), tight junction protein 6 (CLDN6), thyrotropin receptor (TSHR), G-protein-coupled receptor C-class Group 5 Member D (GPRC5D), chromosome X ORF 61 (CXORF61), CD97, CD179a, anaplastic lymphoma kinase (ALK), polysialic acid, placental specificity 1 (PLAC1), hexose moiety of globoH glycoceramide (GloboH), mammary gland differentiation antigen (NY-BR-1), uroplakin 2 (UPK2), hepatitis virus A cell receptor 1 (HAVCR1), adrenaline receptor 03 (ADRB3), pannexin 3 (PANX3), G-protein-coupled receptor 20 (GPR20), lymphocyte antigen 6 complex loci K9 (LY6K), olfactory receptor 51E2 (OR51E2), TCRγ variable ORF protein (TARP), Wilm tumor protein (WT1); cancer/testis antigen 1 (NY-ESO-1), cancer/testis antigen 2 (LAGE-1a), melanoma-associated antigen 1 (MAGE-A1), ETS translocation variant gene 6 located on chromosome 12p (ETV6-AML), sperm protein 17 (SPA17), X antigen family member 1A (XAGE1), angiogenin cell surface receptor 2 (Tie 2), melanoma cancer/testis antigen-1 (MAD-CT-1), melanoma cancer/testis antigen-2 (MAD-CT-2), Fos-associated antigen 1, p53, p53 mutant, prostate-specific protein (prostein), prostate cancer tumor antigen-1 (PCTA-1 or galectin 8), T cell-recognized melanoma antigen 1 (MelanA or MART1); rat sarcoma (Ras) mutant, human telomerase reverse transcriptase (hTERT), sarcoma translocation breakpoint, melanoma anti-apoptosis protein (ML-IAP), ERG (transmembrane protease, serine 2 (TMPRSS2) ETS fusion gene), N-acetylglucosaminyltransferase V (NA17), paired frame protein Pax-3 (PAX3), androgen receptor, cyclin B1, v-myc avian myelocytosis virus oncogene neuroblastoma-derived homologs (MYCN), Ras homolog family member C (RhoC), tyrosinase-associated protein 2 (TRP-2), cytochrome P450 1B1 (CYP1B1), T cell-recognized squamous cell cancer antigen 3 (SART3), paired frame protein Pax-5 (PAX5), proacrosomal protein binding protein sp32 (OY-TES1), lymphocyte-specific protein tyrosine kinase (LCK), A kinase anchorin 4 (AKAP-4), synovial sarcoma X breakpoint 2 (SSX2), receptor of advanced glycation end products (RAGE-1), legumain, human papilloma virus E6 (HPV E6), human papilloma virus E7 (HPV E7), intestinal carboxylesterase, mutated heat shock protein 70-2 (mut hsp70-2), CD79a, CD79b, CD72, leukocyte-associated immunoglobulin-like receptor 1 (LAIR1), Fc fragment of IgA receptor (FCAR or CD890), leukocyte immunoglobin-like receptor superfamily A member 2 (LILRA2), CD300 molecule-like family member f (CD300LF), C-type lectin domain family 12 member A (CLEC12A), bone marrow stromal cell antigen 2 (BST2), EGF-like modulus-containing mucoprotein-like hormone receptor-like 2 (EMR2), lymphocyte antigen 75 (LY75), glypican-3 (GPC3), Fc receptor-like 5 (FCRL5) and/or immunoglobulin λ-like peptide 1 (IGLL1).

TRAC Gene, HLA-A Gene, B2M Gene and the CIITA Gene

In the present application, the expression and/or activity of the TRAC gene and the HLA-A gene are/is down-regulated, the expression and/or activity of the B2M gene are/is not down-regulated, and the expression and/or activity of the CIITA gene are/is not down-regulated, as compared with corresponding wild type cells.

In the present application, as compared with a wild type cell, the expression and/or activity of the two genes are/is down-regulated, wherein the two genes consist of the TRAC gene and the HLA-A gene.

In the present application, the down-regulation of the expression level and/or activity of the genes includes a down-regulation of expression and/or activity of a nucleic acid molecule encoding the genes; and/or a down-regulation of expression and/or activity of a protein product encoded by the genes.

For example, the protein product can include a polypeptide.

In the present application, the down-regulated expression and/or activity of the TRAC gene and the HLA-A gene or the down-regulating the expression and/or activity of the TRAC gene and the HLA-A gene in the immune effector cells can include that, as compared with the corresponding cells which are not modified, the modification changes the structure of the nucleotide sequence of the TRAC gene and the HLA-A gene. The nucleotide sequence can include coding or non-coding region, such as, cis-regulatory element sequence, exon sequence, wherein the cis-regulatory element can include a promotor. The change can include deletion of partial or full sequences, insertion of exogenous fragments, mutation of base site, or the like. The inserted exogenous fragments can substitute or disrupt the sequence structures of the TRAC gene and the HLA-A gene, so that they cannot be normally translated. The mutation of base sites can include frameshift mutations, missense mutations, nonsense mutations, and the like. The change can include the modification of nucleotide sequence with a chemical group, such as, methylation, etc. The change of the structure of the nucleotide sequence can be detected by gene sequencing, such as, Sanger sequencing, bisulfite sequences, and the like.

In the present application, the down-regulated expression and/or activity of the TRAC gene and the HLA-A gene or the down-regulating the expression and/or activity of the TRAC gene and the HLA-A gene in the immune effector cells can further include that, as compared with the corresponding cells which are not modified, the modification enables the mRNA level of the TRAC gene and the HLA-A gene to be decreased. The mRNA level can be determined by experimental methods and biometrical methods that are well known by persons skilled in the art, e.g., in situ hybridization of molecular probe, real-time fluorescent quantitative PCR (qPCR, RT-PCR). The real-time fluorescent quantitative PCR can include SYBR green method, TaqMan method, two hybrid probe method, and molecular beacon method. The detecting results of the mRNA level allow unavoidable errors in experiments or statistics, which can be well known in the art. The error can be in a range of ±10%, e.g., in a range of ±8%, ±6%, ±5%, ±4%, or ±3%. The mRNA level is decreased by at least 30%, e.g., 35%, 40%, 45%, 50%, 55%, 60%, 65%, 70%, 75%, 80%, 85%, 90%, 95%, and 99%. For example, the mRNA of the TRAC gene and the HLA-A gene is undetectable in the modified immune effector cells.

In the present application, the down-regulated expression and/or activity of the TRAC gene and the HLA-A gene or the down-regulating the expression and/or activity of the TRAC gene and the HLA-A gene in the immune effector cells can further include that, as compared with the corresponding cells which are not modified, the modification enables the polypeptide level expressed by the TRAC gene and the HLA-A gene to be decreased. The polypeptide refers to polypeptides having the same structure and function as those generated by the expression of the TRAC gene and the HLA-A gene in the corresponding cells which are not modified, while polypeptides having changed structure and function generated by the expression of the TRAC gene and the HLA-A gene due to the change of nucleotide sequence are not used for comparison. The polypeptide level can be determined by experimental methods and biometric methods that are well known by persons skilled in the art, such as, flow cytometry, enzyme-linked immunosorbent assay (ELISA), cell immunofluorescence staining, and Western blotting (WB). The detecting results of the polypeptide level allow unavoidable errors in experiments or statistics, which can be well known in the art. The error can be in a range of ±10%, e.g., in a range of ±8%, ±6%, ±5%, ±4%, or ±3%. The polypeptide level is decreased by at least 30%, e.g., 35%, 40%, 45%, 50%, 55%, 60%, 65%, 70%, 75%, 80%, 85%, 90%, 95%, and 99%. For example, the polypeptide expressed by the TRAC gene and the HLA-A gene is not detectable in the modified immune effector cells.

In the present application, the down-regulated expression and/or activity of the TRAC gene and the HLA-A gene or the down-regulating the expression and/or activity of the TRAC gene and the HLA-A gene in the immune effector cells can refer to knockdown or knockout of the expression of the TRAC gene and the HLA-A gene or implementation of other operations that disrupt the function of TRAC protein and the HLA-A protein.

In the present application, the expression and/or activity of the B2M gene being not down-regulated and the expression and/or activity of the CIITA gene being not down-regulated, or not down-regulating the expression and/or activity of the B2M gene, and not down-regulating the expression and/or activity of the CIITA gene can include, as compared with the corresponding cells which are not modified, the mRNA level of the B2M gene and the CIITA gene are not decreased. The mRNA level can be determined by experimental methods and biometrical methods that are well known by persons skilled in the art, e.g., in situ hybridization of molecular probe, real-time fluorescent quantitative PCR (qPCR, RT-PCR). The real-time fluorescent quantitative PCR can include SYBR green method, TaqMan method, two hybrid probe method, and molecular beacon method. The detecting results of the mRNA level allow unavoidable errors in experiments or statistics, which can be well known in the art. The error can be in a range of ±10%, e.g., in a range of ±8%, ±6%, ±5%, ±4%, or ±3%. The mRNA level being not decreased can include a case that the level is increased or unchanged. The level being unchanged can include a case that there is no significant difference in the quantitative analysis of the corresponding mRNA of B2M gene and CIITA gene between the two (P>0.05).

In the present application, the expression and/or activity of the B2M gene being not down-regulated, and the expression and/or activity of the CIITA gene being not down-regulated, or not down-regulating the expression and/or activity of the B2M gene and not down-regulating the expression and/or activity of the CIITA gene can include that, as compared with the corresponding cells which are not modified, the level of the polypeptide expressed by the B2M gene and the CIITA gene is not decreased. The polypeptide refers to polypeptides having the same structure and function as those generated by the expression of the B2M gene and the CIITA gene in the corresponding cells which are not modified. The polypeptide level can be determined by experimental methods and biometric methods that are well known by persons skilled in the art, such as, flow cytometry, enzyme-linked immunosorbent assay (ELISA), cell immunofluorescence staining, and Western blotting (WB). The detecting results of the polypeptide level allow unavoidable errors in experiments or statistics, which can be well known in the art. The error can be in a range of ±10%, e.g., in a range of ±8%, ±6%, ±5%, ±4%, or ±3%. The polypeptide level being not decreased can include a case that the level is increased or unchanged. The level being unchanged can include a case that there is no significant difference in the quantitative analysis of the corresponding polypeptide of B2M gene and CIITA gene between the two (P>0.05).

In the present application, the expression and/or activity of the B2M gene being not down-regulated, and the expression and/or activity of the CIITA gene being not down-regulated, or not down-regulating the expression and/or activity of the B2M gene and not down-regulating the expression and/or activity of the CIITA gene can include a case that a manual intervention is not performed on the corresponding cells which are not modified against the CIITA gene and B2M gene and mRNA and/or polypeptide encoded by the CIITA gene and B2M gene. For example, the manual intervention can include introducing a nucleotide molecule or other compounds which can target the CIITA gene and the B2M gene or an mRNA molecule encoded thereby and which can change the structure or level thereof into the corresponding cells which are not modified.

In the present application, the expression and/or activity of the B2M gene being not down-regulated and the expression and/or activity of the CIITA gene being not down-regulated, or not down-regulating the expression and/or activity of the B2M gene and not down-regulating the expression and/or activity of the CIITA gene can include that, as compared with the corresponding cells which are not modified, the structure of the nucleotide sequence of the B2M gene and the CIITA gene are not changed. The structure of the nucleotide sequence being unchanged can be determined by gene sequencing, such as, Sanger sequencing, sulfite sequencing, etc. The nucleotide sequence being unchanged can include not only a case that there is no manual change, but also a case that there is naturally occurring change which would not affect the function.

In the present application, the expression and/or activity of the B2M gene being not down-regulated, and the expression and/or activity of the CIITA gene being not down-regulated, or not down-regulating the expression and/or activity of the B2M gene and not down-regulating the expression and/or activity of the CIITA gene can refer to a case that there is no modification with B2M gene and proteins encoded thereby, CIITA gene or proteins encoded thereby as targets.

In the present application, the expression level and/or activity of at most 2 alleles of the HLA-A gene are down-regulated. For example, the 2 alleles can be a pair of alleles of HLA-A gene in the immune effector cells. For example, the expression level and/or activity of 1 allele in the HLA-A gene is down-regulated.

In the present application, the TRAC gene can include a gene as shown by HGNC:12029 and all allele types thereof. For example, the TRAC gene and all allele types thereof can include the TRAC genotypes capable of existing in the immune effector cells. For example, the TRAC gene can include a nucleotide sequence as shown in SEQ ID No. 55.

For example, the TRAC gene can include a nucleotide sequence that is derived from human being and has 80% or greater, e.g., 85% or greater, 90% or greater, 95% or greater, 96% or greater, 97% or greater, 98% or greater, 99% or greater of identity as the nucleotide sequence as shown in SEQ ID No. 55.

In the present application, the HLA-A gene can include a gene as shown by HGNC:4931 and all allele types thereof. For example, the HLA-A gene can include all the HLA-A allele types included in the IMGT/HLA Database Version 3.38.0 (www.ebi.ac.uk/ipd/imgt/hla/) and named by the WHO HLA Factor Nomenclature Committee. The HLA-A allele genotypes and the sequence information thereof disclosed in the IMGT/HLA data 3.38.0 are incorporated herein by reference.

For example, the HLA-A allele can include any one or more of A*02, A*24, A*01, A*03, A*32, A*11, A*26, A*68, A*23, A*29, A*31, A*33, A*25, A*43, A*74, A*30, A*69.

For example, the HLA-A allele can include any one or more of A*02:01, A*03:01, A*01:01, A*24:02, A*68:01, A*11:01, A*31:01:02, A*29:02, A*32:01, A*26, A*23:01, A*30:02, A*25:01, A*33:03.

For example, the HLA-A allele can include any one or more of A*02:01:01, A*01:01:01, A*03:01:01, A*24:02:01, A*11:01:01, A*32:01:01, A*29:02:01, A*31:01:02, A*23:01:01, A*26:01:01, A*68:01:02, A*30:01:01, A*68:02:01, A*25:01:01, A*68:01:01, and A*02:05:01.

For example, the HLA-A allele can include any one or more of A*02, A*30, A*03, A*01, A*24, A*32, A*68, A*11, A*26, A*23, A*31, A*25.

For example, the HLA-A allele can include any one or more of A*02:01, A*03:01, A*24:02, A*01:01, A*11:01, A*26:01, A*25:01, A*68:01, A*32:01, A*31:01.

For example, the HLA-A allele can include any one or more of A*24, A*33, A*02, A*11, A*26, A*31, A*01, A*24:02, A*02:01, A*33:03, A*11:01, A*26:01, A*02:06, A*31:01:02, A*26:03, A*26:02, A*02:07, A*01:01, A*02:10, A*03:01.

For example, the HLA-A allele can include A*02, A*24, A*33, A*11, A*26, A*31, A*30, A*03, A*01, A*32, A*29, A*68, A*23, A*25, A*34, A*36, A*43, A*66, A*74.

For example, the HLA-A allele can include any one or more of A*24:02, A*33:03, A*02:01, A*11:01, A*02:01, A*31:01, A*26:01, A*02:07, A*30:01, A*26:02, A*01:01, A*03:01, A*30:04, A*26:03.

For example, the HLA-A allele can include any one or more of A*02:01, A*11:01, A*24:02, A*30:01, A*26:01, A*23:01, A*02:07, A*02:06, A*03:01, A*01:01, A*31:01:02, A*33:03, A*32:01, A*68:01, A*02:03, A*02:05.

For example, the HLA-A allele can include any one or more of A*03:01, A*02:01, A*23:01, A*01:01, A*30:02, A*30:01, A*33:03, A*29:02, A*74:01, A*36:01, A*24:02, A*02:02, A*68:01, A*68:02, A*34:02, A*66:02, A*31:01:02, A*32:01, A*02:05, A*66:01, A*26:01.

For example, the HLA-A allele can include any one or more of A*02, A*11, A*24, A*30, A*33, A*03, A*01, A*26.

For example, the HLA-A allele can include any one or more of A*11:01, A*24:02, A*02:01, A*02:07, A*33:03, A*02:06 and A*30:01.

For example, the HLA-A allele can include any one or more of HLA-A*02:01:01:01, HLA-A*11:01:01:01, HLA-A*24:02:01, HLA-A*30:01:01:01, HLA-A*33:01:01:01, HLA-A*03:01:01:01, HLA-A*01:01:01:01, HLA-A*26:01:01:01.

For example, the HLA-A gene can include a nucleic acid sequence as shown in any one of SEQ ID No. 56-63.

For example, the HLA-A gene can include a nucleotide sequence that is derived from human beings and has 80% or greater, e.g., 85% or greater, 90% or greater, 95% or greater, 96% or greater, 97% or greater, 98% or greater, 99% or greater of identity as a nucleic acid sequence as shown in any one of SEQ ID No. 56-63.

Modification

In the present application, the modification can include gene knockout and/or gene silencing.

For example, the modification can include deletion of full or partial gene fragments, gene mutations and/or gene silencing.

For example, the gene knockout can include deletion of full or partial gene fragments, gene mutations, etc.

For example, the gene can include the HLA-A gene and/or the TRAC gene.

For example, the modification can include that any one of the two TRAC alleles is knockout and any one of the two HLA-A alleles is knockout in the immune cells.

For example, the modification can include that the two TRAC alleles are knockout and any one of the two HLA-A alleles is knockout in the immune cells.

For example, the modification can include that any one of the two TRAC alleles is knockout and the two HLA-A alleles are knockout.

For example, the modification can include that the two TRAC alleles are knockout and the two HLA-A alleles are knockout.

For example, the deletion of partial gene fragments can include the deletion of >1 exon sequence.

For example, the gene mutations can include changes of composition or arrangement order of base pairs, which can commonly result in, e.g., frameshift mutations, missense mutations, and/or nonsense mutations, and the like. The missense mutations generally refer to the change from a codon encoding an amino acid to a codon encoding another amino acid due to the change of a certain base pair, resulting in the change of the corresponding amino acids constituting a protein. The frameshift mutations generally refer to the insertion or deletion of one or several bases that are not integral multiples of 3 in the DNA strands, resulting in the change of coding codon. The nonsense mutations generally refer to the change from a codon encoding an amino acid to a terminator due to the change of a certain base pair, causing early termination of the protein synthesis when it reaches the site.

For example, the change of composition or arrangement order of base pairs can include changes of a single nucleotide or base (also known as point mutation) and/or changes of plural nucleotides or bases. For example, the change of the single nucleotide or base can include substitution of a base or nucleotide with another base or nucleotide, and insertion or deletion of a base. For example, the change of the plural nucleotides or bases can include loss of a segment of base sequence, insertion of a segment of base sequence, and/or rearrangement of a segment of base sequence. The segment of base sequence can be a portion of any exon and/or intron in a gene. The rearrangement can include repeat, inversion, translocation of a segment of base sequence, etc.

For example, the gene silencing can include a transcriptional gene silencing (TGS) and/or a post-transcriptional gene silencing (PTGS) at a transcriptional level. The silencing at the transcriptional level can include the methylation of DNA molecules so as to suppress the DNAs, e.g., the methylation of promotor sequence. The post-transcriptional gene silencing can include a variation of gene expression caused by specifically interfering with the target RNA after gene transcription. For example, the mRNA level can be reduced by RNA interference (RNAi).

In the present application, the modification can include a technology or method including replacing the endogenous normal gene with an exogenous nucleotide sequence via homologous recombination to inactivate the endogenous normal gene. The exogenous nucleotide sequence can be well known. For example, the exogenous nucleotide sequence can be a partial fragment of the endogenous normal gene. For example, the exogenous nucleotide sequence can include, from 5' to 3', a homologous arm 1, a nucleotide sequence to be inserted, and a homologous arm 2 in sequence. The nucleotide sequence to be inserted can include a reporter gene, a noncoding sequence or a varied sequence of an endogenous normal gene.

In the present application, the modification can include administering one or more substances selected from the group consisting of antisense RNA, siRNA, shRNA, and CRISPR/Cas9 system to the immunologic effector cells.

In the present application, the antisense RNA can be a single stranded RNA complementary to the transcript mRNA (messenger RNA).

For example, the complementation means that at least 60% of nucleotide sequence of the antisense RNA is complementary to the mRNA, e.g., at least 70%, e.g., at least 80%, e.g., at least 90%, e.g., 100%.

For example, the binding of the antisense RNA to a target mRNA can cause an increased sensitivity of the double stranded RNA molecule on RNA enzyme III, thereby degrading the molecule.

For example, the antisense RNA binds to the upstream noncoding region of the mRNA, thereby inhibiting the translation of the target mRNA.

For example, the antisense RNA is artificial.

For example, the antisense RNA cannot form a short hairpin structure.

In the present application, the antisense RNA includes a nucleotide sequence as shown in any one of SEQ ID NO. 93-96.

In the present application, the siRNA can be a class of double stranded and noncoding RNA molecules having about 18-28 base pairs in length.

For example, the siRNA can result in the degradation of mRNA by means of complementary binding to the mRNA.

For example, the siRNA can include 18, 19, 20, 21, 22, 23, 24, 25, 26, 27, 28 base pairs in length.

For example, the siRNA is artificial.

For example, the siRNA is generated by treating the intracellular double stranded RNA or shRNA with Dicer enzyme.

In the present application, the shRNA refers to a class of RNAs capable of forming a short hairpin structure.

For example, the shRNA can include two invert repeats, as well as a loop sequence between the two short invert repeats.

For example, the shRNA includes at least 18 continuous nucleic acid sequences that can complementarily bind to the target mRNA, e.g., at least 19, e.g., at least 20, e.g., at least 21, e.g., at least 22, e.g., at least 23, e.g., at least 24, e.g., at least 25, e.g., at least 26.

For example, the shRNA does not include the sgRNA of the present application.

In the present application, the modification can include administering CRISPR/Cas system to the immunologic effector cells.

CRISPR/Cas System

In the present application, the CRISPR/Cas system can include a guide RNA (gRNA) and Cas enzyme. The gRNA can include crRNA and tracrRNA. When the crRNA and the tracrRNA are located in two different nucleotide molecules, respectively, the gRNA can be called dgRNA (bimolecular gRNA). When the crRNA and the tracrRNA are located in the same nucleotide molecule, the gRNA can be called sgRNA (unimolecular gRNA).

In the present application, the CRISPR/Cas system can include a gRNA nucleic acid sequence and a Cas protein. For instance, the gRNA nucleic acid sequence and the Cas protein form an RNP complex.

In the present application, the CRISPR/Cas system can further include a nucleic acid sequence encoding the gRNA and a nucleic acid sequence encoding Cas protein. The nucleic acid sequence encoding the gRNA and the nucleic acid sequence encoding the Cas protein can be disposed in vectors that are commonly used in the art, e.g., plasmids, viruses (e.g., adenoviruses, lentiviruses, retroviruses), or the like. For example, the nucleic acid sequence encoding the gRNA and the nucleic acid sequence encoding the Cas protein can be located in the same or different vectors. For example, the nucleic acid sequence encoding the tracrRNA and the sequence encoding the crRNA can be located in the same or different vectors. Promotors for driving the expression of various coding sequences can be the same or different.

In the present application, the CRISPR/Cas system can include more than one guide RNA. Each guide RNA can include a different targeting sequence, so that the CRISPR/Cas system cleaves more than one target sequence. For example, one or more guide RNAs can include the same or different characteristics, e.g., activity or stability in the CRISPR/Cas complex. If more than one guide RNAs are used, each guide RNA can be encoded in the same or different vectors. Promotors for driving the expression of the more than one guide RNAs can be the same or different. For example, the guide RNA includes those targeting the HLA-A gene or targeting the TRAC gene.

In the present application, the modification further includes administering a Cas enzyme to the cell. The Cas enzyme can include a Cas protein, and a nucleic acid sequence encoding the Cas protein.

For example, the Cas protein can include at least one domain that interacts with the guide RNA (gRNA). For example, the Cas protein can be directed by the guide RNA to a target sequence. For example, the guide RNA interacts with the Cas protein and the target sequence, thereby directing the binding of the Cas protein to the target sequence. For example, the guide RNA provides a specificity to the target cleaving, wherein the Cas protein can be universal and is paired with various guide RNAs to cleave different target sequences. For example, the Cas protein can cleave a single or double stranded DNA. For example, the Cas protein can cleave RNA. For example, the Cas protein can lead to an incision occurred in the RNA/DNA. For example, the Cas protein includes at least one DNA binding domain and at least one nuclease domain. For example, the nuclease can be exogenous in relation to the DNA binding domain; e.g., the nuclease activity can be changed by modifying the Cas protein. For example, the Cas protein can be used for binding to the DNA and regulating the expression or activity of the DNA. For example, the Cas protein can be a Cas nuclease.

In the present application, the CRISPR/Cas system can include Class 1 or Class 2 system components, including a ribonucleotide-protein complex (see, e.g., Makarova et al., Nat Rev Microbiol, 13(11):722-36(2015); Shmakov et al., Molecular Cell, 60:385-397(2015). Of those, Class 2 CRISPR/Cas system has a simple proteineous effector. Type II, V and VI Cas proteins can be a simple protein, an RNA guide nuclease, which are called "Class 2 Cas nuclease" in the present application. Class 2 Cas nuclease can include Cas9, Cpf1, C2c1, C2c2 and C2c3 proteins. Cas9 or Cpf1 protein (Zetsche et al., Cell, 163:1-13(2015)) can include an RuvC-like nuclease domain or an HNH-like nuclease domain, the Cpf1 sequence in Zetsche is incorporated herein by reference in its entirety.

For example, Cas protein can be derived from Type II CRISPR/Cas system (that is, the Cas9 protein of the CRISPR/Cas9 system) or Type V CRISPR/Cas system (e.g., Cpf1 protein). For example, the Cas protein can be derived from Class 2 CRISPR/Cas system, e.g., Cas9 protein or Cpf1 protein. Proteins of Class 2 Cas nuclease family are enzymes with DNA endonuclease activity, which can be directed to cleave the desired nucleic acid target by designing an appropriate guide RNA as further described herein.

For example, the components of Class 2 CRISPR/Cas system can be derived from Type IIA, IIB, IIC, V or VI system, including Cas9 and its orthologs. Cas9 protein or its orthologs can be derived from exemplary species of *Streptococcus pyogenes, Streptococcus thermophilus, Streptococcus* sp., *Staphylococcus aureus, Listeria in-nocua, Lactobacillus gasseri, Francisella novicida, Wolinella succinogenes, Neisseria meningitidis, Campylobacter jejuni, Pasteurella multocida, Fibrobacter succinogene, Rhodospirillum rubrum, Nocardiopsis dassonvillei, Streptomyces pristinaespiralis, Streptomyces viridochromogenes, Streptosporangium roseum, Alicyclobacillus acidocaldarius, Bacillus pseudomycoides, Lactobacillus delbrueckii, Lactobacillus salivarius, Lactobacillus buchneri, Treponema denticola, Microscilla mari-na, Burkholderiales bacterium, Polaromonas naphthalenivorans, Polaromonas* sp., Cyanothece sp., *Microcystis aeruginosa, Synechococcus* sp., *Acetohalobium arabati-cum, Clostridium botulinum, Clostridium difficile, Marinobacter* sp., *Nitrosococcus halophilus, Anabaena variabilis, Nodularia spumigena, Nostoc* sp., *Arthrospira maxima, Arthrospira platensis, Arthrospira* sp., *Lyngbya* sp., *Microcoleus chthonoplastes, Oscillatoria* sp., *Thermosipho africanus, Neisseria cinereal, Campylobacter lari*, or *Corynebacterium diphtheria.*

For example, the Cas9 protein can be derived from *Streptococcus pyogenes*. For example, the Cas9 protein can be derived from *Streptococcus thermophilus*. For example, the Cas9 protein can be derived from *Staphylococcus aureus*. For example, the Cpf1 protein can be derived from *Francisella tularensis, Acidaminococcus, Eubacterium eligens, Leptospira inadai, Prevotella dis-iens* or *Porphyromonas macacae*. For example, the Cpf1 protein can be derived from Acidaminococcus or Lachnospiraceae.

For example, the Cas9 protein can include an amino acid sequence having 60%, 65%, 70%, 75%, 80%, 85%, 90%, 95%, 96%, 97%, 98%, or 99% of identity with *Streptococcus pyogenes* Cas9.

For example, the Cas9 protein can include an amino acid sequence as shown in SEQ ID NO: 65.

For example, the exemplary nucleic acid sequences encoding Cas9 protein are described in the following literatures: Cong et al., SCIENCE 2013,399(6121):819-823; Wang et al., CELL 2013,153(4):910-918; Mali et al., SCIENCE 2013,399(6121):823-826; Jinek et al., SCIENCE 2012,337(6096):816-821.

For example, the nucleotide sequence encoding Cas9 protein is as shown in SEQ ID NO: 64.

For example, the Cas9 protein can be modified. For example, the modification may include amino acid substitution and forming a fusion protein with other polypeptide fragments. The other polypeptide fragments can include PEST sequences, ubiquitin, polyubiquitin, and nuclear localization signal (NLS).

In the present application, the crRNA can include a targeting sequence, by which the gRNA can target any target sequence. For example, the complementary degree between the targeting sequence and the targeting sequence of the target nucleic acid molecule can be about 60%, 65%, 70%, 75%, 80%, 85%, 90%, 95%, 97%, 98%, 99% or 100%. For example, the targeting sequence can be 100% complementary to the targeting sequence of the target nucleic acid molecule. For example, the targeting sequence and the targeting sequence of the target nucleic acid molecule can include at least one mispairing. For example, the targeting sequence and the targeting sequence of the target nucleic acid molecule can include 1, 2, 3, 4, 5, 6, 7, 8, 9 or 10 mispairings. For example, the targeting sequence and the targeting sequence of the target nucleic acid molecule can include 1-6 mispairings. For example, the targeting sequence and the targeting sequence of the target nucleic acid molecule can include 5 or 6 mispairings. For example, the targeting sequence and the targeting sequence of the target nucleic acid molecule do not include a mispairing.

In the present application, the length of the targeting sequence can depend on the used CRISPR/Cas system and components. For example, different Cas proteins derived from different bacteria species have different optimal targeting sequence length. Moreover, the targeting sequence can include 5, 6, 7, 8, 9, 10, 11, 12, 13, 14, 15, 16, 17, 18, 19, 20, 21, 22, 23, 24, 25, 26, 27, 28, 29, 30, 35, 40, 45, 50 or more than 50 nucleotides in length. For example, the targeting sequence can include 18-24 nucleotides in length. For example, the targeting sequence can include 19-21 nucleotides in length. For example, the targeting sequence can include 20 nucleotides in length.

In the present application, the crRNA can further include a crRNA flagpole sequence including any sequence that can be complementary to the tracrRNA so as to facilitate the formation of a CRISPR/Cas complex. For example, the flagpole sequence can include a full or a portion of sequence of naturally occurring crRNA that is complementary to the tracrRNA in the same CRISPR/Cas system (also known as "label" or "handle"). For example, the flagpole sequence can include a full or a portion of repeat sequence from naturally occurring CRISPR/Cas system. For example, the flagpole sequence can include a truncated or modified label or a handle sequence. The portion in the tracrRNA complementary to the crRNA flagpole sequence can be called tracrRNA flagpole sequence. For example, the complementary degree between the tracrRNA and the flagpole portion hybridized with the tracrRNA along the shorter of the two sequences can be about 40%, 50%, 60%, 70%, 80% or higher. For example, the tracrRNA and the flagpole portion hybridized with the tracrRNA along the shorter of the two sequences are not 100% complementary. The length of the crRNA flagpole sequence can depend on the used CRISPR/Cas system or tracrRNA. For example, the crRNA flagpole sequence can include 10-50 nucleotides or more than 50 nucleotides in length. For example, the crRNA flagpole sequence can include 15-40 nucleotides in length. For example, the crRNA flagpole sequence can include 20-30 nucleotides in length. For example, the crRNA flagpole sequence can include 22 nucleotides in length. When a dual-guide RNA is used, there can be no upper limit in the crRNA flagpole sequence length.

In the present application, the tracrRNA can include a full or a portion of wild-type tracrRNA sequence derived from naturally occurring CRISPR/Cas system. For example, tracrRNA can include a truncated or modified variant of wild-type tracrRNA. The length of the tracrRNA can depend on the used CRISPR/Cas system. For example, the tracr RNA can include 5, 6, 7, 8, 9, 10, 11, 12, 13, 14, 15, 16, 17, 18, 19, 20, 25, 30, 40, 50, 60, 70, 80, 90, 100 or more than 100 nucleotides in length. For example, the length of tracr is at least 20 nucleotides. For example, the length of tracrRNA is at least 40 nucleotides. For example, the tracrRNA can include a secondary structure, e.g., one or more hairpin or stem-loop structures, or one or more convex structures.

In the present application, the guide RNA can include two RNA molecules, and called "dual-guide RNA" or "dgRNA"

herein. For example, the dgRNA can include a first RNA molecule containing a crRNA and a second RNA molecule containing a tracrRNA. The first and the second RNA molecules can form an RNA duplex by base pairing between the flagpole sequences on the crRNA and the tracr RNA.

For example, the first RNA molecule can include, from 5' to 3', a targeting sequence complementary to a target sequence, and a crRNA flagpole sequence. The second RNA molecule can include, from 5' to 3', a tracrRNA flagpole sequence complementary to a crRNA flagpole sequence, and a nuclease binding sequence. For instance, the nuclease binding sequence can be a Cas nuclease, such as, Cas9.

In the present application, the guide RNA can include a single RNA molecule, called "single molecular gRNA" or "sgRNA". For example, the sgRNA can include a tracrRNA, a crRNA covalently linked to the tracrRNA. For example, the crRNA and the tracrRNA can be covalently linked through a linker nucleic acid sequence. For example, the single molecular gRNA can include a loop-stem structure formed by base pairing between the flagpole sequences on the crRNA and the tracr RNA. For example, the sgRNA is a "Cas9sgRNA" that can mediate a DNA cleavage by means of Cas9 protein. For example, the sgRNA is a "Cpf1sgRNA" that can mediate a DNA cleavage by means of Cpf1 protein.

For example, the single molecular gRNA or sgRNA can include, from 5' to 3', a crRNA, a loop, and a tracrRNA. The crRNA can include, from 5' to 3', a targeting sequence complementary to the target sequence, and a crRNA flagpole sequence. The tracrRNA can include, from 5' to 3', a tracrRNA flagpole sequence complementary to a crRNA flagpole sequence, and a nuclease binding sequence. For example, the nuclease binding sequence can be a Cas nuclease. For example, Cas9.

For example, the single molecular gRNA or sgRNA can include, from 5' to 3', a targeting sequence complementary to the target sequence, a crRNA flagpole sequence, a loop, a tracrRNA flagpole sequence complementary to a crRNA flagpole sequence, and a nuclease binding sequence.

In the present application, the gRNA can further include modified nucleosides or nucleotides. For example, the modification can be changing (e.g., replacing) one or two non-linker phosphate oxygens and/or one or more linker phosphate oxygens in the phosphate diester bond, e.g., changing (e.g., replacing) the components of ribose, e.g., replacing the 2'hydroxyl group on ribose; e.g., replacing the phosphate moiety with a dephosphorization linker; e.g., modification or replacement of naturally occurring nuclear bases; e.g., replacing or modifying the backbone of ribose phosphate; e.g., modification of the 3' or 5' end of an oligonucleotide, such as deleting, modifying, or replacing a terminal phosphate group or a conjugated portion, capping or splicing (e.g., 3' or 5' capping may include sugar and/or backbone modifications); such as, modifying or replacing sugars.

For example, introducing the modified nucleosides or nucleotides increases the stability to the nuclease. For example, introducing the modified nucleoside or nucleotide reduces the congenital immune reaction. The congenital reactions include a cellular reaction against an exogenous nucleic acid (including single strand nucleic acids), that can involve inducing the expression and release of cytokines (especially interferons) and inducing death of cells.

For instance, the modification can include administering an sgRNA targeting an exon of the HLA-A gene to the immunologic effector cells.

For instance, the sgRNA targeting the exon of the HLA-A gene can include a nucleotide sequence shown in any one of SEQ ID No. 16-54 and 91-92.

For instance, the sgRNA targeting the exon portion of the HLA-A gene can include a nucleotide sequence having at least 70% of identity with a nucleotide sequence as shown in any one of SEQ ID No: 16-54 and 91-92, such as, at least 75%, 80%, 85%, 90%, 95%, 96%, 97%, 98%, and 99%.

For example, the modification can include administering an sgRNA targeting an exon of the TRAC gene to the immunologic effector cells.

For example, the sgRNA targeting the exon of the TRAC gene can include a nucleotide sequence shown in any one of SEQ ID No. 1-15.

For example, the sgRNA targeting the exon of the TRAC gene can include a nucleotide sequence having at least 70% with a nucleotide sequence as shown in any one of SEQ ID No. 1-15, e.g., at least 75%, 80%, 85%, 90%, 95%, 96%, 97%, 98%, and 99%.

Chimeric Antigen Receptor (CAR)

In the present application, the immunologic effector cells include a nucleic acid encoding a chimeric antigen receptor (CAR), and the CAR includes an antigen binding domain, a hinge region, a transmembrane domain, a co-stimulating structure, and a primary signal transduction domain.

For example, the antigen binding domain specifically binds to a tumor antigen. For example, the tumor antigen is selected from the group consisting of CD19, CD123, CD22, CD30, CD171, CA125, C-met, LICAM, EC, DLL3, CD99, 5T4, CD138, CS-1 (also known as CD2 subclass 1, CRACC, SLAMF7, CD319 or 19A24), C-type lectin-like molecule-1 (CLL-1 or CLECL1), CD33, epidermal growth factor receptor variant III (EGFRvIII), ganglioside G2 (GD2), ganglioside GD3, TNF receptor family member B cell mature antigen (BCMA), Tn antigen (e.g., Tn Ag, GalNAca-Ser/Thr), prostate-specific membrane antigen (PSMA); receptor tyrosine kinase-like orphan receptor 1 (ROR1), Fms-like tyrosine kinase 3 (FLT3); tumor-associated glycoprotein 72 (TAG72), CD38, CD44v6, carcino-embryonic antigen (CEA), epithelial cell adhesion molecule (EPCAM), B7H3 (CD276), KIT (CD117), interleukin-13 receptor subunit α-2 (IL-13Ra2 or CD213A2), mesothelin, interleukin 11 receptor α (IL-11Ra), prostate stem cell antigen (PSCA), protease serine 21, vascular endothelial growth factor receptor 2 (VEGFR2), Lewis (Y) antigen, CD24, platelet-derived growth factor receptor α (PDGFR-β), stage-specific embryonic antigen-4 (SSEA-4), CD20, folate receptor α, receptor tyrosine-protein kinase ERBB2 (Her2/neu), cell surface-associated mucoprotein 1 (MUC1), epidermal growth factor receptor (EGFR), neurocyte adhesion molecule (NCAM), Prostase, prostate acid phosphatase (PAP), elongation factor 2 mutant (ELF2M), ephrin B2, fibroblast activated protein α (FAP), insulin-like growth factor 1 receptor (IGF-I receptor), carbonic anhydrase IX (CAIX), proteasome (e.g., proteasome, giantin factor) subunit B-type 9 (LMP2), glycoprotein 100 (gp100), oncogene fusion protein (bcr-abl) composed of breakpoint cluster region (BCR) and Abelson murine leukemia virus oncogene homolog 1 (Abl), tyrosinase, ephrin A-type receptor 2 (EphA2), fucosyl GM1; sialyl Lewis adhesion molecule (sLe), transglutaminase 5 (TGS5), high molecular weight-melanoma-associated antigen (HMWMAA), o-acetyl-GD2 ganglioside (OAcGD2), folate receptor β, tumor endothelial marker 1 (TEM1/CD248), tumor endothelial marker 7-associated (TEM7R), tight junction protein 6 (CLDN6), thyrotropin receptor (TSHR), G-protein-coupled receptor C-class Group 5 Member D (GPRC5D), chromosome X ORF 61 (CXORF61), CD97, CD179a, anaplastic lymphoma kinase (ALK), polysialic acid, placental specificity 1 (PLAC1), hexose moiety of globoH glycoceramide (GloboH), mammary gland differentiation antigen (NY-BR-1), uroplakin 2 (UPK2), hepatitis virus A cell receptor 1 (HAVCR1), adrenaline receptor 03 (ADRB3), pannexin 3 (PANX3), G-protein-coupled receptor 20 (GPR20), lymphocyte antigen 6 complex loci K9 (LY6K), olfactory receptor 51E2 (OR51E2), TCRγ variable ORF protein (TARP), Wilm tumor protein (WT1); cancer/testis antigen 1 (NY-ESO-1), cancer/testis antigen 2 (LAGE-1a), melanoma-associated antigen 1 (MAGE-A1), ETS translocation variant gene 6 located on chromosome 12p (ETV6-AML), sperm protein 17 (SPA17), X antigen family member 1A (XAGE1), angiogenin cell surface receptor 2 (Tie 2), melanoma cancer/testis antigen-1 (MAD-CT-1), melanoma cancer/testis antigen-2 (MAD-CT-2), Fos-associated antigen 1, p53, p53 mutant, prostate-specific protein (prostein), prostate cancer tumor antigen-1 (PCTA-1 or galectin 8), T cell-recognized melanoma antigen 1 (MelanA or MART1); rat sarcoma (Ras) mutant, human telomerase reverse transcriptase (hTERT), sarcoma translocation breakpoint, melanoma anti-apoptosis protein (ML-IAP), ERG (transmembrane protease, serine 2 (TMPRSS2) ETS fusion gene), N-acetylglucosaminyltransferase V (NA17), paired frame protein Pax-3 (PAX3), androgen receptor, cyclin B1, v-myc avian myelocytosis virus oncogene neuroblastoma-derived homologs (MYCN), Ras homolog family member C (RhoC), tyrosinase-associated protein 2 (TRP-2), cytochrome P450 1B1 (CYP1B1), T cell-recognized squamous cell cancer antigen 3 (SART3), paired frame protein Pax-5 (PAX5), proacrosomal protein binding protein sp32 (OY-TES1), lymphocyte-specific protein tyrosine kinase (LCK), A kinase anchorin 4 (AKAP-4), synovial sarcoma X breakpoint 2 (SSX2), receptor of advanced glycation end products (RAGE-1), legumain, human papilloma virus E6 (HPV E6), human papilloma virus E7 (HPV E7), intestinal carboxylesterase, mutated heat shock protein 70-2 (mut hsp70-2), CD79a, CD79b, CD72, leukocyte-associated immunoglobulin-like receptor 1 (LAIR1), Fc fragment of IgA receptor (FCAR or CD890), leukocyte immunoglobin-like receptor superfamily A member 2 (LILRA2), CD300 molecule-like family member f (CD300LF), C-type lectin domain family 12 member A (CLEC12A), bone marrow stromal cell antigen 2 (BST2), EGF-like modulus-containing mucoprotein-like hormone receptor-like 2 (EMR2), lymphocyte antigen 75 (LY75), glypican-3 (GPC3), Fc receptor-like 5 (FCRL5) and/or immunoglobulin λ-like peptide 1 (IGLL1).

In the present application, the antigen binding domain can include an antibody specifically binding to the tumor antigen or a fragment of antigen binding thereof. For example, the antibody specifically binding to GPC3 or a fragment of antigen binding thereof as described in the present application can include, but is not limited to, recombinant antibody, monoclonal antibody, human antibody, humanized antibody, chimeric antibody, bispecific antibody, single stranded antibody, duplex antibody, triplex antibody, quadruplex antibody, Fv fragment, scFv fragment, Fab fragment, Fab' fragment, F (ab') 2 fragment and Camelidae single domain antibody.

For example, the antibody can be a humanized antibody. It can be an antibody that immuno-specifically binds to an associated antigen (e.g., human CD19, BCMA or GPC3) and contains a framework (FR) region having substantially an amino acid sequence of human antibody and a complementary determining region (CDR) having substantially an amino acid sequence of non-human antibody, or its variant, derivative, analogue, or fragment. As used herein, "substantially" with reference to the CDR means that the amino acid sequence of the CDR has at least 80%, at least 85%, at least 90%, at least 95%, at least 98% or at least 99% of identity with an amino acid sequence of nonhuman antibody CDR.

For example, the antigen binding fragment can include Fab, Fab', F (ab) 2, Fv fragment, F (ab') 2, scFv, di-scFv and/or dAb.

For example, the single stranded antibody is scFv.

For example, the antigen binding domain targets a solid tumor. For example, the solid tumor is selected from the group consisting of: liver cancer, stomach cancer, lung cancer, breast cancer, colon cancer, rectal cancer, renal cell carcinoma, liver cancer, non-small cell lung cancer, small intestine cancer, esophagus cancer, melanoma, osteosarcoma, pancreatic cancer, skin cancer, head or neck cancer, cutaneous or intraocular malignant melanoma, uterus cancer, ovarian cancer, rectal cancer, testis cancer, fallopian tube carcinoma, endometrial cancer, cervical cancer, vaginal cancer, vulval cancer, Hodgkin's disease, non-Hodgkin's lymphoma, carcinoma of endocrine system, thyroid cancer, parathyroid cancer, adrenal carcinoma, soft tissue sarcoma, urethral carcinoma, carcinoma of penis, pediatric solid tumor, bladder cancer, renal or ureteral cancer, carcinoma of renal pelvis, central nervous system (CNS) tumor, primary CNS lymphoma, tumor angiogenesis, spinal tumor, brainstem glioma, pituitary adenoma, Kaposi sarcoma, epidermoid, squamous cell carcinoma, T cell lymphoma, and metastatic lesions of these cancers.

For example, the antigen binding domain targets a non-solid tumor. For example, the non-solid tumor is selected from the group consisting of chronic lymphoblastic leukemia (CLL), acute leukemia, acute lymphoblastic leukemia (ALL), B cell acute lymphoblastic leukemia (B-ALL), T cell acute lymphoblastic leukemia (T-ALL), chronic myeloid leukemia (CML), acute myeloid leukemia (AML), B cell prolymphocytic leukemia, blast cell plasmacytoid dendritic cytoma, Burkitt's lymphoma, diffuse large B cell lymphoma, follicular lymphoma, hairy cell leukemia, small or large cell follicular lymphoma, malignant lymphoproliferative conditions, MALT lymphoma, mantle cell lymphoma, marginal zone lymphoma, multiple myeloma, myelodysplasia and myelodysplastic syndrome, non-Hodgkin's lymphoma, Hodgkin's lymphoma, plasmablast lymphoma, plasmacytoid dendritic cytoma, and Waldenstrom macroglobulinemia.

In the present application, the transmembrane domain can include a transmembrane domain of protein selected from the group consisting of CD28, CD3e, CD45, CD4, CD5, CD8, CD9, CD16, CD22, CD33, CD37, CD64, CD80, CD86, CD134, CD137 and CD154.

In the present application, the costimulatory domain can include a costimulatory domain of protein selected from the group consisting of CD137, CD28, 4-1BB, OX40 and ICOS.

In the present application, the intracellular signal transduction domain can include a signal transduction domain derived from CD3ζ.

In the present application, the hinge region connects the antigen binding domain with the transmembrane domain, and includes a hinge region of protein selected from the group consisting of IgG1, IgG4, IgD, and CD8.

Composition, Use

The present application provides a composition including the immunologic effector cells of the present application and a pharmaceutically acceptable carrier.

For example, the composition includes a cell population, wherein the cell population includes the modified immunologic effector cell of the present application.

For example, the ratio of the modified immune effector cells to the total cells in the cell population is at least 0.001%, at least 0.01%, at least 0.1%, at least 1%, at least 5%, at least 10%, at least 15%, at least 20%, at least 25%, at least 30%, at least 35%, at least 40%, at least 45%, at least 50%, at least 53%, at least 55%, at least 58%, at least 60%, at least 63%, at least 65%, at least 68%, at least 70%, at least 73%, at least 75%, at least 78%, at least 80%, at least 83%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%.

For example, the cell population can include the modified immune effector cells and the corresponding unmodified immune effector cells.

For example, the modified immune effector cells can include cells in which any one of the two TRAC alleles is knockout and any one of the two HLA-A alleles is knockout, cells in which both of the two TRAC allele are knockout and any one of the two HLA-A alleles is knockout, cells in which any one of the two TRAC alleles is knockout and both of the two HLA-A alleles are knockout, and cells in which both of the two TRAC alleles are knockout and both of the two HLA-A alleles are knockout.

For example, the cell population can be a cell population obtained by treating a population of the immune effector cells by means of genetic engineering, wherein the means of genetic engineering include administering the antisense RNA, the siRNA, the shRNA and/or CRISPR/Cas9 system to the cell population of the immune effector cells. For example, the CRISPR/Cas9 system can include the sgRNA targeting the exon of the HLA-A gene, the sgRNA targeting the exon of the TRAC gene, and the Cas9 protein.

For example, the cell population can include a cell population obtained by editing a cell population of the immune effector cells with CRISPR/Cas9 system with an editing efficiency of at least 30%, at least 35%, at least 40%, at least 45%, at least 50%, at least 53%, at least 55%, at least 58%, at least 60%, at least 63%, at least 65%, at least 68%, at least 70%, at least 73%, at least 75%, at least 78%, at least 80%, at least 83%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%.

For example, the editing efficiency can be obtained by Sanger sequencing, TA clone sequencing, and flow cytometry.

For example, the cell population can include a cell population obtained by administering the antisense RNA, the siRNA, the shRNA of the present application to the cell population of the immune effector cells, wherein the mRNA expression in the cell population is reduced by at least 10% at least 20%, at least 30%, at least 35%, at least 40%, at least 45%, at least 50%, at least 53%, at least 55%, at least 58%, at least 60%, at least 63%, at least 65%, at least 68%, at least 70%, at least 73%, at least 75%, at least 78%, at least 80%, at least 83%, at least 85%, at least 86%, at least 87%, at least 88%, at least 89%, at least 90%, as compared with that in the cell population of the corresponding immune effector cells prior to the administration.

For example, the cell population can include a cell population obtained by administering the antisense RNA, the siRNA, the shRNA of the present application to the cell population of the immune effector cells, wherein the expression of protein in the cell population is reduced by at least 10%, at least 20%, at least 30%, at least 35%, at least 40%, at least 45%, at least 50%, at least 53%, at least 55%, at least 58%, at least 60%, at least 63%, at least 65%, at least 68%, at least 70%, at least 73%, at least 75%, at least 78%, at least 80%, at least 83%, at least 85%, at least 86%, at least 87%, at least 88%, at least 89%, at least 90%, as compared with that in the cell population of the immune effector cells prior to the administration.

For example, the acceptable ingredients in the composition are nontoxic to the recipient at the used dose and concentration. The pharmaceutical composition of the present invention includes, but is not limited to, liquid, frozen, and lyophilized compositions.

For example, the pharmaceutically acceptable carrier can include any and all solvents, dispersing mediums, isotonic agents, and absorption retarder that are compatible with the immune effector cells, which may be usually safe and nontoxic, and neither biologically nor otherwise undesired. For example, the pharmaceutically acceptable carrier can include a storage liquid, a cryopreservation liquid, injectable solution at 2° C.-8° C., etc. For instance, the carrier can include the following ingredients: adenosines, sodium chloride, albumin, interleukin-15, angiotensin-II, short peptides and polypeptide compounds in serum-free medium of human umbilical cord mesenchymal stem cells. For example, the carrier can further include Normosol R (Abbott), Plasma-Lyte A (Baxter) injectable solution, 5% aqueous glucose solution or Ringer's lactate solution. For example, the carrier can further include glycine or DMSO.

For example, the composition can include parenteral, transdermal, endoluminal, intra-arterial, intrathecal and/or intranasal administration or direct injection into tissue. For example, the composition can be administered to a patient or a subject via infusion or injection. In some embodiments, the pharmaceutical composition can be administered in different manners, e.g., administered intravenously, intraperitoneally, subcutaneously, intramuscularly, locally or dermally. In some embodiments, the pharmaceutical composition can be administered in an uninterrupted method. The uninterrupted (or continuous) administration can be achieved by a small pump system worn by the patient to measure therapeutic agent flowing into the patient, as described in WO2015/036583.

The present application further provides use of the modified immunologic effector cells of the present application for preparing a CAR-T cell.

The present application further provides use of the modified immunologic effector cells of the present application in manufacture of a drug for allogeneic therapy.

The present application further provides use of the modified immunologic effector cells of the present application in manufacture of a drug for treating tumors.

For example, the tumor includes solid and non-solid tumors. The solid tumors and the non-solid tumors are as described above.

Without being limited by any theory, the following examples are only for illustrating the modified immunologic effector cells, the preparation method and use of the present application, and are not intended to limit the scope of the invention of the present application. The examples do not include a detailed description of traditional methods, such as, methods used for constructing vectors and plasmids, methods of inserting a gene encoding the protein into such vectors and plasmids, or methods of introducing the plasmid into a host cell. Such methods are well known for persons with ordinary skills in the art, and have been described in a plurality of publications, including Sambrook, J., Fritsch, E. F. and Maniais, T. (1989) Molecular Cloning: A Laboratory Manual, 2nd edition, Cold spring Harbor Labora-tory Press.

EXAMPLES

Example 1 Design of Guide RNA

On the website www.ncbi.nlm.nih.gov/, the corresponding gene sequences (as shown in SEQ ID No. 55-63) were searched and downloaded. The gene sequences were opened with Snap Gene software, and sgRNAs could be designed on different exons of the target gene. The sgRNA of CRISPR/Cas9 system used in this example was designed following a non-restrictive principle of 5'-NNN (20)-NGG-3', wherein NGG was called primary spacer adjacent motif (PAM), wherein N represented A, T, C, or G. Since many sgRNAs could be designed on the same exon, and the sgRNA composed of 20 nucleotide sequences may repeatedly occur in the genome, the design and evaluation of sgRNAs were carried out on the website crispr.cos.uni-heidelberg.de. An exon sequence was copied into the website, and then the website designed sgRNAs and performed a prediction evaluation. The higher the evaluation score, the higher the editing efficiency and the lower the off-target risk. The sgRNA with higher score was selected for detection. The sgRNAs targeting the TRAC gene were as shown in SEQ ID No. 1-15; the sgRNAs targeting the HLA-A02 gene were as shown in SEQ ID No. 16-37; the sgRNAs targeting the HLA-A11 gene were as shown in SEQ ID No. 38-46; and the sgRNAs targeting the HLA-A24 gene were as shown in SEQ ID No. 47-54, which were synthesized by Kingsley Biotech.

Example 2 Preparation of CD3Y T Cells (1) Isolation of PBMCs from Peripheral Blood Peripheral blood was collected from healthy volunteer, and diluted with PBS buffer at a ratio of 1:1. To a new 50 ml centrifuge tube was first added ⅓ of the diluted blood volume of cell separation solution (Ficoll®). Then, a dilution of blood cells was added very slowly along the tube wall. The mixture was subject to centrifugation at 800 g at room temperature for 20 min (the centrifuge was set at speed up 1, speed down 0). After centrifugation, the liquid in the centrifuge tube was separated to PBS and serum layer, white blood cell layer, lymphocyte separation fluid and red blood cell layer from top to bottom. The PBS and serum layer were removed; the white blood cell layer was transferred to a new 50 ml centrifuge tube, and PBS was added to a volume of 40 ml to wash the cells. The mixture was subject to centrifugation at 450 g for 10 min. After centrifugation, the supernatant was discarded to obtain peripheral blood mononuclear cells. After resuspension, the cells were counted.

(2) Thawing of Cryopreserved Healthy Human PBMCs

The cryopreserved PBMC cells were thawn in a 37° C. water bath. After complete thawing, the cells were sucked into a 15 ml centrifuge tube containing 10 ml X-VIVO®15 medium containing 10% FBS (purchased from LONZA) and centrifuged at 400 g for 8 min. The supernatant was discarded, and 2 ml X-VIVO®15 medium (containing 10% FBS and a 100 μg/m final concentration of DNase I) was added and incubated at room temperature for 15 min under constant shaking. After incubation, the solution was filtered with 40 μm filter mesh. The cells at the bottom were resuspended in 10 ml PBS buffer, and added onto a filter mesh. After filtration, the filtrate was subject to centrifugation at 400 g for 8 min. After centrifugation, the supernatant was discarded, and the cells were resuspended and counted.

(3) Sorting of $CD3^+$ T Cells

EasySep™ Human T cell sorting kit (purchased from StemCell Technologies, Item No.: 17951) was used to extract T cells in the peripheral blood mononuclear cells (PBMCs). PBMCs were adjusted to a density of $5\times10^7$ cell/ml with a PBS buffer in a range of 0.25-2 ml. First, a cocktail was added and uniformly mixed, and then an isolation cocktail was added at 50 μl/ml. After uniform mixing, the mixture stood at room temperature for 5 min. The RapidSpheres were whirled with a vortex oscillator for 30 seconds, added into the cells at 40 μl/ml, and mixed well. The mixture was supplemented with a buffer to the fold of 2.5 ml, and gently blown up and down for 2-3 times. The mixture was added into cryopreservation tubes with 2.5 ml in each tube. The cryopreservation tubes were placed on a magnetic frame at room temperature for 3 min. The covers of the cryopreservation tubes were gently removed, and the magnetic frames were carefully picked up by holding both ends thereof, and inverted for 2-3 seconds. The cell liquid was poured into a new centrifugation tube at one time. The cells were resuspended in 10-20 ml buffer (depending on the cell counts), and subject to centrifugation at 300 g for 10 min. The supernatant was discarded to obtain CD3YT cells.

(4) Activation of T Cells

An activation reagent was formulated according to the volume ratio of medium: Transact™=99:1. The culture medium was X-VIVO®15 medium (containing 5% FBS, 200 U/ml IL2, 10 ng/ml IL7 and 5 ng/ml IL15), and Transact™ was purchased from Meitianni. T cells were thoroughly resuspended with 1 ml activation reagent (containing 10 μl Transact) per $1\times10^6$ cells, and then incubated in 37° C., 5% CO2 incubator for 3 days.

Example 3 Preparation of Single Knockout Cells

RNP complexes were transferred into activated T cells prepared in Example 2 by electroporation using an electroporation Kit (purchased from LONZA, Item No. V4XXP-3024). The medium (X-VIVO®15 medium+10% FBS+IL2 (200 U/ml)+IL7 (10 ng/ml)+IL15 (5 ng/ml)) was preheated for 30 min in advance. The electrokinetic buffer was formulated at a ratio of Nucleofector Solution:Supplement=82:18. Preparation of RNP complex: the sgRNA sequence of TRAC was sg9 (as shown in SEQ ID No. 1), the sgRNA sequence of HLA-A is HLA-A02 Sg2 (as shown in SEQ ID No. 17) or HLA-A02 Sg5 (as shown in SEQ ID No. 18) or HLA-A11 sg21 (as shown in SEQ ID No. 91) or HLA-A11 Rsg2 (as shown in SEQ ID No. 92). 20 μg sgRNA was first added into a PCR tube (RNA enzyme free), and then 10 μg Cas9 protein (purchased from thermo, Item No. A36499) was added. After mixing well, the mixture was incubated for 12 min. The activated T cells cultured in Example 2 were counted, and subject to centrifugation at 300 g for 8 min. The supernatant was discarded, and PBS was added to resuspend the cells. 1E7 cells were taken for additional centrifugation at 300 g for 8 min. The supernatant was discarded, and the cells were resuspended in 100 μl of the prepared electroporation buffer. The incubated RNP complexes were added to the above cell suspension, mixed gently, and then the mixture was gently transferred to the electrofection cup. The electrofection cup was placed on the Lonza-4D electric rotating instrument, and the EO-115 electric rotating program was selected for electric rotating. Pre-heated medium was added into the electrofection cup, and then the cells were transferred into the preheated medium in the well plate with a supporting pipette, and then cultured in a 37° C., 5% C02 incubator.

Example 4 Comparison of Methods for Detecting the Gene Knockout Efficiency (1) Detection of Sanger Sequencing The cells were counted, and 3~5×$10^4$ cells were subject to centrifugation at 2000 r/min for 5 min. The supernatant was discarded as much as possible, and 20 μl DE lysing solution was added onto each tube. Lysed cells were added into the PCR tube, centrifuged instantaneously and then placed into the PCR apparatus with the following conditions: 65° C. for 30 min, 4° C. for 30 s, 95° C. for 2 min and 16° C. for infinite time. PCR was performed by using primer pairs TRAC-For/TRAC-Rev or HLA-A For/HLA-A Rev with the cleavage products as templates. The sequence of PCR primers was as shown in SEQ ID NO. 66-81. The PCR products were sent to Jin Weizhi for Sanger sequencing. After getting the Sanger sequencing results, the editing site and the editing efficiency were predicted with the EditR editor on the website: moriaritylab.shinyapps.io/editr_v10/.

(2) Detection of TA Clone Sequencing

AxyPrep™ PCR product cleaning kit (purchased from AXYGEN) was used to purify the PCR product. Then the purified PCR product was added with sticky end by DNA A-Tailing Kit (purchased from TaKaRa). The product was linked to T vector (pMDTM19-T Vector Cloning Kit, purchased from TaKaRa) by a DNA Ligation Kit Ver2.1 (purchased from TaKaRa), and the ligated product was transformed into competent cells (DH5 alpha). Then, it was coated on an LB plate containing ampicillin resistance and cultured in 37° C. incubator for about 12 hours. Subsequently, a single colony was picked, and the single colony liquid was sent to Jin Weizhi for sequencing. Knockout efficiency=Mutatant Clone Number/Total Clone Number.

(3) Cell Counting by Flow Cytometry

10E5 to 10E8 cells were subject to centrifugation at 2000 rpm for 5 min. The supernatant was discarded, and 100 μl PBS buffer was added to each tube for resuspending the cells. Then, 5 μl anti-human AB TCR-APC (purchased from eBioscience) antibody and 5 μl HLA-A02 Monoclonal Antibody (BB7.2), APC, eBioscience™ (purchased from invitrogen) antibody were mixed well and incubated at room temperature for 10 min. After centrifugation at 2000 rpm for 5 min, followed by washing with PBS buffer 2 times, the cells were resuspended and detected by using BD FACSAria™ flow cytometer to give the expression positive rates of the TCR and HLA-A02 on the cell surface. Knockout efficiency=(A−B)/A×100%; A is the expression positive rate of the control group; and B is the expression positive rate of the knockout group.

Figure 2:
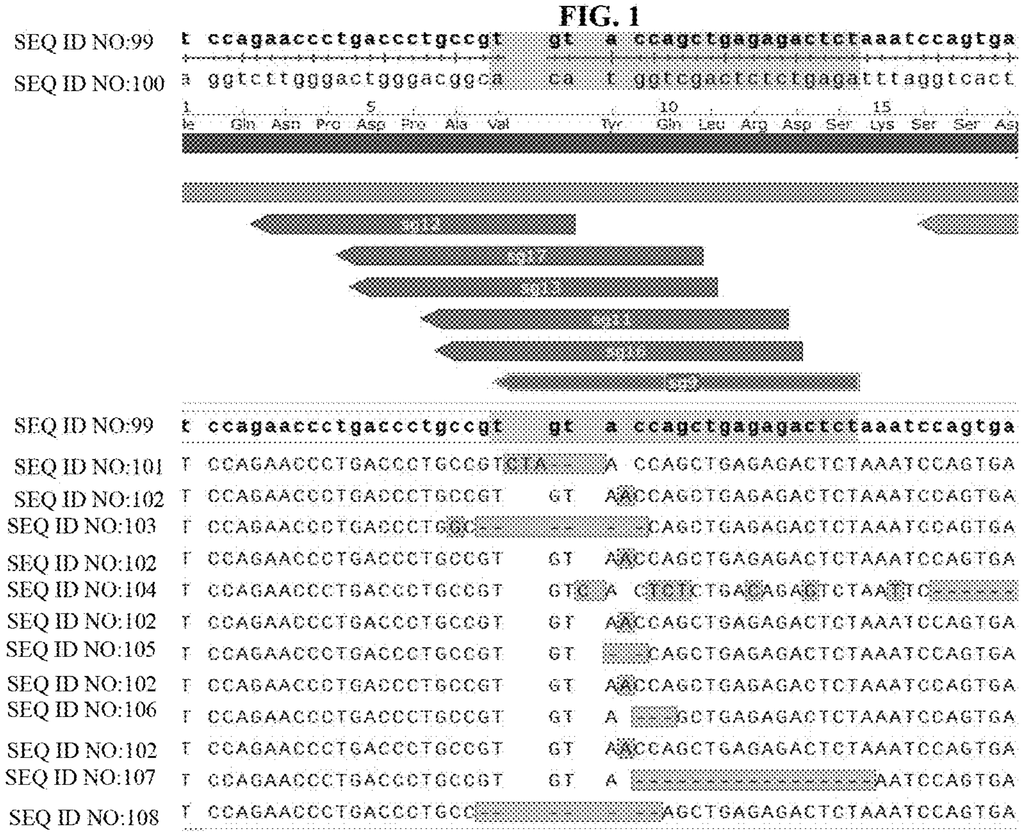
FIG. 2 shows the TA clone detection results of the TRAC gene of the present application after Sg9RNA editing.
Figure 3A:
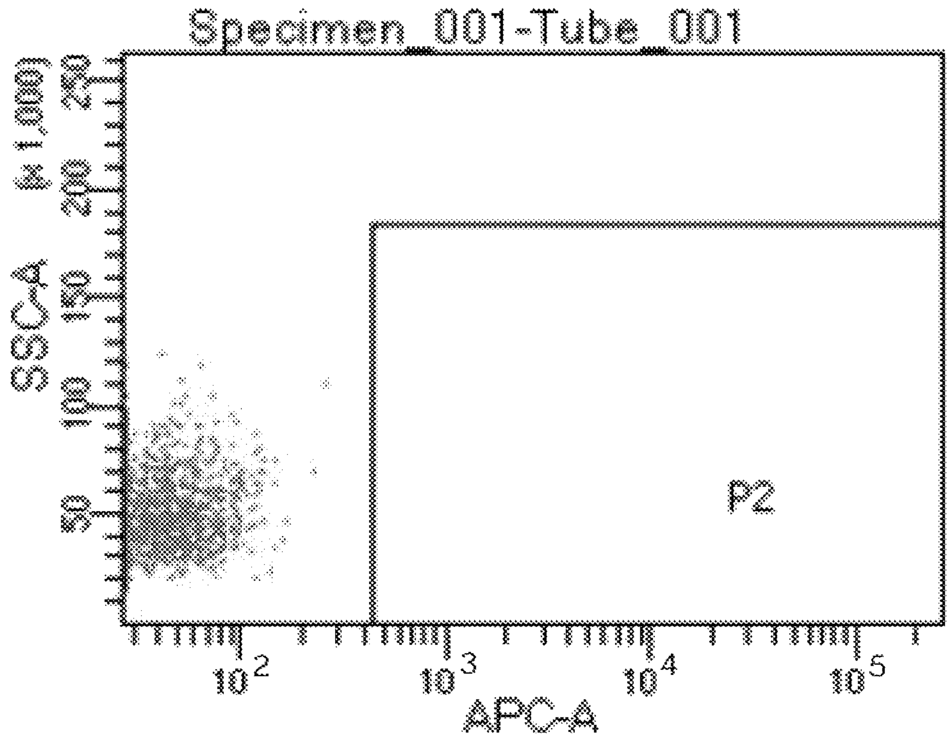
FIG. 3A, FIG. 3B, and FIG. 3*c* show the flow cytometric results of the TRAC gene of the present application after Sg9RNA editing.
Figure 3B:
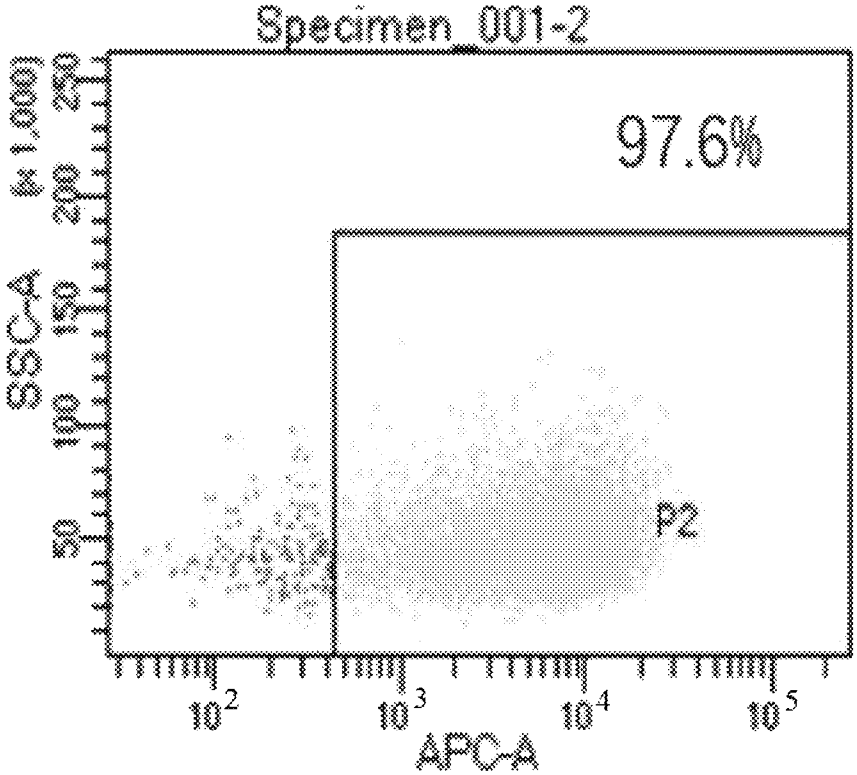
Figure 3C:
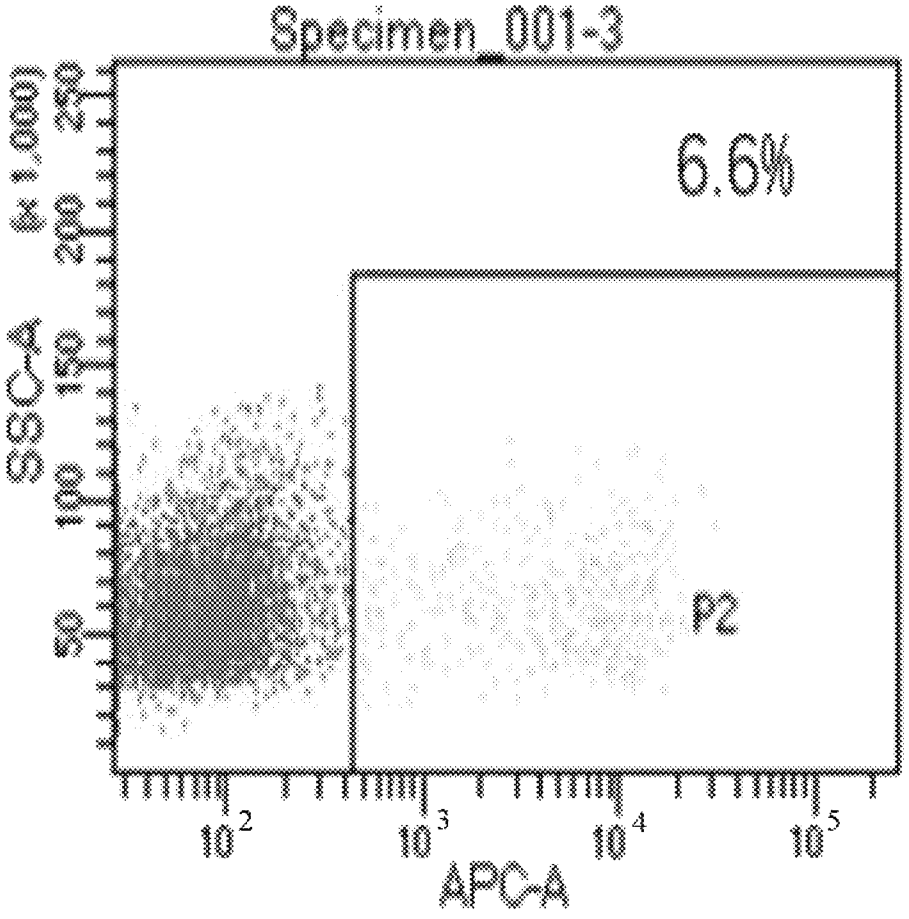

The three measured results of single knockout TRAC were shown in FIGS. 1-3, and the calculated results of knockout efficiency were shown in Table 1. The results of three detection methods are substantially the same, and in the subsequent experiments, the editing efficiency was merely detected via Sanger sequencing.

TABLE 1

Results of methods for detecting knockout efficiency of gene

| Target gene | sgRNA | Detecting method | Knockout efficiency % |
|---|---|---|---|
| TRAC | Sg9 | Sanger sequencing | 90 |
| | | TA clone sequencing | 95 |
| | | Flow cytometry | 93 |

Figure 4:
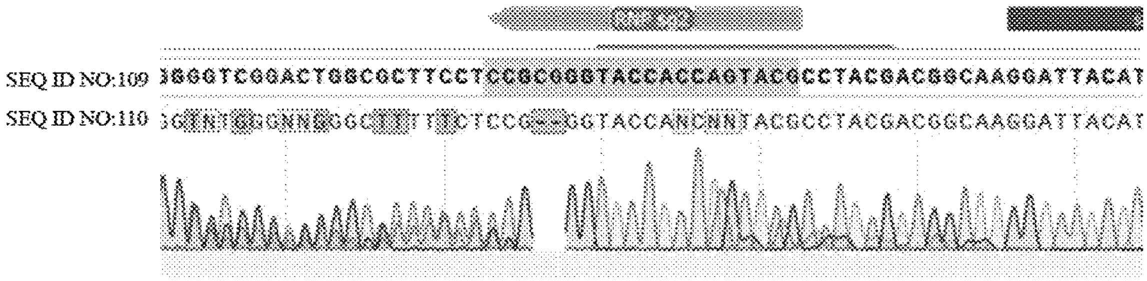
FIG. 4 shows the Sanger sequencing results of the HLA-A02 gene of the present application after Sg2RNA editing.
Figure 5:
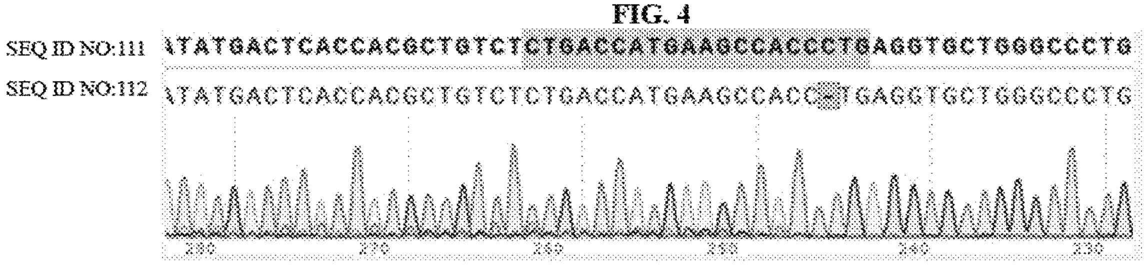
FIG. 5 shows the Sanger sequencing results of the HLA-A02 gene of the present application after Sg5RNA editing.
Figure 6:
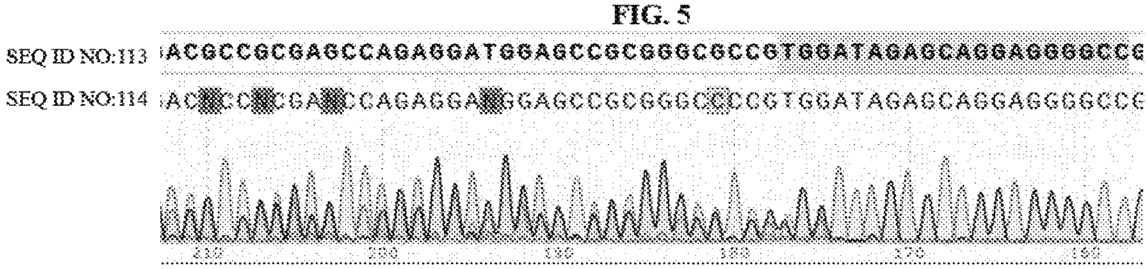
FIG. 6 shows the Sanger sequencing results of the HLA-A11 gene of the present application after Sg10-3RNA editing.
Figure 7:
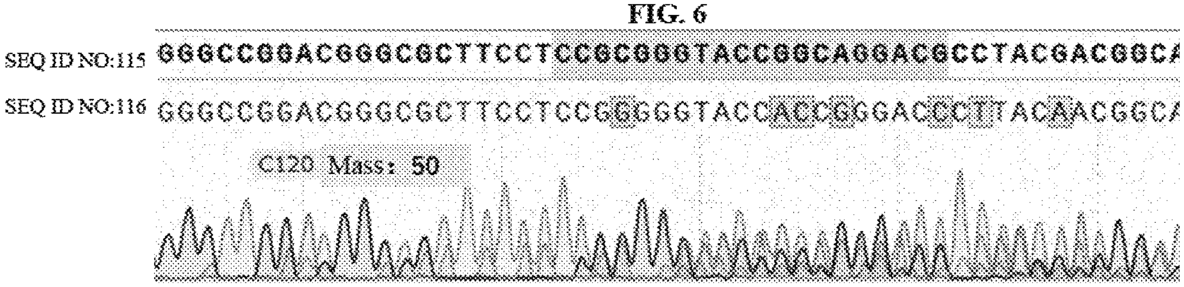
FIG. 7 shows the Sanger sequencing results of the HLA-A11 gene of the present application after Sg21RNA editing.

The results of Sanger sequencing against HLA-A02 gene editing were shown in FIGS. 4-5 with the editing efficiency of 90%; and the results of Sanger sequencing against HLA-A11 gene editing were shown in FIGS. 6-7.

Example 5 Preparation of T Cells in which the TRAC Gene and the HLA-A Gene were Dual Knockout RNP complexes were transferred into activated T cells prepared in Example 2 by electroporation using an electroporation kit (purchased from Lonza, Article No.: V4XXP-3024). The medium was preheated in the well plate for 30 min in advance (X-VIV015 medium+10% FBS+IL2 (200 U/ml)+IL7 (10 ng/ml)+IL15 (5 ng/ml)). The electrokinetic buffer was formulated in a ratio of Nucleofector Solution: Supplement=82:18. Preparation of RNP complex: 20 μg TRAC sgRNA (TRAC Sg9), 20 μg HLA-A sgRNA (HLA-A02 Sg2 or HLA-A02 Sg5 or HLA-A11 sg21 or sgRNAs targeting HLA-A*24:02:01, HLA-A*30:01:01:01, HLA-A*33:01:01:01, HLA-A*03:01:01:01, HLA-A*01:01:01:01 or HLA-A*26:01:01:01) were added into PCRs (RNA-free), respectively, and 10 μg Cas9 protein (purchased from thermo, Item No. A36499) was added to each tube. After mixing well gently, the mixtures were incubated at room temperature for 12 min. The activated T cells cultured in Example 2 were counted, and centrifuged at 300 g for 8 min. The supernatant was discarded. PBS was added to resuspend cells. 1E7 cells were centrifuged at 300 g for additional 8 min. The supernatant was discarded, and the cells were resuspended in 100 μl prepared electrofection buffer. The incubated RNP complexes of TRAC and HLA-A were added into the above cell suspensions and mixed gently. Then, the mixture was gently transferred to the electrofection cup. The electrofection cup was placed on the Lonza-4D electric rotating instrument, and the EO-115 electric rotating program was selected for electric rotating. Pre-heated medium was added into the electrofection cup, and then the cells were transferred into the preheated medium in the well plate with a supporting pipette, and then cultured in a 37° C., 5% $CO_2$ incubator.

Figure 8A:
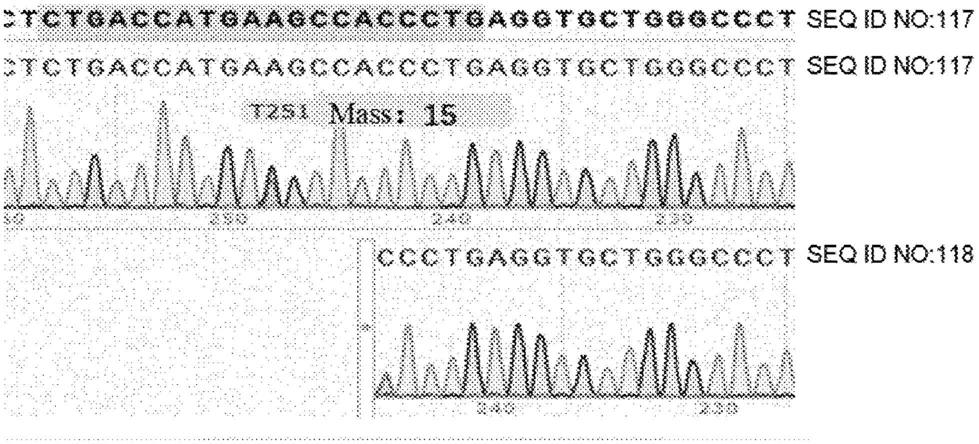
FIGS. 8A-8B show the results of simultaneous knockout of HLA-A02 and TRAC in the modified immune effector cells of the present application.
Figure 8B:
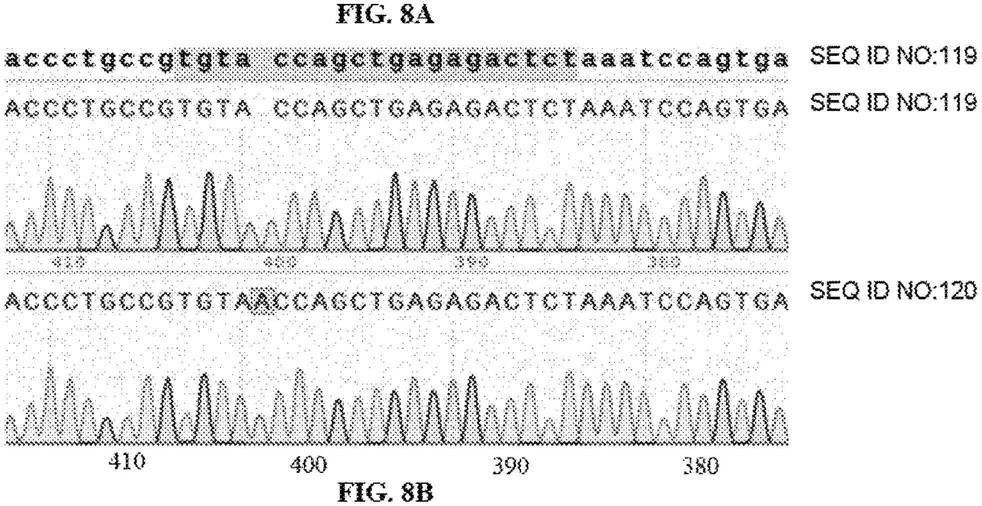
Figure 9A:
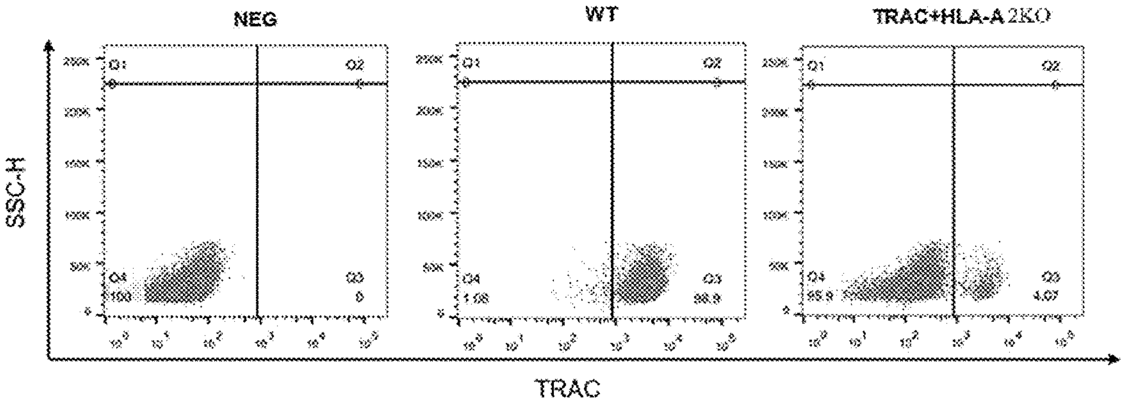
FIGS. 9A-9B show the protein levels of HLA-A02 and TRAC in the modified immune effector cells of the present application.
Figure 9B:
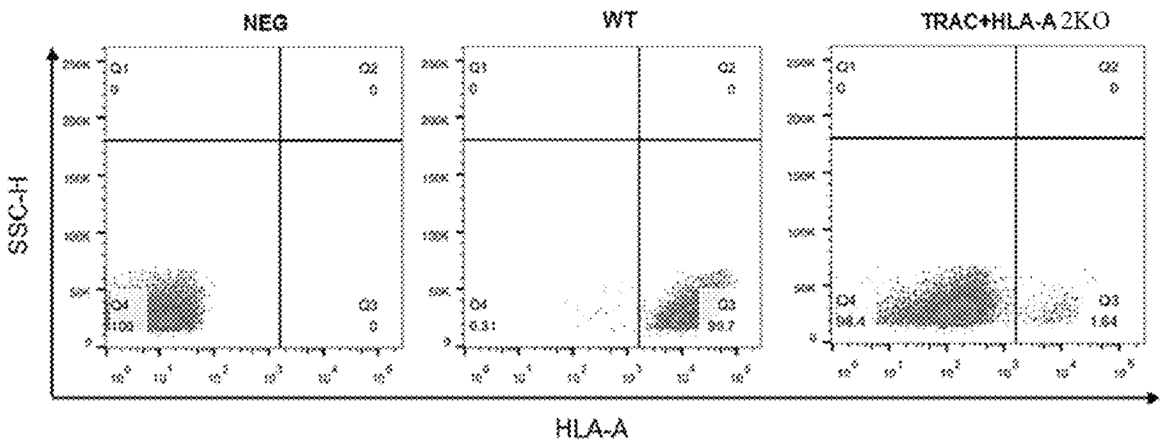
Figure 10A:
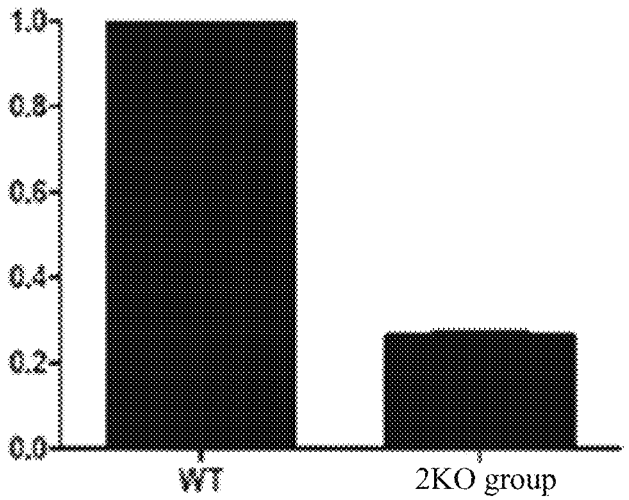
FIGS. 10A-10D show the mRNA levels of TRAC, HLA-A, B2M and CIITA in the modified immune effector cells of the present application.
Figure 10B:
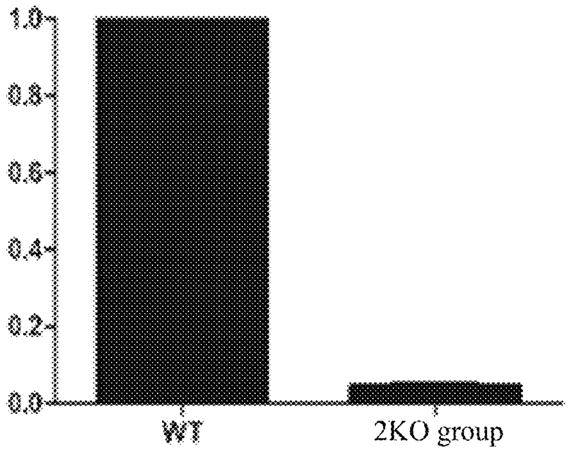
Figure 10C:
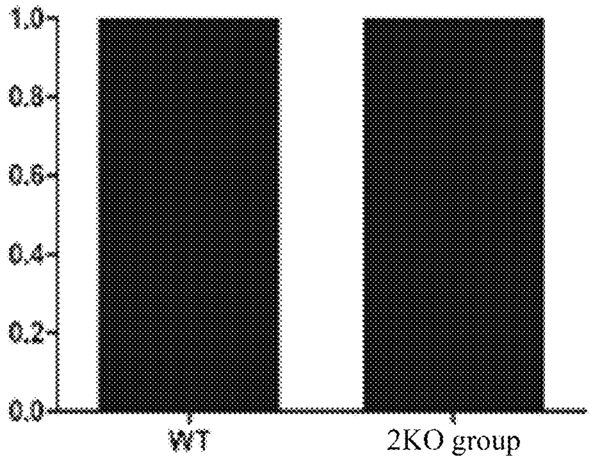
Figure 10D:
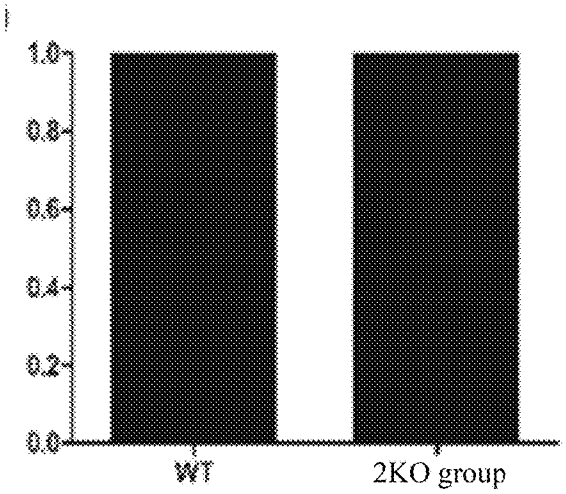

The dual knockout efficiency was detected via sequencing to obtain the TRAC-negative, HLA-A-negative T cells in which the dual knockout efficiency was not less than 80%. The results were shown in FIGS. 8-9, wherein, FIG. 8A showed the results of knockout of HLA-A02 with HLA-A02 Sg5, wherein the upper row showed the results of the control group (that is, no knockout was performed with HLA-A02 Sg5); and the lower row showed the results of dual knockout of HLA-A02 and TRAC; wherein, FIG. 8B showed the results of knockout of TRAC with TRAC Sg9, wherein the upper row showed the results of the control group (that is, no knockout was performed with TRAC Sg9), and the lower row showed the results of dual knockout of HLA-A02 and TRAC. FIGS. 9A-9B showed the knockout status of HLA-A02 and TRAC in terms of protein levels, in which NEG referred to the negative control, WT referred to the status with no knockout, and TRAC+HLA-A dual knockout referred to the results of dual knockout of HLA-A02 and TRAC.

Example 6 Difference of the Expression of TRAC Gene, HLA-A Gene, B2M Gene and CITTA Gene in Dual Knockout T Cells from the Expression of the Corresponding Genes in the Corresponding Cells (1) The activated T cells prepared in Example 2 were divided into two groups: one was used as control, and the other was used to prepare T cells in which the TRAC gene and the HLA-A gene were dual knockout in accordance with the method of Example 5, and subject to Sanger sequencing in accordance with the method of step (1) of Example 4. In accordance with the sequencing results, the cells in which the TRAC gene and the HLA-A gene were dual knockout. The prepared dual knockout T cells were incubated with the corresponding TRAC and HLA-A antibodies, and sorted by flow cytometry or magnetic beads to give dual knockout cell strains.

(2) The changes of mRNA expression levels of dual knockout T cells and the control group were detected. An RNA extract kit (purchased from QIAGEN, Article No.: 74004) was used to extract the RNA. The RNA was subject to reverse transcription with a reverse transcription kit (purchased from Applied Biosystems, Article No.: 4368814) to give cDNA, which was used as a template for quantitative PCR detection.

(3) The changes of protein expression levels of dual knockout T cells and the control group were detected. Total protein extract reagent (purchased from Thermo Scientific, Article No.: 87787) was used to extract protein. The expression levels of protein were detected by Western Blot method or flow cytometric method. The used antibodies were TRAC antibody (purchased from eBioscience, Article No.: 17-9986-42), HLA-A antibody (purchased from Merck, Article No.: 17-9876-41), B2M antibody (purchased from Invitrogen, Article No.: A15770) and CIITA antibody (purchased from OnGene, Article No.: CF812200), respectively.

The Sanger sequencing showed that in the dual knockout T cells, the nucleotide sequences of TRAC and/or HLA-A genes were changed as compared with the control group. The quantitative PCR showed that in the dual knockout T cells, the expression levels of mRNA of TRAC and/or HLA-A genes were down-regulated, while the expression levels of mRNA of B2M and/or CIITA genes were not down-regulated. The results of FACS and Western Blot shown that in the dual knockout T cells, the expression levels of protein were down-regulated, while the expression levels of protein of B2M and/or CIITA were not down-regulated.

Figure 11A:
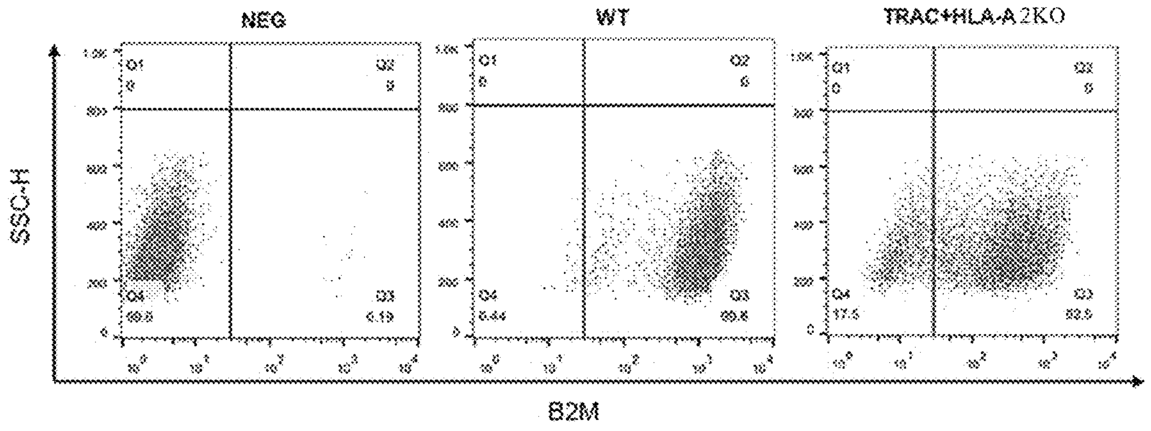
FIGS. 11A-11B show the protein levels of B2M and CIITA in the modified immune effector cells of the present application.
Figure 11B:
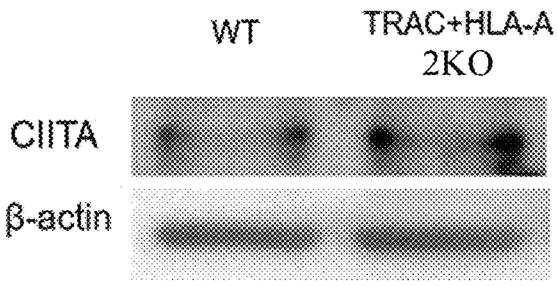

The results were shown in FIGS. 10-11, wherein, FIG. 10 showed the measurement of mRNA level of the gene expression, wherein FIGS. 10A-10D showed the mRNA levels of TRAC, HLA-A, B2M and CIITA, respectively; wherein WT referred to the status with no knockout, and the dual knockout group referred to the results of T cells in which the TRAC gene and the HLA-A gene were dual knockout. FIG. 11 showed the measurement of protein levels of the gene expression, wherein FIGS. 11A-11B showed the protein expression levels of B2M and CIITA, respectively; wherein NEG referred to the negative control, WT referred to the status with no knockout, and TRAC+HLA-A dual knockout referred to the results of T cells in which the TRAC gene and the HLA-A gene were dual knockout.

Example 7 Preparation of T Cells in which the TRAC Gene, the HLA-A/B2M Gene and the CITTA Gene were Triple Knockout, and Verification of the Change of Expression of the Corresponding Three Genes Therein (1) The control group and cells in which the TRAC gene, the HLA-A gene, and the CIITA gene were triple knockout, as well as cells in which the TRAC gene, the B2M gene, and the CIITA gene were triple knockout were prepared in accordance with the methods of step (1) of Example 6.

(2) The change of protein expression levels was detected in accordance with the method of step (3) of Example 6 by FACS and Western Blot methods.

In relation to the cells of the control group, the protein expression levels of TRAC, HLA-A and CIITA genes in T cells in which the TRAC gene, the HLA-A gene, and the CIITA gene were triple knockout were down-regulated. In relation to the cells of the control group, the protein expression levels of TRAC, HLA-A and CIITA genes in TRAC, B2M and CIITA triple knockout T cells were down-regulated.

(3) TRAC (purchased from eBioscience, Article No.: 17-9986-42), HLA-A (purchased from Merck, Article No.: 17-9876-41), B2M (purchased from Invitrogen, Article No.: A15770) antibodies were used to detect the knockout efficiency of the dual knockout cells of Example 6 and the two types of triple knockout cells in this example by flow cytometry. The results showed that in terms of the efficiency of multiple gene knockout at the single cell level, dual knockout was significantly better than triple knockout.

Figure 12A:
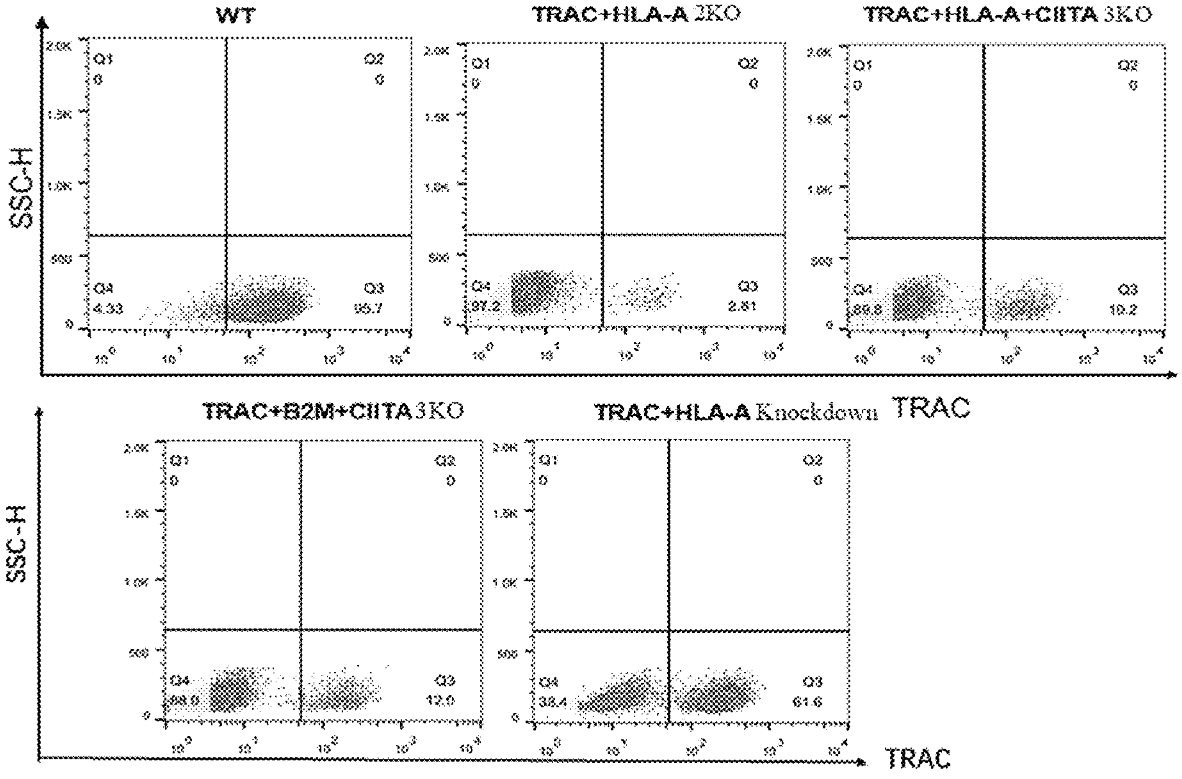
FIGS. 12A-12D show the protein levels of TRAC, HLA-A, B2M and CIITA in the modified immune effector cells of the present application.
Figure 12B:
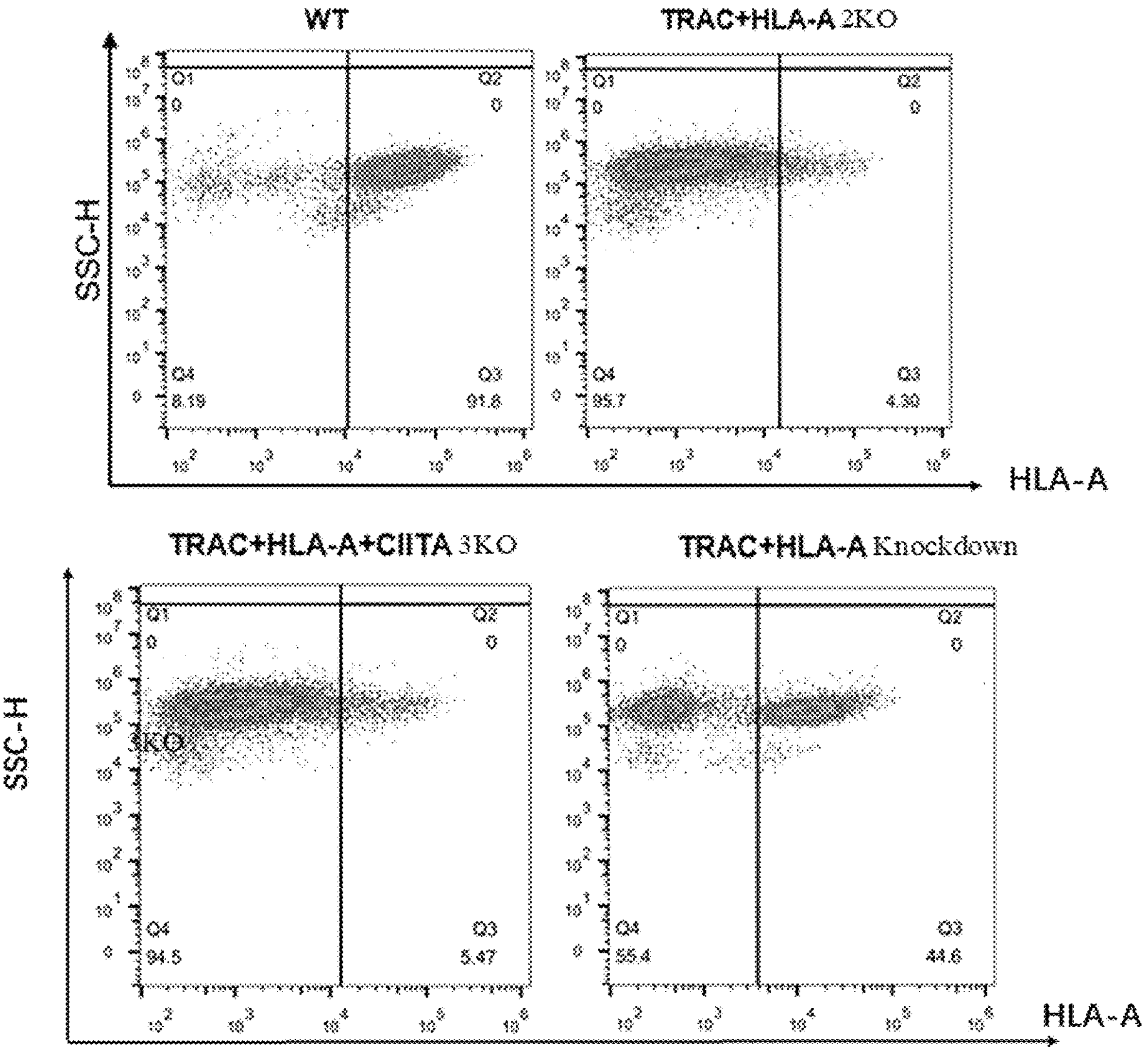
Figure 12C:
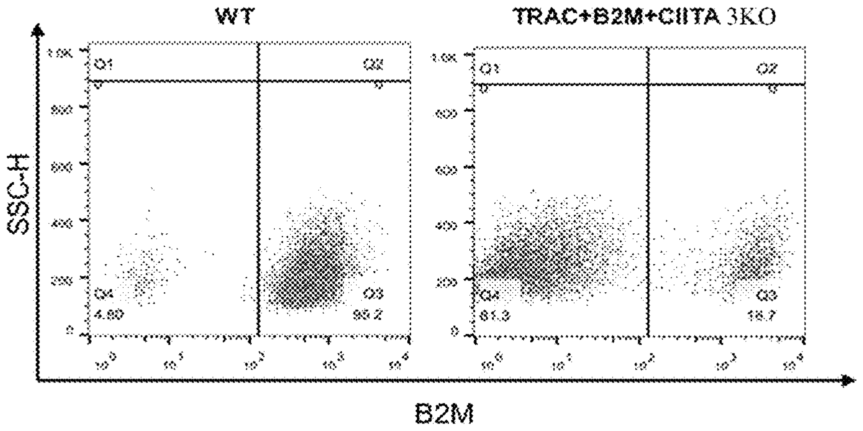
Figure 12D:
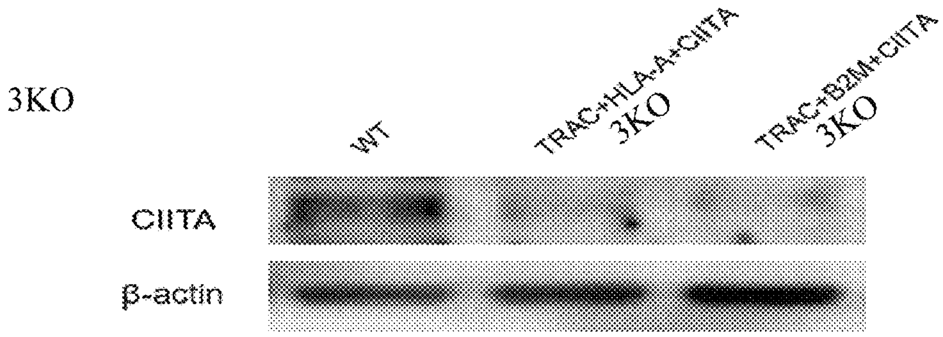

The results were shown in FIGS. 12A-12D, wherein FIGS. 12A-12C sequentially showed the knockout status of TRAC, HLA-A and B2M in terms of protein levels; wherein, WT referred to the status with no knockout, TRAC+HLA-A dual knockout referred to the results of T cells in which the TRAC gene and the HLA-A gene were dual knockout; TRAC+HLA-A+CIITA triple knockout referred to the results of T cells in which the TRAC gene, the HLA-A gene, and the CIITA gene were triple knockout; wherein TRAC+B2M+CIITA triple knockout referred to the results of T cells in which the B2M gene, the CIITA gene, and the TRAC gene were triple knockout; TRAC+HLA-A knockdown referred to the results of T cells in which the TRAC gene and the HLA-A gene prepared in Example 9 were knockdown. FIG. 12D showed the knockout status of CIITA in terms of protein level.

The results of FIG. 12 showed that as compared with the WT control group, the protein levels of TRAC, HLA-A, CIITA and B2M were down-regulated. At the same time, as compared with TRAC+HLA-A+CIITA triple knockout or TRAC+B2M+CIITA triple knockout, the knockout efficiency of TRAC+HLA-A dual knockout was higher.

Example 8 Design of Antisense RNA Sequence

Through the database www.ncbi.nlm.nih.gov/ or www.ensembl.org/, the transcription RNA sequences (as shown in SEQ ID NO. 82-90) of the corresponding genes (TRAC gene and HLA-A gene) were obtained, and siRNA was designed by reference to the following principles:

Sequences of 50-100 nucleotides downstream of the start codon and 100 nucleotides upstream of the stop codon were avoided as possible. Sequences with less than 30 nucleotides in length were selected. Four or greater consecutive identical bases were avoided. Intron regions were avoided. Repetitive sequences were avoided. Single nucleotide polymorphism (SNP) sites were avoided. Sequences have a GC content ranging 30% to 60%. Sequence patterns AA (N<sub >19), NA (N<sub >21) or NAR (N<sub >17) YNN were preferentially selected, wherein A was adenylate; T was thymosine; R was adenylate or guanosine (purine); Y was thymidine or cytidine (pyrimidine); N was adenylate, thymidine, guanosine or cytidine. The selected sequences were subject to comparison and analysis of sequence homology, so as to avoid the significant homology between antisense RNA and other genes or sequences and the resulting off-target effect. The homology analysis was performed by means of NCBI Blast tool: Nucleotide-nucleotide BLAST (blastn), UCSC Blat tool or Ensembl Blast.

The designed antisense RNA sequence included: HLA-A-homo-551 (which included the nucleotide sequence as shown in SEQ ID NO. 93); HLA-A-homo-NEG (which included the nucleotide sequence as shown in SEQ ID NO. 94); TRAC-homo-375 (which included the nucleotide sequence as shown in SEQ ID NO. 95); and TRAC-homo-NEG (which included the nucleotide sequence as shown in SEQ ID NO. 96).

Figure 13A:
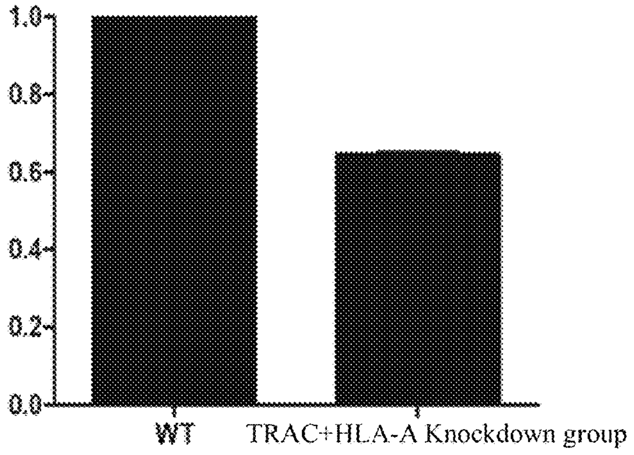
FIGS. 13A-13B show the knockout status of TRAC and HLA-A at mRNA levels in the modified immune effector cells of the present application.
Figure 13B:
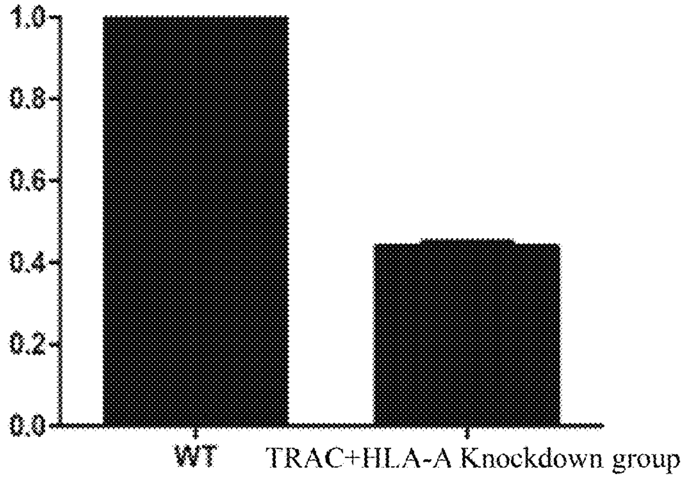

Example 9 Preparation of T Cells in which the TRAC Gene and the HLA-A Gene were Knockdown The antisense RNAs designed in Example 8 were used to perform double gene knockdown. A lentivirus including the antisense RNA sequences of TRAC gene and HLA-A gene was prepared (Gemma). CD3+ T cells were prepared in accordance with the method of Example 2 (Day D0), and activated with CD3/CD28 antibody-bearing magnetic beads. The activated T cells were transfected with the lentiviruses bearing the antisense RNA sequences of TRAC gene and HLA-A gene (SEQ ID NO. 95 and SEQ ID NO. 93) (Day D1), washed to remove the lentivirus vectors on Day D2, and continued to culture until Day D5. The cultured T cells cultured to Day D5 were collected, and detected by quantitative PCR or Western Blot and the like for the knockdown efficiency. The resultant T cells were labelled with the corresponding TRAC and HLA-A antibodies, and sorted by flow cytometric sorting or magnetic bead sorting to give T cells in which the TRAC gene and the HLA-A gene were knockdown. The results showed that in the TRAC and HLA-A gene knockdown group, the expression levels of mRNA and protein of TRAC and HLA-A were both down-regulated, wherein, FIGS. 13A-13B sequentially showed the knockout status of TRAC and HLA-A in terms of mRNA levels; wherein, WT referred to the status with no knockout, TRAC+HLA-A dual knockout referred to the results of T cells in which the TRAC gene and the HLA-A gene were dual knockout. Of those, for the knockout level of TRAC and HLA-A in terms of protein levels, please refer to the results of FIG. 12.

Example 10 Difference of Activities of Different T Cells

T cells in which no gene was knockout, 2 or 3 genes were knockout, and 2 genes were knockdown in Examples 2, 5, 7, and 9 were prepared, and compared for their activities. The cells of individual group were counted, and $1*10^6$ cells were inoculated into a 24-well plate. In each well, PHA (0.3 μg/ml) (ionomycin+) or 5 ng/ml PMA and 50 ng/ml ionomycin were added into the cells, which were cultured for additional 5 hours, and then detected by CD69 (early activated) (purchased from BD Biosciences, Article No.: FN50), CD137 (later) (purchased from BD Biosciences, Article No.: 4B4-1) antibodies via flow cytometry for the activated status of the cells. The results showed that the activities of dual knockout and 2 gene knockdown T cells were better than triple knockout cells.

Figure 14A:
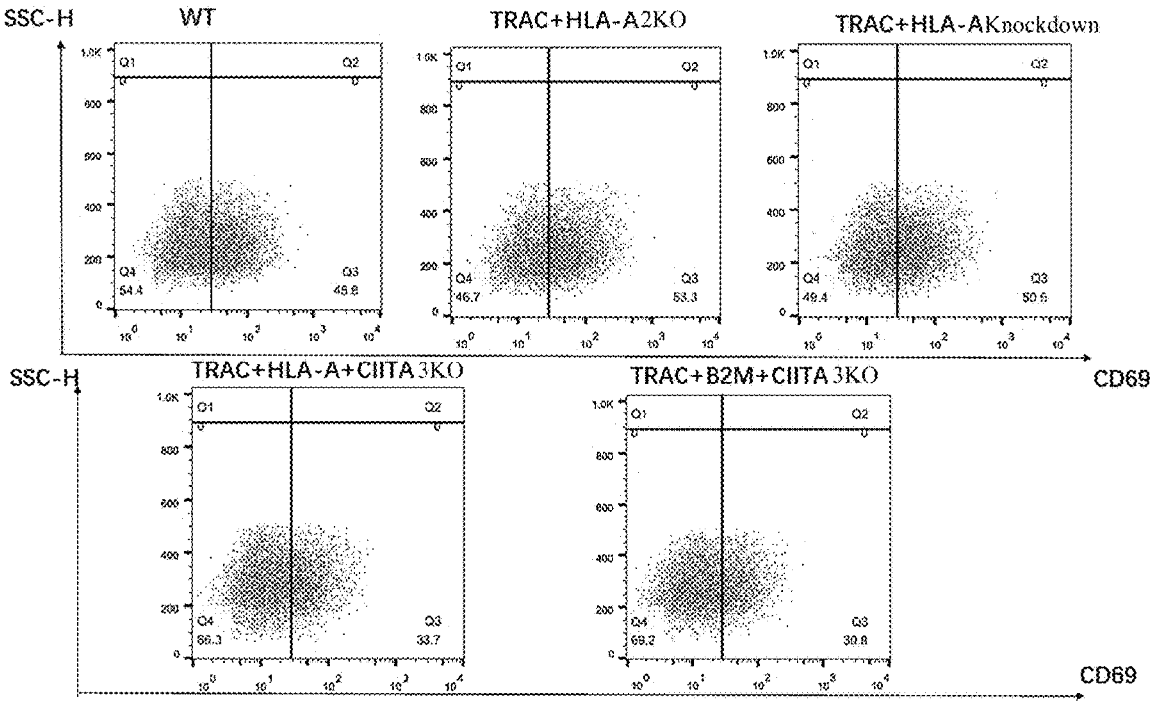
FIGS. 14A-14B show the protein levels of CD69 and CD137 in the modified immune effector cells of the present application.
Figure 14B:
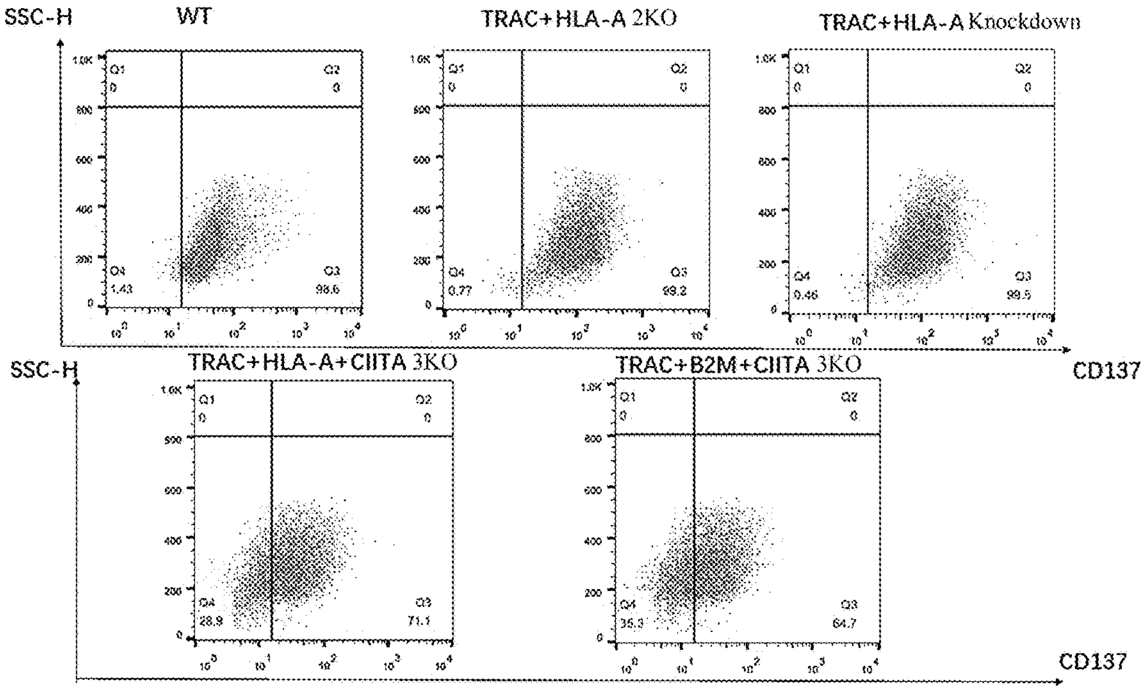

The expression status of CD69 and CD137 in terms of protein levels were shown in FIGS. 14A-14B, respectively, wherein, WT referred to the status with no knockout, TRAC+HLA-A dual knockout referred to the results of T cells in which the TRAC gene and the HLA-A gene were dual knockout; TRAC+HLA-A+CIITA triple knockout referred to the results of T cells in which the TRAC gene, the HLA-A gene, and the CIITA gene were triple knockout; wherein TRAC+B2M+CIITA triple knockout referred to the results of T cells in which the B2M gene, the CIITA gene, and the TRAC gene were triple knockout; and TRAC+HLA-A knockdown referred to the results of T cells in which the TRAC gene and the HLA-A gene prepared in Example 9 were knockdown.

Example 11 Difference of Reactivity of Different T Cells on Allogenic NK Cells T cells in which no gene was knockout, 2 or 3 genes were knockout, and 2 genes were knockdown in Examples 2, 5, 7 and 9 were labelled with CFSE (invitrogen, C34554). The cells were counted, and $1*10^6$ cells of each group were co-cultured with NK cells (NK92MI) at a ratio of 1:1, respectively. After 24 hours, the co-cultured cells were collected, and detected via flow cytometry for the ratio of CFSE positive cells in the mixed cells.

Figure 15:
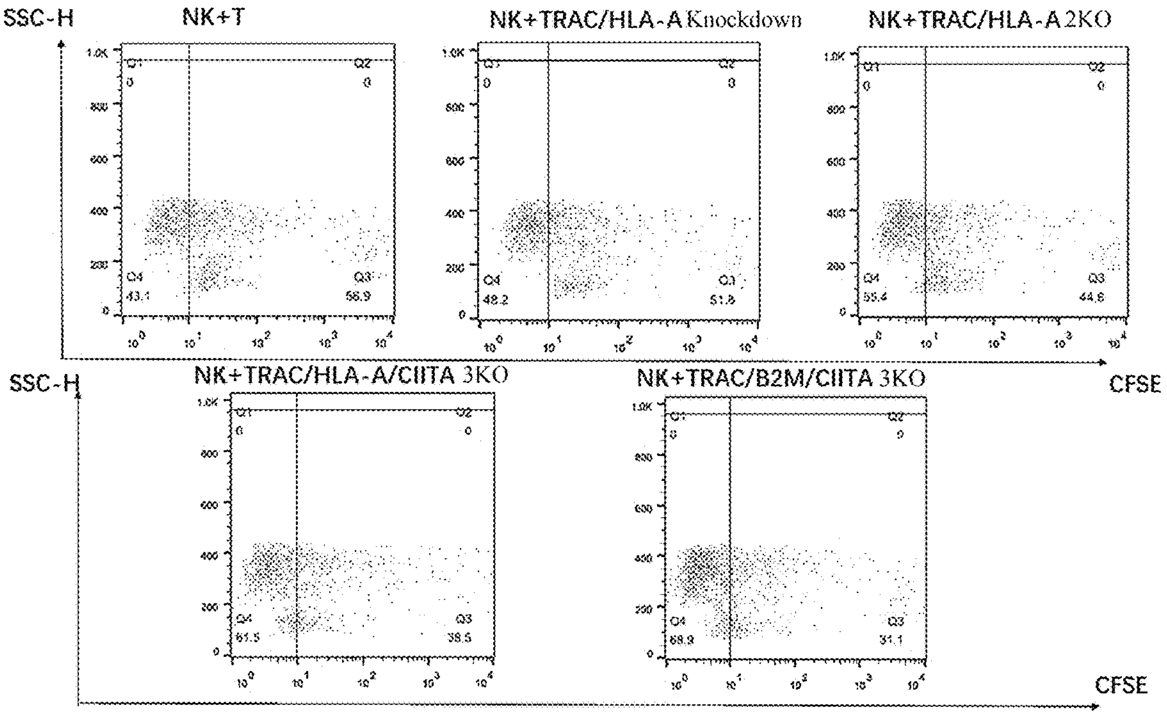
FIG. 15 shows the co-culture status of the modified immune effector cells of the present application and NK cells

The results showed that the killing toxicity of NK cells on the dual gene knockout, dual knockdown T cells was lower than that on triple knockout T cells. The results were shown in FIG. 15, wherein, NK+T referred to the status that the NK cells were co-cultured with T cells with no knockout; NK+TRAC+HLA-A knockdown referred to the status that the NK cells were co-cultured with T cells in which the TRAC gene and the HLA-A gene prepared in Example 9 were knockdown; NK+TRAC+HLA-A dual gene knockout referred to the status that the NK cells were co-cultured with T cells in which the TRAC gene and the HLA-A gene were dual knockout; NK+TRAC+HLA-A+CIITA triple gene knockout referred to the status that the NK cells were co-cultured with T cells in which the TRAC gene, the HLA-A gene, and the CIITA gene were triple knockout; and NK+TRAC+B2M+CIITA triple gene knockout referred to the status that the NK cells were co-cultured with T cells in which the B2M gene, the CIITA gene, and the TRAC gene were triple knockout.

Example 12 Difference of Allogenic Rejections of Different T Cells

Peripheral blood originated from donor 1 was used to prepare T cells in which no gene was knockout, 2 or 3 genes were knockout, and 2 genes were knockdown in Examples 2, 5, 7 and 9. Peripheral blood originated from donor 2 was used to prepare $CD3^+$ T cells. Various groups of cells prepared with peripheral blood from donor 1 were mixed with $CD3^+$ T cells prepared with peripheral blood from donor 2 in accordance with Example 2 at a ratio of 1:1. After 24 hours, the mixed system of cells was detected for the expression level of IFN-γ. The results showed that the expression level of IFN-γ in dual knockout T cell group was lower than that in triple knockout T cell group.

Figure 16:
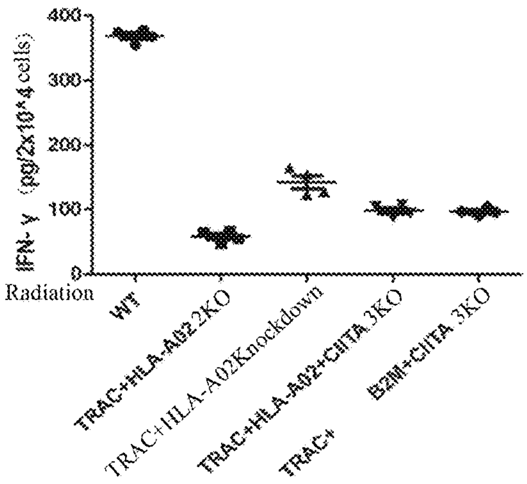
FIG. 16 shows the level of IFN-γ expressed in the modified immune effector cells of the present application.

The results are shown in FIG. 16, wherein WT referred to the status with no knockout; TRAC+HLA-A dual knockout referred to the results of T cells in which the TRAC gene and the HLA-A gene were dual knockout; TRAC+HLA-A+CIITA triple knockout referred to the results of T cells in which the TRAC gene, the HLA-A gene and the CIITA gene were triple knockout; wherein TRAC+B2M+CIITA triple knockout referred to the results of T cells in which the B2M gene, the HLA-A gene and the TRAC gene were triple knockout; and TRAC+HLA-A knockdown referred to the results of T cells in which the TRAC gene and the HLA-A gene prepared in accordance with Example 9 were knockdown.

Example 13 Preparation of CAR-T Cells in which the TRAC Gene and the HLA-A Gene were Dual Knockout, CAR-T Cells in which the TRAC Gene, the HLA-A Gene, and the CIITA Gene were Triple Knockout, and CAR-T Cells in which the TRAC Gene, the B2M Gene and the CIITA Gene were Knockout (1) CD3+ T cells were prepared in accordance with the method of Example 2 (Day D0), and activated with CD3/CD28 antibody-bearing magnetic beads. The activated T cells were transfected with lentiviruses (lentiviruses containing CD19-CAR, CD20-CAR or BCMA-CAR, etc.) on D1, washed to remove the lentivirus vectors on D2, sorted for CAR-positive T cells at D3, and continued to culture until Day D5.
(2) The CAR-T cells on D5 were selected as initial cells, and used to prepare cells in which the TRAC gene and the HLA-A gene were dual knockout, CAR-T cells in which the TRAC gene, the HLA-A gene and the CIITA gene were triple knockout, and CAR-T cells in which the TRAC gene, the B2M gene and the CIITA gene were triple knockout in accordance with the methods of Example 5 and Example 7, respectively.
(3) By detection via flow cytometry, dual knockout and triple knockout CAR-T cells were obtained, wherein the yield of dual knockout CAR-T cells were higher than that of triple knockout CAR-T cells.

Figure 17A:
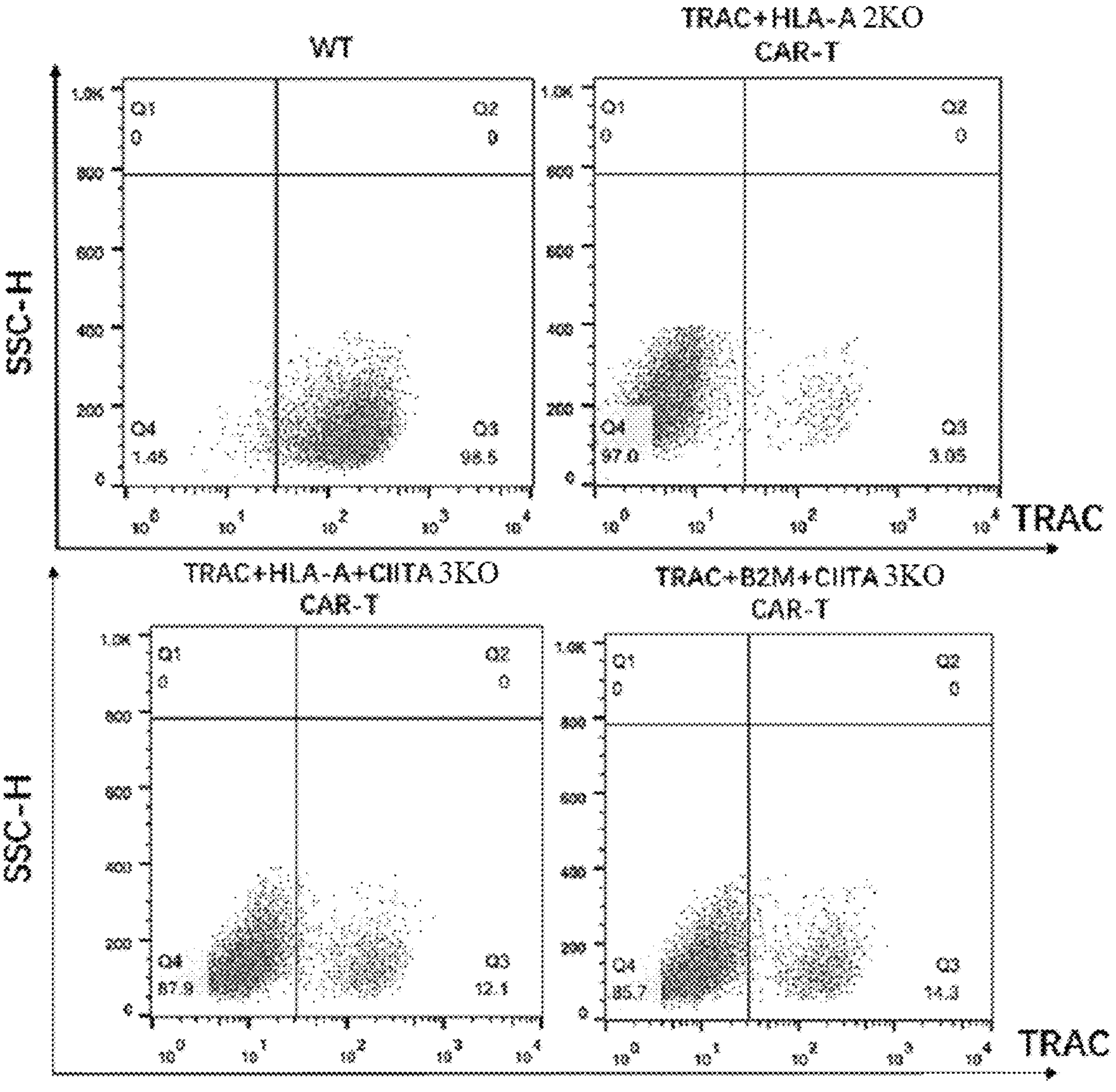
FIGS. 17A-17D show the protein levels of TRAC, HLA-A, B2M and CIITA in the modified immune effector cells of the present application.
Figure 17B:
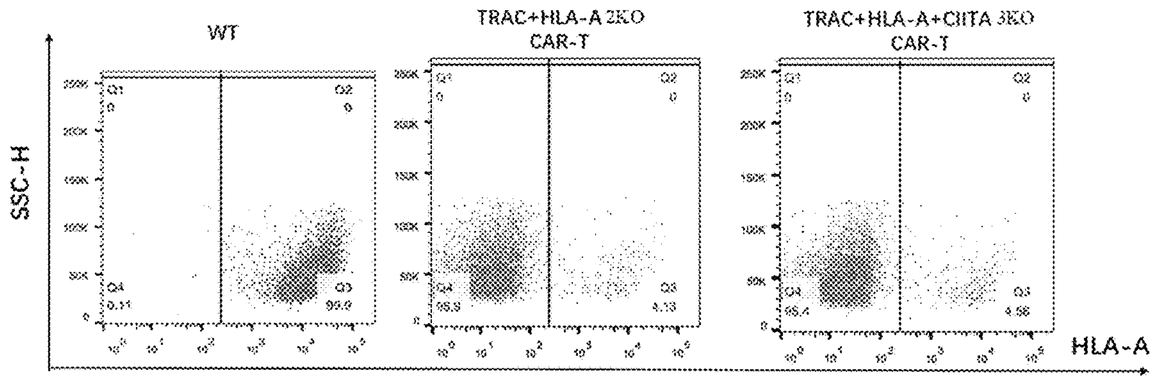
Figure 17C:
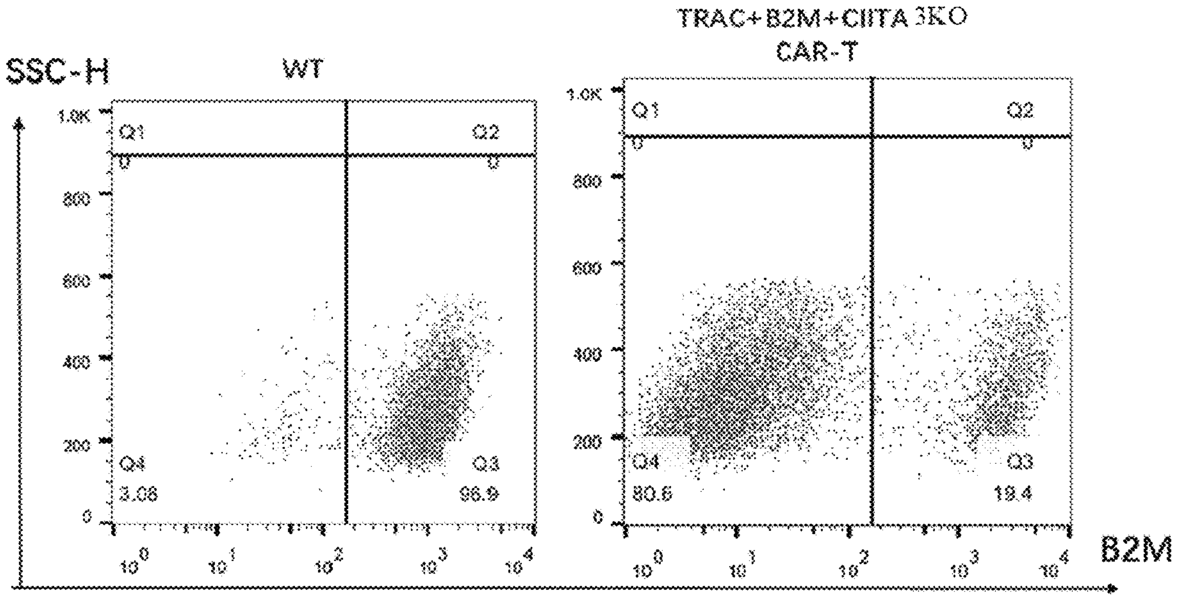
Figure 17D:
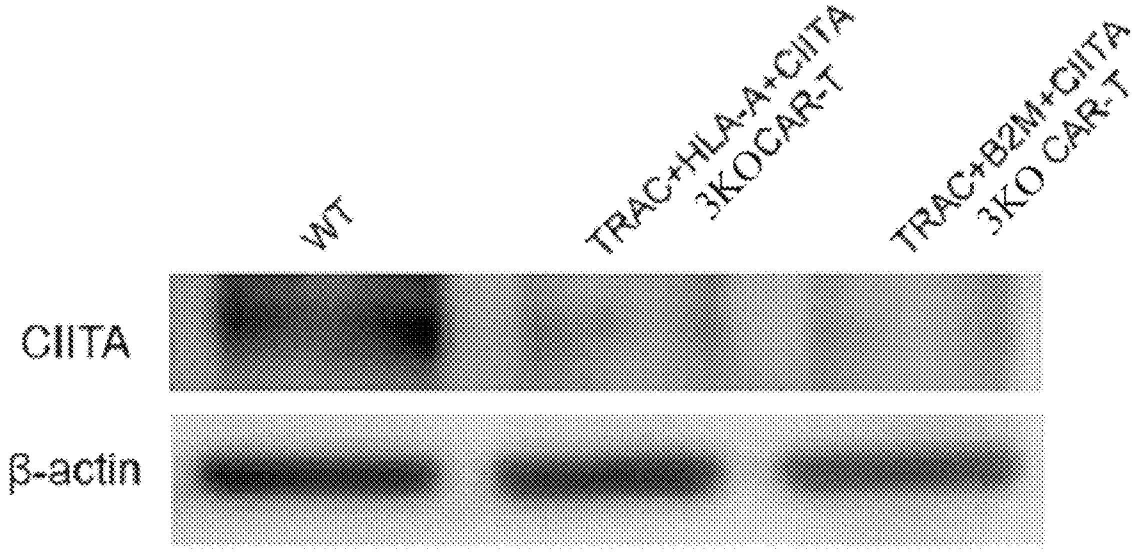

The results were shown in FIGS. 17A-17D, wherein, FIGS. 17A-17C sequentially showed the knockout status of TRAC, HLA-A and B2M in terms of protein levels; and FIG. 17D showed the knockout status of CIITA in terms of protein level, wherein, WT referred to the status with no knockout, TRAC+HLA-A dual knockout referred to the results of CAR-T cells in which the TRAC gene and the HLA-A gene were dual knockout; TRAC+HLA-A+CIITA triple knockout referred to the results of CAR-T cells in which the TRAC gene, the HLA-A gene and the CIITA gene were triple knockout; wherein TRAC+B2M+CIITA triple knockout referred to the results of CAR-T cells in which the B2M gene, the CIITA gene and the TRAC gene were triple knockout.

Figure 18:
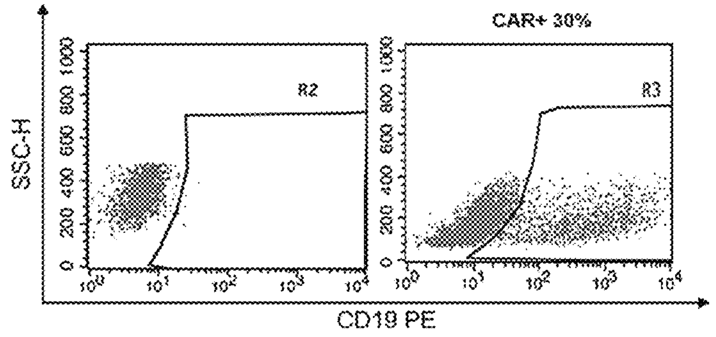
FIG. 18 shows the efficiency of the modified immune effector cells of the present application for infecting the CAR.

Of those, the transfection efficiency of CD19CAR was shown in FIGS. 18A-18B, wherein, CAR30%+ represented the transfection efficiency of CD19 CAR.

Figure 19:
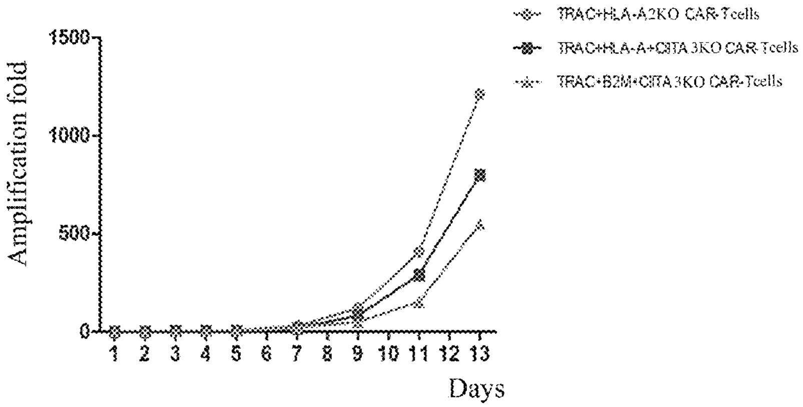
FIG. 19 shows the amplification fold of the modified immune effector cells of the present application.

FIG. 19 showed the amplification folds of different cells. Of those, the CAR-T cells in which the TRAC gene and the HLA-A gene were dual knockout had the maximum amplification fold.

Example 14 Anti-Tumor Effect of CAR-T Cells in which the TRAC Gene and the HLA-A Gene were Dual Knockout CAR-T cells in which the TRAC gene and the HLA-A gene were dual knockout (targeting CD19, CD20 or BCMA) were prepared in Example 14. Target cells expressing luciferase gene (target gene-positive leukemia or lymphoma cell lines, such as, Raji, Jurkat, MM1S and the like) were inoculated into a well place. Then, double knockout CAR-T cells, triple knockout CAR-T cells, and zero knockout CAR-T cells were added at different ratios of efficiency to target (1:2.5, 1:1, 5:1, 10:1), respectively. After 24 hours of co-culture, the cells were transferred to the detection well plate. The luciferase substrate was added, and the fluorescence value was detected by a microplate reader. Killing efficiency=1−the fluorescence value of T cells co-cultured with target cells/the fluorescence value of target cells cultured alone.

The results showed that the CAR-T cells in which the TRAC gene and the HLA-A gene were dual knockout exhibit significant killing effect on tumor cells.

Figure 20:
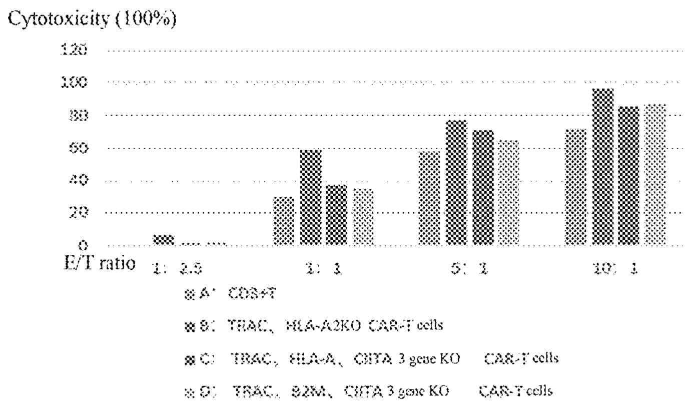
FIG. 20 shows the killing effect of the modified immune effector cells of the present application on CD19 positive target cells.

FIG. 20 showed that the killing effect on CD19 target cell Raji-Luciferase, wherein the CAR-T cells in which the TRAC gene and the HLA-A gene were dual knockout exhibit the most significant killing effect, wherein at each E/T ratio, the results corresponding to Notes A-D were shown from left to right.

Example 15 Anti-Tumor Effect of CAR-T Cells in which the TRAC Gene and the HLA-A Gene were Dual Knockout NSG mice were injected with tumor cells intravenously. After the tumor was successfully established, CAR-T cells in which the TRAC gene and the HLA-A gene were dual knockout, triple knockout CAR-T cells, and CAR-T cells in which no gene was knockout were refused back to the mice. The tumor size was monitored in the mice.

Mice to which the double knockout CAR-T cells were refused exhibited significantly slower growth rate of tumor.

Figure 21:
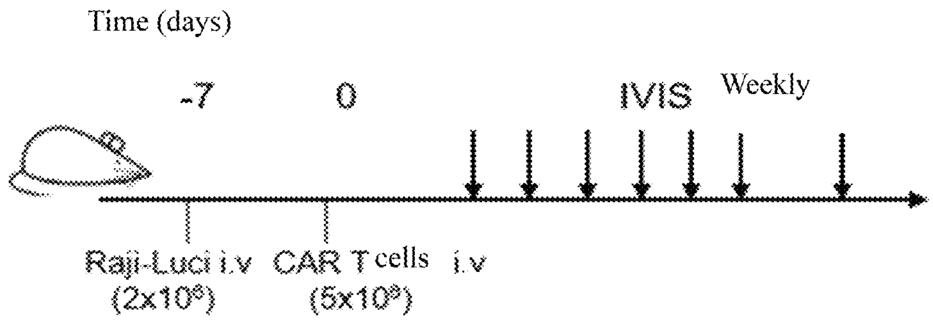
FIG. 21 shows a dosage regimen for administration of the modified immune effector cells of the present application.
Figure 22:
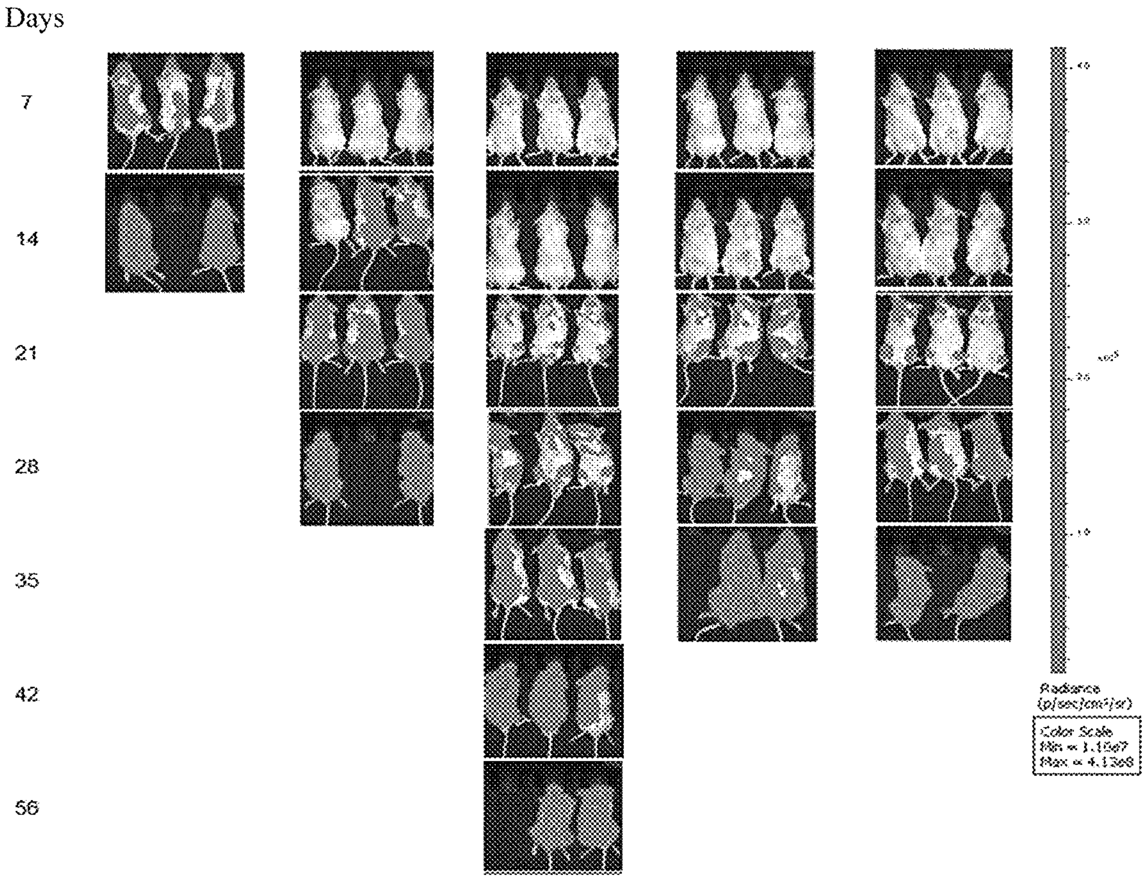
FIG. 22 shows the killing effect of the modified immune effector cells of the present application on the tumor in mice.

The results were shown in FIGS. 21-22, wherein, FIG. 21 showed the administration mode of mice, i.v. represented intravenous injection, CAR-T cells represented double knockout and triple knockout CAR-T cells expressing CD19 CAR. FIG. 20 showed the tumor size in mice after the mice were administered with CAR-T cells, wherein, FIG. 20 showed, from left column to right column, the tumor size in mice which were administered with normal saline, unmodified T cells, CD19 CAR-T cells in which the TRAC gene and the HLA-A gene were dual knockout, CD19 CAR-T cells in which TRAC, HLA-A and CIITA were triple knockout, CD19 CAR-T cells in which B2M, CIITA and TRAC were triple knockout in sequence. The results showed that the rate of tumor growth was significantly reduced in the mice re-infused with CAR-T cells in which both the TRAC gene and the HLA-A gene were knockout.

The aforesaid detailed description is provided in an illustrative and exemplary manner, and is not intended to limit the scope of the appended claims. Various modifications of embodiments currently listed in the present application are apparent for persons skilled in the art, and encompassed within the scope of the appended claims and their equivalents.

The invention claimed is:

1. A modified immunologic effector cell, wherein:

the expression and/or activity of a TRAC gene and a HLA-A gene of the cell is down-regulated, the expression and/or activity of a B2M gene of the cell is not down-regulated, and the expression and/or activity of a CIITA gene of the cell is not down-regulated, wherein each expression and/or activity is compared with that of the corresponding gene in a corresponding cell which is not modified and the unmodified cell includes the TRAC gene, the HLA-A gene, the CIITA gene and the B2M gene, wherein the modification comprises administering an sgRNA targeting an exon of said TRAC gene to said immunologic effector cell, and said sgRNA targeting the exon of said TRAC is shown in SEQ ID NO:1.

2. The modified immunologic effector cell of claim 1, wherein:

the expression and/or activity of the TRAC gene and the HLA-A gene is down-regulated, the expression and/or activity of the B2M gene is not down-regulated, and the expression and/or activity of the CIITA gene is not down-regulated, as compared with a corresponding wild type cell.

3. The modified immunologic effector cell of claim 1, wherein the modified immunologic effector cell is a T cell.

4. The modified immunologic effector cell of claim 1, wherein the modification is obtained by administering an sgRNA targeting an exon of the HLA-A gene and/or an sgRNA targeting the exon of the TRAC gene to the immunologic effector cell.

5. The modified immunologic effector cell of claim 4, wherein the sgRNA targeting the exon of the HLA-A gene comprises a nucleotide sequence shown in any one of SEQ ID No. 17-18 and 91-92.

6. The modified immunologic effector cell of claim 4, wherein the modification further comprises administering a Cas enzyme to the immunologic effector cell.

7. The modified immunologic effector cell of claim 1, comprising a nucleic acid encoding a chimeric antigen receptor, wherein the chimeric antigen receptor comprises an antigen binding domain, a hinge region, a transmembrane domain, a costimulatory structure, and a primary signal transduction domain.

8. The modified immunologic effector cell of claim 7, wherein the antigen binding domain specifically binds to a tumor antigen.

9. The modified immunologic effector cell of claim 8, wherein the tumor antigen is selected from the group consisting of CD19, CD20, and BCMA.

10. The modified immunologic effector cell of claim 7, wherein the antigen binding domain is selected from the group consisting of a monoclonal antibody, a polyclonal antibody, a human antibody, a humanized antibody, a single domain antibody, and an antigen binding fragment.

11. The modified immunologic effector cell claim 7, wherein the antigen binding domain targets a solid tumor and/or a non-solid tumor.

12. The modified immunologic effector cell of claim 11, wherein the solid tumor is selected from the group consisting of liver cancer, stomach cancer, lung cancer, breast cancer, and non-small cell lung cancer, and/or wherein the non-solid tumor is selected from the group consisting of B cell lymphoma, Hodgkin's lymphoma, chronic myeloid leukemia, and acute myeloid leukemia.

13. A composition, comprising the modified immunologic effector cell of claim 1 and a pharmaceutically acceptable carrier.

14. A composition, comprising a cell population and a pharmaceutically acceptable carrier, wherein the cell population comprises the modified immunologic effector cell of claim 1.

15. A method of allogeneic therapy, comprising administering to a subject in need thereof the modified immunologic effector cell of claim 1.

16. The method of claim 15, wherein the method is used to treat a tumor.

17. The method of claim 16, wherein the tumor comprises a solid tumor and/or a non-solid tumor.

18. The method of claim 17, wherein the tumor is selected from the group consisting of liver cancer, stomach cancer, lung cancer, breast cancer, non-small cell lung cells, B cell lymphoma, Hodgkin's lymphoma, chronic myeloid leukemia, and acute myeloid leukemia.

* * * * *

SEQUENCE LISTING

<160> NUMBER OF SEQ ID NOS: 120

<210> SEQ ID NO 1
<211> LENGTH: 20
<212> TYPE: RNA
<213> ORGANISM: Artificial Sequence
<220> FEATURE:
<223> OTHER INFORMATION: TRAC sg9

<400> SEQUENCE: 1
agagucucuc agcugguaca 20

<210> SEQ ID NO 2
<211> LENGTH: 20
<212> TYPE: RNA
<213> ORGANISM: Artificial Sequence
<220> FEATURE:
<223> OTHER INFORMATION: TRAC sg10

<400> SEQUENCE: 2
ugugcuagac augaggucua 20

<210> SEQ ID NO 3
<211> LENGTH: 20
<212> TYPE: RNA
<213> ORGANISM: Artificial Sequence
<220> FEATURE:
<223> OTHER INFORMATION: TRAC sg11

<400> SEQUENCE: 3
cucucagcug guacacggca 20

<210> SEQ ID NO 4
<211> LENGTH: 20
<212> TYPE: RNA
<213> ORGANISM: Artificial Sequence
<220> FEATURE:
<223> OTHER INFORMATION: TRAC sg12

<400> SEQUENCE: 4
acacggcagg gucaggguuc 20

<210> SEQ ID NO 5
<211> LENGTH: 20
<212> TYPE: RNA
<213> ORGANISM: Artificial Sequence
<220> FEATURE:
<223> OTHER INFORMATION: TRAC sg13

<400> SEQUENCE: 5
agcugguaca cggcaggguc 20

<210> SEQ ID NO 6
<211> LENGTH: 20
<212> TYPE: RNA
<213> ORGANISM: Artificial Sequence
<220> FEATURE:
<223> OTHER INFORMATION: TRAC sg14

<400> SEQUENCE: 6
gagaaucaaa aucggugaau 20

<210> SEQ ID NO 7
<211> LENGTH: 20
<212> TYPE: RNA
<213> ORGANISM: Artificial Sequence
<220> FEATURE:
<223> OTHER INFORMATION: TRAC sg15

<400> SEQUENCE: 7
gacaccuucu uccccagccc 20

<210> SEQ ID NO 8
<211> LENGTH: 20
<212> TYPE: RNA
<213> ORGANISM: Artificial Sequence
<220> FEATURE:
<223> OTHER INFORMATION: TRAC sg16

<400> SEQUENCE: 8
ucucucagcu gguacacggc 20

<210> SEQ ID NO 9
<211> LENGTH: 20
<212> TYPE: RNA
<213> ORGANISM: Artificial Sequence
<220> FEATURE:
<223> OTHER INFORMATION: TRAC sg17

<400> SEQUENCE: 9
gcugguacac ggcaggguca 20

<210> SEQ ID NO 10
<211> LENGTH: 20
<212> TYPE: RNA
<213> ORGANISM: Artificial Sequence
<220> FEATURE:
<223> OTHER INFORMATION: TRAC sg18

<400> SEQUENCE: 10
aaagucagau uuguugcucc 20

<210> SEQ ID NO 11
<211> LENGTH: 20
<212> TYPE: RNA
<213> ORGANISM: Artificial Sequence
<220> FEATURE:
<223> OTHER INFORMATION: TRAC sg19

<400> SEQUENCE: 11
cuggggaaga aggugucuuc 20

<210> SEQ ID NO 12
<211> LENGTH: 20
<212> TYPE: RNA
<213> ORGANISM: Artificial Sequence
<220> FEATURE:
<223> OTHER INFORMATION: TRAC sg20

<400> SEQUENCE: 12
uggauuuaga gucucucagc 20

<210> SEQ ID NO 13
<211> LENGTH: 20
<212> TYPE: RNA
<213> ORGANISM: Artificial Sequence
<220> FEATURE:
<223> OTHER INFORMATION: TRAC sg21

<400> SEQUENCE: 13
agagcaacag ugcuguggcc 20

<210> SEQ ID NO 14
<211> LENGTH: 20
<212> TYPE: RNA
<213> ORGANISM: Artificial Sequence
<220> FEATURE:
<223> OTHER INFORMATION: TRAC sg22

<400> SEQUENCE: 14
cuucaagagc aacagugcug 20

<210> SEQ ID NO 15
<211> LENGTH: 20
<212> TYPE: RNA
<213> ORGANISM: Artificial Sequence
<220> FEATURE:
<223> OTHER INFORMATION: TRAC sg23

<400> SEQUENCE: 15
auuuguuuga gaaucaaaau 20

<210> SEQ ID NO 16
<211> LENGTH: 20
<212> TYPE: RNA
<213> ORGANISM: Artificial Sequence
<220> FEATURE:
<223> OTHER INFORMATION: HLA-A02 sg10

<400> SEQUENCE: 16
cccucguccu gcuacucucg 20

<210> SEQ ID NO 17
<211> LENGTH: 20
<212> TYPE: RNA
<213> ORGANISM: Artificial Sequence
<220> FEATURE:
<223> OTHER INFORMATION: HLA-A02 sg2

<400> SEQUENCE: 17
cguacuggug guacccgcgg 20

<210> SEQ ID NO 18
<211> LENGTH: 20
<212> TYPE: RNA
<213> ORGANISM: Artificial Sequence
<220> FEATURE:
<223> OTHER INFORMATION: HLA-A02 sg5

<400> SEQUENCE: 18
cugaccauga agccacccug 20

<210> SEQ ID NO 19
<211> LENGTH: 20
<212> TYPE: RNA
<213> ORGANISM: Artificial Sequence
<220> FEATURE:
<223> OTHER INFORMATION: HLA-A02 sg14

<400> SEQUENCE: 19
agacucaccg aguggaccug 20

<210> SEQ ID NO 20
<211> LENGTH: 20
<212> TYPE: RNA
<213> ORGANISM: Artificial Sequence
<220> FEATURE:
<223> OTHER INFORMATION: HLA-A02 sg21

<400> SEQUENCE: 20
ggacccuccu gcucuaucca 20

<210> SEQ ID NO 21
<211> LENGTH: 20
<212> TYPE: RNA
<213> ORGANISM: Artificial Sequence
<220> FEATURE:
<223> OTHER INFORMATION: HLA-A02 sg23

<400> SEQUENCE: 21
gauguaaucc uugccgucgu 20

<210> SEQ ID NO 22
<211> LENGTH: 20
<212> TYPE: RNA
<213> ORGANISM: Artificial Sequence
<220> FEATURE:
<223> OTHER INFORMATION: HLA-A02 sg26

<400> SEQUENCE: 22
ccugcgcucu uggaccgcgg 20

<210> SEQ ID NO 23
<211> LENGTH: 20
<212> TYPE: RNA
<213> ORGANISM: Artificial Sequence
<220> FEATURE:
<223> OTHER INFORMATION: HLA-A02 sg29

<400> SEQUENCE: 23
ccucguccug cuacucucgg 20

<210> SEQ ID NO 24
<211> LENGTH: 20
<212> TYPE: RNA
<213> ORGANISM: Artificial Sequence
<220> FEATURE:
<223> OTHER INFORMATION: HLA-A02 sg30

<400> SEQUENCE: 24
aacccucguc cugcuacucu 20

<210> SEQ ID NO 25
<211> LENGTH: 20
<212> TYPE: RNA
<213> ORGANISM: Artificial Sequence
<220> FEATURE:
<223> OTHER INFORMATION: HLA-A02 sg31

<400> SEQUENCE: 25
gaggguucgg ggcgccauga 20

<210> SEQ ID NO 26
<211> LENGTH: 20
<212> TYPE: RNA
<213> ORGANISM: Artificial Sequence
<220> FEATURE:
<223> OTHER INFORMATION: HLA-A02 sg32

<400> SEQUENCE: 26
ccugcuacuc ucgggggcuc 20

<210> SEQ ID NO 27

<211> LENGTH: 20
<212> TYPE: RNA
<213> ORGANISM: Artificial Sequence
<220> FEATURE:
<223> OTHER INFORMATION: HLA-A02 sg33

<400> SEQUENCE: 27
cugguuguag uagccgcgca 20

<210> SEQ ID NO 28
<211> LENGTH: 20
<212> TYPE: RNA
<213> ORGANISM: Artificial Sequence
<220> FEATURE:
<223> OTHER INFORMATION: HLA-A02 sg34

<400> SEQUENCE: 28
uagcccacug cgaugaagcg 20

<210> SEQ ID NO 29
<211> LENGTH: 20
<212> TYPE: RNA
<213> ORGANISM: Artificial Sequence
<220> FEATURE:
<223> OTHER INFORMATION: HLA-A02 sg35

<400> SEQUENCE: 29
guggaccugg ggacccugcg 20

<210> SEQ ID NO 30
<211> LENGTH: 20
<212> TYPE: RNA
<213> ORGANISM: Artificial Sequence
<220> FEATURE:
<223> OTHER INFORMATION: HLA-A02 sg36

<400> SEQUENCE: 30
uggacgacac gcaguucgug 20

<210> SEQ ID NO 31
<211> LENGTH: 20
<212> TYPE: RNA
<213> ORGANISM: Artificial Sequence
<220> FEATURE:
<223> OTHER INFORMATION: HLA-A02 sg37

<400> SEQUENCE: 31
acagacucac cgaguggacc 20

<210> SEQ ID NO 32
<211> LENGTH: 20
<212> TYPE: RNA
<213> ORGANISM: Artificial Sequence
<220> FEATURE:
<223> OTHER INFORMATION: HLA-A02 sg38

<400> SEQUENCE: 32
gcaggagggu ccggaguauu 20

<210> SEQ ID NO 33
<211> LENGTH: 20
<212> TYPE: RNA
<213> ORGANISM: Artificial Sequence
<220> FEATURE:
<223> OTHER INFORMATION: HLA-A02 sg39

<400> SEQUENCE: 33
aguauuggga cggggagaca 20

<210> SEQ ID NO 34
<211> LENGTH: 20
<212> TYPE: RNA
<213> ORGANISM: Artificial Sequence
<220> FEATURE:
<223> OTHER INFORMATION: HLA-A02 sg40

<400> SEQUENCE: 34
cucagaccac caagcacaag 20

<210> SEQ ID NO 35
<211> LENGTH: 20
<212> TYPE: RNA
<213> ORGANISM: Artificial Sequence
<220> FEATURE:
<223> OTHER INFORMATION: HLA-A02 sg41

<400> SEQUENCE: 35
ccgccgcggu ccaagagcgc 20

<210> SEQ ID NO 36
<211> LENGTH: 20
<212> TYPE: RNA
<213> ORGANISM: Artificial Sequence
<220> FEATURE:
<223> OTHER INFORMATION: HLA-A02 sg42

<400> SEQUENCE: 36
cucuuggacc gcggcggaca 20

<210> SEQ ID NO 37
<211> LENGTH: 20
<212> TYPE: RNA
<213> ORGANISM: Artificial Sequence
<220> FEATURE:
<223> OTHER INFORMATION: HLA-A02 sg43

<400> SEQUENCE: 37
ggauuacauc gcccugaaag 20

<210> SEQ ID NO 38
<211> LENGTH: 20
<212> TYPE: RNA
<213> ORGANISM: Artificial Sequence
<220> FEATURE:
<223> OTHER INFORMATION: HLA-A11 sg8-3

<400> SEQUENCE: 38
cccccgagag uagcaggagg 20

<210> SEQ ID NO 39
<211> LENGTH: 20
<212> TYPE: RNA
<213> ORGANISM: Artificial Sequence
<220> FEATURE:
<223> OTHER INFORMATION: HLA-A11 sg9-3

<400> SEQUENCE: 39
aguagcagga ggaggguucg 20

<210> SEQ ID NO 40

<211> LENGTH: 20
<212> TYPE: RNA
<213> ORGANISM: Artificial Sequence
<220> FEATURE:
<223> OTHER INFORMATION: HLA-A11 sg10-3

<400> SEQUENCE: 40
cccuccuccu gcuacucucg 20

<210> SEQ ID NO 41
<211> LENGTH: 20
<212> TYPE: RNA
<213> ORGANISM: Artificial Sequence
<220> FEATURE:
<223> OTHER INFORMATION: HLA-A11 sg11-3

<400> SEQUENCE: 41
ccccgagagu agcaggagga 20

<210> SEQ ID NO 42
<211> LENGTH: 20
<212> TYPE: RNA
<213> ORGANISM: Artificial Sequence
<220> FEATURE:
<223> OTHER INFORMATION: HLA-A11 sg14-3

<400> SEQUENCE: 42
agacugaccg aguggaccug 20

<210> SEQ ID NO 43
<211> LENGTH: 20
<212> TYPE: RNA
<213> ORGANISM: Artificial Sequence
<220> FEATURE:
<223> OTHER INFORMATION: HLA-A11 sg16-3

<400> SEQUENCE: 43
ggggccggag uauugggacc 20

<210> SEQ ID NO 44
<211> LENGTH: 20
<212> TYPE: RNA
<213> ORGANISM: Artificial Sequence
<220> FEATURE:
<223> OTHER INFORMATION: HLA-A11 sg20-3

<400> SEQUENCE: 44
ccacucgguc agucugugac 20

<210> SEQ ID NO 45
<211> LENGTH: 20
<212> TYPE: RNA
<213> ORGANISM: Artificial Sequence
<220> FEATURE:
<223> OTHER INFORMATION: HLA-A11 sg21-3

<400> SEQUENCE: 45
uggauagagc aggaggggcc 20

<210> SEQ ID NO 46
<211> LENGTH: 20
<212> TYPE: RNA
<213> ORGANISM: Artificial Sequence
<220> FEATURE:
<223> OTHER INFORMATION: HLA-A11 sg28-3

<400> SEQUENCE: 46
ugccgucgua ggcguccugc 20

<210> SEQ ID NO 47
<211> LENGTH: 20
<212> TYPE: RNA
<213> ORGANISM: Artificial Sequence
<220> FEATURE:
<223> OTHER INFORMATION: HLA-A24 sg12-2

<400> SEQUENCE: 47
ccuggcccug acccagaccu 20

<210> SEQ ID NO 48
<211> LENGTH: 20
<212> TYPE: RNA
<213> ORGANISM: Artificial Sequence
<220> FEATURE:
<223> OTHER INFORMATION: HLA-A24 sg13-2

<400> SEQUENCE: 48
cccuggcccu gacccagacc 20

<210> SEQ ID NO 49
<211> LENGTH: 20
<212> TYPE: RNA
<213> ORGANISM: Artificial Sequence
<220> FEATURE:
<223> OTHER INFORMATION: HLA-A24 sg14-2

<400> SEQUENCE: 49
agacugaccg agagaaccug 20

<210> SEQ ID NO 50
<211> LENGTH: 20
<212> TYPE: RNA
<213> ORGANISM: Artificial Sequence
<220> FEATURE:
<223> OTHER INFORMATION: HLA-A24 sg16-2

<400> SEQUENCE: 50
ggggccggag uauugggacg 20

<210> SEQ ID NO 51
<211> LENGTH: 20
<212> TYPE: RNA
<213> ORGANISM: Artificial Sequence
<220> FEATURE:
<223> OTHER INFORMATION: HLA-A24 sg20-2

<400> SEQUENCE: 51
ucucucgguc agucugugag 20

<210> SEQ ID NO 52
<211> LENGTH: 20
<212> TYPE: RNA
<213> ORGANISM: Artificial Sequence
<220> FEATURE:
<223> OTHER INFORMATION: HLA-A24 sg21-2

<400> SEQUENCE: 52
ggccccuccu gcucuaucca 20

<210> SEQ ID NO 53

<211> LENGTH: 20
<212> TYPE: RNA
<213> ORGANISM: Artificial Sequence
<220> FEATURE:
<223> OTHER INFORMATION: HLA-A24 sg22-2

<400> SEQUENCE: 53
aggcguacug gugguacccg 20

<210> SEQ ID NO 54
<211> LENGTH: 20
<212> TYPE: RNA
<213> ORGANISM: Artificial Sequence
<220> FEATURE:
<223> OTHER INFORMATION: HLA-A24 sg25-2

<400> SEQUENCE: 54
cugagccgcc auguccgccg 20

<210> SEQ ID NO 55
<211> LENGTH: 4627
<212> TYPE: DNA
<213> ORGANISM: Artificial Sequence
<220> FEATURE:
<223> OTHER INFORMATION: TRAC nucleotide sequence

<400> SEQUENCE: 55
atatccagaa ccctgaccct gccgtgtacc agctgagaga ctctaaatcc agtgacaagt 60
ctgtctgcct attcaccgat tttgattctc aaacaaatgt gtcacaaagt aaggattctg 120
atgtgtatat cacagacaaa actgtgctag acatgaggtc tatggacttc aagagcaaca 180
gtgctgtggc ctggagcaac aaatctgact ttgcatgtgc aaacgccttc aacaacagca 240
ttattccaga agacaccttc ttccccagcc caggtaaggg cagctttggt gccttcgcag 300
gctgtttcct tgcttcagga atggccaggt tctgcccaga gctctggtca atgatgtcta 360
aaactcctct gattggtggt ctcggcctta tccattgcca ccaaaaccct ctttttacta 420
agaaacagtg agccttgttc tggcagtcca gagaatgaca cgggaaaaaa gcagatgaag 480
agaaggtggc aggagagggc acgtggccca gcctcagtct ctccaactga gttcctgcct 540
gcctgccttt gctcagactg tttgcccctt actgctcttc taggcctcat tctaagcccc 600
ttctccaagt tgcctctcct tatttctccc tgtctgccaa aaaatctttc ccagctcact 660
aagtcagtct cacgcagtca ctcattaacc caccaatcac tgattgtgcc ggcacatgaa 720
tgcaccaggt gttgaagtgg aggaattaaa aagtcagatg aggggtgtgc ccagaggaag 780
caccattcta gttgggggag cccatctgtc agctgggaaa agtccaaata acttcagatt 840
ggaatgtgtt ttaactcagg gttgagaaaa cagctacctt caggacaaaa gtcagggaag 900
ggctctctga agaaatgcta cttgaagata ccagccctac caagggcagg gagaggaccc 960
tatagaggcc tgggacagga gctcaatgag aaaggagaag agcagcaggc atgagttgaa 1020
tgaaggaggc agggccgggt cacagggcct tctaggccat gagagggtag acagtattct 1080
aaggacgcca gaaagctgtt gatcggcttc aagcagggga gggacaccta atttgctttt 1140
cttttttttt ttttttttt ttttttttt tgagatggag ttttgctctt gttgcccagg 1200
ctggagtgca atggtgcatc ttggctcact gcaacctccg cctcccaggt tcaagtgatt 1260
ctcctgcctc agcctcccga gtagctgaga ttacaggcac ccgccaccat gcctggctaa 1320
ttttttgtat ttttagtaga gacagggttt cactatgttg gccaggctgg tctcgaactc 1380
ctgacctcag gtgatccacc cgcttcagcc tcccaaagtg ctgggattac aggcgtgagc 1440

```
caccacaccc ggcctgcttt tcttaaagat caatctgagt gctgtacgga gagtgggttg   1500
taagccaaga gtagaagcag aaagggagca gttgcagcag agagatgatg gaggcctggg   1560
cagggtggtg gcagggaggt aaccaacacc attcaggttt caaaggtaga accatgcagg   1620
gatgagaaag caaagagggg atcaaggaag gcagctggat tttggcctga gcagctgagt   1680
caatgatagt gccgtttact aagaagaaac caaggaaaaa atttggggtg cagggatcaa   1740
aactttttgg aacatatgaa agtacgtgtt tatactcttt atggcccttg tcactatgta   1800
tgcctcgctg cctccattgg actctagaat gaagccaggc aagagcaggg tctatgtgtg   1860
atggcacatg tggccagggt catgcaacat gtactttgta caaacagtgt atattgagta   1920
aatagaaatg gtgtccagga gccgaggtat cggtcctgcc agggccaggg gctctcccta   1980
gcaggtgctc atatgctgta agttccctcc agatctctcc acaaggaggc atggaaaggc   2040
tgtagttgtt cacctgccca agaactagga ggtctggggt gggagagtca gcctgctctg   2100
gatgctgaaa gaatgtctgt ttttcctttt agaaagttcc tgtgatgtca agctggtcga   2160
gaaaagcttt gaaacaggta agacaggggt ctagcctggg tttgcacagg attgcggaag   2220
tgatgaaccc gcaataaccc tgcctggatg agggagtggg aagaaattag tagatgtggg   2280
aatgaatgat gaggaatgga aacagcggtt caagacctgc ccagagctgg gtggggtctc   2340
tcctgaatcc ctctcaccat ctctgacttt ccattctaag cactttgagg atgagtttct   2400
agcttcaata gaccaaggac tctctcctag gcctctgtat tcctttcaac agctccactg   2460
tcaagagagc cagagagagc ttctgggtgg cccagctgtg aaatttctga gtcccttagg   2520
gatagcccta aacgaaccag atcatcctga ggacagccaa gaggttttgc cttctttcaa   2580
gacaagcaac agtactcaca taggctgtgg gcaatggtcc tgtctctcaa gaatcccctg   2640
ccactcctca cacccaccct gggcccatat tcatttccat ttgagttgtt cttattgagt   2700
catccttcct gtggtagcgg aactcactaa ggggcccatc tggacccgag gtattgtgat   2760
gataaattct gagcacctac cccatcccca gaagggctca gaaataaaat aagagccaag   2820
tctagtcggt gtttcctgtc ttgaaacaca atactgttgg ccctggaaga atgcacagaa   2880
tctgtttgta aggggatatg cacagaagct gcaagggaca ggaggtgcag gagctgcagg   2940
cctcccccac ccagcctgct ctgccttggg gaaaaccgtg ggtgtgtcct gcaggccatg   3000
caggcctggg acatgcaagc ccataaccgc tgtggcctct tggttttaca gatacgaacc   3060
taaactttca aaacctgtca gtgattgggt tccgaatcct cctcctgaaa gtggccgggt   3120
ttaatctgct catgacgctg cggctgtggt ccagctgagg tgaggggcct tgaagctggg   3180
agtggggttt agggacgcgg gtctctgggt gcatcctaag ctctgagagc aaacctccct   3240
gcagggtctt gcttttaagt ccaaagcctg agcccaccaa actctcctac ttcttcctgt   3300
tacaaattcc tcttgtgcaa taataatggc ctgaaacgct gtaaaatatc ctcatttcag   3360
ccgcctcagt tgcacttctc ccctatgagg taggaagaac agttgtttag aaacgaagaa   3420
actgaggccc cacagctaat gagtggagga agagagacac ttgtgtacac cacatgcctt   3480
gtgttgtact tctctcaccg tgtaacctcc tcatgtcctc tctccccagt acggctctct   3540
tagctcagta gaaagaagac attacactca tattacaccc caatcctggc tagagtctcc   3600
gcaccctcct cccccagggt ccccagtcgt cttgctgaca actgcatcct gttccatcac   3660
catcaaaaaa aaactccagg ctgggtgcgg gggctcacac ctgtaatccc agcactttgg   3720
gaggcagagg caggaggagc acaggagctg gagaccagcc tgggcaacac agggagaccc   3780
```

cgcctctaca aaaagtgaaa aaattaacca ggtgtggtgc tgcacacctg tagtcccagc 3840
tacttaagag gctgagatgg gaggatcgct tgagccctgg aatgttgagg ctacaatgag 3900
ctgtgattgc gtcactgcac tccagcctgg aagacaaagc aagatcctgt ctcaaataat 3960
aaaaaaaata agaactccag ggtacatttg ctcctagaac tctaccacat agccccaaac 4020
agagccatca ccatcacatc cctaacagtc ctgggtcttc ctcagtgtcc agcctgactt 4080
ctgttcttcc tcattccaga tctgcaagat tgtaagacag cctgtgctcc ctcgctcctt 4140
cctctgcatt gcccctcttc tccctctcca aacagaggga actctcctac ccccaaggag 4200
gtgaaagctg ctaccacctc tgtgcccccc cggcaatgcc accaactgga tcctacccga 4260
atttatgatt aagattgctg aagagctgcc aaacactgct gccacccccct ctgttccctt 4320 attgctgctt gtcactgcct gacattcacg gcagaggcaa ggctgctgca gcctcccctg 4380
gctgtgcaca ttccctcctg ctccccagag actgcctccg ccatcccaca gatgatggat 4440
cttcagtggg ttctcttggg ctctaggtcc tgcagaatgt tgtgaggggt ttattttttt 4500
ttaatagtgt tcataaagaa atacatagta ttcttcttct caagacgtgg ggggaaatta 4560
tctcattatc gaggccctgc tatgctgtgt atctgggcgt gttgtatgtc ctgctgccga 4620
tgccttc 4627

<210> SEQ ID NO 56
<211> LENGTH: 3517
<212> TYPE: DNA
<213> ORGANISM: Artificial Sequence
<220> FEATURE:
<223> OTHER INFORMATION: HLA-A02010101 nucleotide sequence

<400> SEQUENCE: 56
cagaagcaga ggggtcaggg cgaagtccca gggccccagg cgtggctctc agggtctcag 60
gccccgaagg cggtgtatgg attggggagt cccagccttg gggattcccc aactccgcag 120
tttcttttct ccctctccca acctatgtag ggtccttctt cctggatact cacgacgcgg 180
acccagttct cactcccatt gggtgtcggg tttccagaga agccaatcag tgtcgtcgcg 240
gtcgcggttc taaagtccgc acgcacccac cgggactcag attctcccca gacgccgagg 300
atggccgtca tggcgccccg aaccctcgtc ctgctactct cgggggctct ggccctgacc 360
cagacctggg cgggtgagtg cggggtcggg agggaaacgg cctctgtggg gagaagcaac 420
gggcccgcct ggcgggggcg caggacccgg gaagccgcgc cgggaggagg gtcgggcggg 480
tctcagccac tcctcgtccc caggctctca ctccatgagg tatttcttca catccgtgtc 540
ccggcccggc cgcggggagc cccgcttcat cgcagtgggc tacgtggacg acacgcagtt 600
cgtgcggttc gacagcgacg ccgcgagcca gaggatggag ccgcgggcgc cgtggataga 660
gcaggagggt ccggagtatt gggacgggga gacacggaaa gtgaaggccc actcacagac 720
tcaccgagtg gacctgggga ccctgcgcgg ctactacaac cagagcgagg ccggtgagtg 780
accccggccc ggggcgcagg tcacgacctc tcatccccca cggacgggcc aggtcgccca 840
cagtctccgg gtccgagatc cgccccgaag ccgcgggacc ccgagaccct tgccccggga 900
gaggcccagg cgcctttacc cggtttcatt ttcagtttag gccaaaaatc cccccaggtt 960
ggtcggggcg gggcggggct cgggggaccg ggctgaccgc ggggtccggg ccaggttctc 1020
acaccgtcca gaggatgtat ggctgcgacg tggggtcgga ctggcgcttc ctccgcgggt 1080
accaccagta cgcctacgac ggcaaggatt acatcgccct gaaagaggac ctgcgctctt 1140
ggaccgcggc ggacatggca gctcagacca ccaagcacaa gtgggaggcg gcccatgtgg 1200

```
cggagcagtt gagagcctac ctggagggca cgtgcgtgga gtggctccgc agatacctgg   1260
agaacgggaa ggagacgctg cagcgcacgg gtaccagggg ccacggggcg cctccctgat   1320
cgcctgtaga tctcccgggc tggcctccca caaggagggg agacaattgg gaccaacact   1380
agaatatcgc cctccctctg gtcctgaggg agaggaatcc tcctgggttt ccagatcctg   1440
taccagagag tgactctgag gttccgccct gctctctgac acaattaagg gataaaatct   1500
ctgaaggaat gacgggaaga cgatccctcg aatactgatg agtggttccc tttgacacac   1560
acaggcagca gccttgggcc cgtgactttt cctctcaggc cttgttctct gcttcacact   1620
caatgtgtgt gggggtctga gtccagcact tctgagtcct tcagcctcca ctcaggtcag   1680
gaccagaagt cgctgttccc tcttcaggga ctagaatttt ccacggaata ggagattatc   1740
ccaggtgcct gtgtccaggc tggtgtctgg gttctgtgct cccttcccca tcccaggtgt   1800
cctgtccatt ctcaagatag ccacatgtgt gctggaggag tgtcccatga cagatgcaaa   1860
atgcctgaat gatctgactc ttcctgacag acgcccccaa aacgcatatg actcaccacg   1920
ctgtctctga ccatgaagcc accctgaggt gctgggccct gagcttctac cctgcggaga   1980
tcacactgac ctggcagcgg gatggggagg accagaccca ggacacggag ctcgtggaga   2040
ccaggcctgc aggggatgga accttccaga agtgggcggc tgtggtggtg ccttctggac   2100
aggagcagag atacacctgc catgtgcagc atgagggttt gcccaagccc ctcaccctga   2160
gatggggtaa ggagggagac gggggtgtca tgtcttttag ggaaagcagg agcctctctg   2220
acctttagca gggtcagggc ccctcacctt cccctctttt cccagagccg tcttcccagc   2280
ccaccatccc catcgtgggc atcattgctg gcctggttct ctttggagct gtgatcactg   2340
gagctgtggt cgctgctgtg atgtggagga ggaagagctc aggtggggaa ggggtgaagg   2400
gtgggtctga gatttcttgt ctcactgagg gttccaagac ccaggtagaa gtgtgccctg   2460
cctcgttact gggaagcacc acccacaatt atgggcctac ccagcctggg ccctgtgtgc   2520
cagcacttac tcttttgtaa agcacctgtt aaaatgaagg acagatttat caccttgatt   2580
acagcggtga tgggacctga tcccagcagt cacaagtcac aggggaaggt ccctgaggac   2640
cttcaggagg gcggttggtc caggacccac acctgctttc ttcatgtttc ctgatcccgc   2700
cctgggtctg cagtcacaca tttctggaaa cttctctgag gtccaagact tggaggttcc   2760
tctaggacct taaggccctg actcctttct ggtatctcac aggacatttt cttcccacag   2820
atagaaaagg agggagctac tctcaggctg caagtaagta tgaaggaggc tgatgcctga   2880
ggtccttggg atattgtgtt tgggagccca tgggggagct cacccacccc acaattcctc   2940
ctctagccac atcttctgtg ggatctgacc aggttctgtt tttgttctac cccaggcagt   3000
gacagtgccc agggctctga tgtgtctctc acagcttgta aaggtgagag cctggagggc   3060
ctgatgtgtg ttgggtgttg ggcggaacag tggacacagc tgtgctatgg ggtttctttc   3120
cattggatgt attgagcatg cgatgggctg tttaaagtgt gacccctcac tgtgacagat   3180
acgaatttgt tcatgaatat ttttttctat agtgtgagac agctgccttg tgtgggactg   3240
agaggcaaga gttgttcctg cccttccctt tgtgacttga agaaccctga ctttgtttct   3300
gcaaaggcac ctgcatgtgt ctgtgttcgt gtaggcataa tgtgaggagg tggggagacc   3360
accccacccc catgtccacc atgaccctct tcccacgctg acctgtgctc cctccccaat   3420
catctttcct gttccagaga ggtggggctg aggtgtctcc atctctgtct caacttcatg   3480
gtgcactgag ctgtaacttc ttccttccct attaaaa                            3517
```

<210> SEQ ID NO 57
<211> LENGTH: 3503
<212> TYPE: DNA
<213> ORGANISM: Artificial Sequence
<220> FEATURE:
<223> OTHER INFORMATION: HLA-A11010101 nucleotide sequence

<400> SEQUENCE: 57
caagagcaga ggggtcaggg cgaagtccca gggccccagg cgtggctctc agggtctcag 60
gccccgaagg cggtgtatgg attggggagt cccagccttg gggattcccc aactccgcag 120
tttcttttct ccctctccca acctacgtag ggtccttcat cctggatact cacgacgcgg 180
acccagttct cactcccatt gggtgtcggg tttccagaga agccaatcag tgtcttcgcg 240
gtcgctcttc taaagtccgc acgcacccac cgggactcag attctcccca gaccccgagg 300
atggccgtca tggcgccccg aaccctcctc ctgctactct cgggggccct ggccctgacc 360
cagacctggg cgggtgagtg cggggtcggg agggaaaccg cctctgcggg gagaagcaag 420
gggccctcct ggcgggggcg caggaccggg ggagccgcgc cgggaggagg gtcgggcagg 480
tctcagccac tgctcgcccc caggctccca ctccatgagg tatttctaca cctccgtgtc 540
ccggcccggc cgcggggagc cccgcttcat cgccgtgggc tacgtggacg acacgcagtt 600
cgtgcggttc gacagcgacg ccgcgagcca gaggatggag ccgcgggcgc cgtggataga 660
gcaggagggg ccggagtatt gggaccagga gacacggaat gtgaaggccc agtcacagac 720
tgaccgagtg gacctgggga ccctgcgcgg ctactacaac cagagcgagg acggtgagtg 780
accccggccc ggggcgcagg tcacgacccc tcatccccca cggacgggcc aggtggccca 840
cagtctccgg gtccgagatc caccccgaag ccgcgggacc ccgagaccct tgccccggga 900
gaggcccagg cgcctttacc cggtttcatt ttcagtttag gccaaaaatc cccccgggtt 960
ggtcggggcc gggcagggct tgggggactg ggctgaccgc ggggtcgggg ccaggttctc 1020
acaccatcca gataatgtat ggctgcgacg tggggccgga cgggcgcttc ctccgcgggt 1080
accggcagga cgcctacgac ggcaaggatt acatcgccct gaacgaggac ctgcgctctt 1140
ggaccgcggc ggacatggca gctcagatca ccaagcgcaa gtgggaggcg gcccatgcgg 1200
cggagcagca gagagcctac ctggagggcc ggtgcgtgga gtggctccgc agatacctgg 1260
agaacgggaa ggagacgctg cagcgcacgg gtaccagggg ccacggggcg cctccctgat 1320
cgcctataga tctcccgggc tggcctccca caaggagggg agacaattgg gaccaacact 1380
agaatatcac cctccctctg gtcctgaggg agaggaatcc tcctgggttt ccagatcctg 1440
taccagagag tgactctgag gttccgccct gctctctgac acaattaagg gataaaatct 1500
ctgaaggagt gacgggaaga cgatccctcg aatactgatg agtggttccc tttgacaccg 1560
gcagcagcct tgggcccgtg acttttcctc tcaggccttg ttctctgctt cacactcaat 1620
gtgtgtgggg gtctgagtcc agcacttctg agtctctcag cctccactca ggtcaggacc 1680
agaagtcgct gttcccttct cagggaatag aagattatcc caggtgcctg tgtccaggct 1740
ggtgtctggg ttctgtgctc tcttccccat cccgggtgtc ctgtccattc tcaagatggc 1800
cacatgcgtg ctggtggagt gtcccatgac agatgcaaaa tgcctgaatt ttctgactct 1860
tcccgtcaga cccccccaag acacatatga cccaccaccc catctctgac catgaggcca 1920
ccctgaggtg ctgggccctg ggcttctacc ctgcggagat cacactgacc tggcagcggg 1980
atggggagga ccagacccag gacacggagc tcgtggagac caggcctgca ggggatggaa 2040
ccttccagaa gtgggcggct gtggtggtgc cttctggaga ggagcagaga tacacctgcc 2100
atgtgcagca tgagggtctg cccaagcccc tcaccctgag atggggtaag gagggagatg 2160
ggggtgtcat gtctcttagg gaaagcagga gcctctctgg agacctttag cagggtcagg 2220
gcccctcacc ttcccctctt ttcccagagc tgtcttccca gcccaccatc cccatcgtgg 2280
gcatcattgc tggcctggtt ctccttggag ctgtgatcac tggagctgtg gtcgctgccg 2340
tgatgtggag gaggaagagc tcaggtggag aaggggtgaa aggtggggtc tgagatttct 2400
tgtctcactg agggttccaa gccccagcta gaaatgtgcc ctgtctcatt actgggaagc 2460
accttccaca atcatgggcc gacccagcct gggccctgtg tgccagcact tactcttttg 2520
taaagcacct gttaaaatga aggacagatt tatcaccttg attacggcgg tgatgggacc 2580
tgataccagc agtcacaagt cacaggggaa ggtccctgag gacagacctc aggagggcta 2640
ttggtccagg acccacacct gctttcttca tgtttcctga tcccgccctg ggtctgcagt 2700
cacacatttc tggaaacttc tctggggtcc aagactagga ggttcctcta ggaccttaag 2760
gccctggctc ctttctggta tctcacagga cattttcttc ccacagatag aaaaggaggg 2820
agttacactc aggctgcaag taagtatgaa ggaggctgat gcctgaggtc cttgggatat 2880
tgtgtttggg agcccatggg ggagctcacc caccccacaa ttcctcctct agccacatct 2940
tctgtgggat ctgaccaggt tctgtttttg ttctacccca ggcagtgaca gtgcccaggg 3000
ctctgatgtg tctctcacag cttgtaaagg tgagagcttg gagggcctga tgtgtgttgg 3060
gtgttgggcg gaacagtgga cacagctgtg ctatggggtt tctttgcatt ggatgtattg 3120
agcatgcgat gggctgttta aggtgtgacc cctcactgtg atggatatga atttgttcat 3180
gaatattttt ttctatagtg tgagacagct gccttgtgtg ggactgagag gcaagagttg 3240
ttcctgccct tccctttgtg acttgaagaa ccctgacttt gtttctgcaa aggcacctgc 3300
atgtgtctgt gttcgtgtag gcataatgtg aggaggtggg gagaccaccc caccccgatg 3360
tccaccatga ccctcttccc acgctgacct gtgctccctc tccaatcatc tttcctgttc 3420
cagagaggtg gggctgaggt gtctccatct ctgtctcaac ttcatggtgc actgagctgt 3480
aacttcttcc ttccctatta aaa 3503

<210> SEQ ID NO 58
<211> LENGTH: 3502
<212> TYPE: DNA
<213> ORGANISM: Artificial Sequence
<220> FEATURE:
<223> OTHER INFORMATION: HLA-A240201 nucleotide sequence

<400> SEQUENCE: 58
cagaagcaga ggggtcaggg cgaagtccca gggccccagg cgtggctctc agggtctcag 60
gccccgaagg cggtgtatgg attggggagt cccagccttg gggattcccc aactccgcag 120
tttcttttct ccctctccca acctatgtag ggtccttctt cctggatact cacgacgcgg 180
acccagttct cactcccatt gggtgtcggg tttccagaga agccaatcag tgtcgtcgcg 240
gtcgctgttc taaagtccgc acgcacccac cgggactcag attctcccca gacgccgagg 300
atggccgtca tggcgccccg aaccctcgtc ctgctactct cgggggccct ggccctgacc 360
cagacctggg caggtgagtg cggggtcggg agggaaacgg cctctgcggg gagaagcaag 420
gggcccgcct ggcgggggcg caagacccgg gaagccgcgc cgggaggagg gtcgggcggg 480
tctcagccac tcctcgtccc caggctccca ctccatgagg tatttctcca catccgtgtc 540
ccggcccggc cgcggggagc cccgcttcat cgccgtgggc tacgtggacg acacgcagtt 600

-continued

```
cgtgcggttc gacagcgacg ccgcgagcca gaggatggag ccgcgggcgc cgtggataga    660
gcaggagggg ccggagtatt gggacgagga gacagggaaa gtgaaggccc actcacagac    720
tgaccgagag aacctgcgga tcgcgctccg ctactacaac cagagcgagg ccggtgagtg    780
accccggccc ggggcgcagg tcacgacccc tcatccccca cggacgggcc gggtcgccca    840
cagtctccgg gtccgagatc caccccgaag ccgcgggacc ccgagaccct tgccccggga    900
gaggcccagg cgccttaacc cggtttcatt ttcagtttag gccaaaaatc cccccgggtt    960
ggtcggggcc gggcggggct cgggggactg ggctgaccgc ggggtcgggg ccaggttctc   1020
acaccctcca gatgatgttt ggctgcgacg tggggtcgga cgggcgcttc ctccgcgggt   1080
accaccagta cgcctacgac ggcaaggatt acatcgccct gaaagaggac ctgcgctctt   1140
ggaccgcggc ggacatggcg gctcagatca ccaagcgcaa gtgggaggcg gcccatgtgg   1200
cggagcagca gagagcctac ctggagggca cgtgcgtgga cgggctccgc agatacctgg   1260
agaacgggaa ggagacgctg cagcgcacgg gtaccagggg ccacggggcg cctacctgat   1320
cgcctgtagg tctcccgggc tggcctccca caaggagggg agacaattgg gaccaacact   1380
agaatatcgc cctccctctg gtcctgaggg agaggaatcc tcctgggttt ccagatcctg   1440
taccagagag tgactctgag gttccgccct gctctctgac acaattaagg gataaaatct   1500
ctgacggaat gacggaaaga cgatccctcg aatactgatg actggttccc tttgacaccg   1560
gcagcagcct tgggaccgtg acttttcctc tcaggccttg ttctctgctt cacactcaat   1620
gtgtgtgggg gtctgagtcc agcacttctg agtccctcag cctccactca ggtcaggacc   1680
agaagtcgct gttccctcct cagggaatag aagattatcc caggtgcctg tgtccaggct   1740
ggtgtctggg ttctgtgctc tcttccccat cccgggtgtc ctgtccattc tcaagatggc   1800
cacatgcatg ctggtggagt gtcccatgac agatgcaaaa tgcctgaatt ttctgactct   1860
tcccgtcaga cccccccaag acacatatga cccaccaccc catctctgac catgaggcca   1920
ctctgagatg ctgggccctg ggcttctacc ctgcggagat cacactgacc tggcagcggg   1980
atggggagga ccagacccag gacacggagc ttgtggagac caggcctgca ggggatggaa   2040
ccttccagaa gtgggcagct gtggtggtac cttctggaga ggagcagaga tacacctgcc   2100
atgtgcagca tgagggtctg cccaagcccc tcaccctgag atggggtaag gagggagatg   2160
ggggtgtcat gtctcttagg gaaagcagga gcctctctgg agacctttag cagggtcagg   2220
gcccctcacc ttcccctctt ttcccagagc catcttccca gcccaccgtc cccatcgtgg   2280
gcatcattgc tggcctggtt ctccttggag ctgtgatcac tggagctgtg gtcgctgctg   2340
tgatgtggag gaggaacagc tcaggtggag aaggggtgaa gggtggggtc tgagatttct   2400
tgtctcactg agggttccaa gccccagcta gaaatgtgcc ctgtctcatt actgggaagc   2460
accatccaca atcatgggcc gacccagcct gggccctgtg tgccagcact tactcttttg   2520
taaagcacct gtgacaatga aggacagatt tatcaccttg attatggcgg tgatgggacc   2580
tgatcccagc agtcacaagt cacaggggaa ggtccctgac gacagatctc aggagggcga   2640
ttggtccagg gcccacatct gctttcttca tgtttcctga tcctgccctg ggtctgcagt   2700
cacacatttc tggaaacttc tctggggtcc aagactagga ggttcctcta ggaccttaag   2760
gccctggctc ctttctggta tctcacagga catttcttc ccacagatag aaaaggaggg   2820
agctactctc aggctgcaag taagtatgaa ggaggctgat gcctgaggtc cttgggatat   2880
tgtgtttggg agcccatggg ggagctcaac caccccacaa ttcctcctct agccacatct   2940
tctgtgggat ctgaccaggt tctgtttttg ttctacccca ggcagtgaca gtgcccaggg   3000
```

```
ctctgatgtg tctctcacag cttgtaaagg tgagagcttg gagggcctga tgtgtgttgg   3060

gtgttgggcg gaacagtgga cacagctgtg ctatggggtt tctttgcatt ggatgtattg   3120

agcatgcgat gggctgttta aagtgtgacc cctcactgtg acagatatga agttgttcat   3180

gaattttttt tctatagtgt gagacagctg ccttgtgtgg gactgagagg caagagttgt   3240

tcctgccctt ccctttgtga cttgaagaac cctgactttg tttctgcaaa ggcacctgca   3300

tgtgtctgtg ttcatgtagg cataatgtga ggaggtgggg agaccacccc acccccatgt   3360

ccaccatgac cctcttccca cgctgacctg tgctccctcc ccaatcatct ttcctgttgc   3420

agagaggtgg ggctgaggtg tctccatctc tgtctcaact tcatggtgca ctgagctgta   3480

acttcttcct tccctattaa aa                                            3502
```

```
<210> SEQ ID NO 59
<211> LENGTH: 3503
<212> TYPE: DNA
<213> ORGANISM: Artificial Sequence
<220> FEATURE:
<223> OTHER INFORMATION: HLA-A30010101 nucleotide sequence

<400> SEQUENCE: 59

caggagcaga ggggtcaggg cgaagtccca gggccccagg cgtggctctc agggtctcag     60

gccccgaagg cggtgtatgg attggggagt cacagccttg ggattcccc aactccgcag    120

tttcttttct ccctctccca acctacgtag ggtccttcat cctggatact cacgacgcgg    180

acccagttct cactcccatt gggtgtcggg tttccagaga agccaatcag tgtcgtcgcg    240

gtcgctgttc taaagcccgc acgcacccac cgggactcag attctcccca gacgccgagg    300

atggccgtca tggcgccccg aaccctcctc ctgctactct cgggggccct ggccctgacc    360

cagacctggg cgggtgagtg cggggtcggg agggaaaccg cctctgcggg gagaagcaag    420

gggccctcct ggcgggggcg caggaccggg ggagccgcgc cgggaggagg gtcggtcagg    480

tctcagccac tgctcgcccc caggctccca ctccatgagg tatttctcca catccgtgtc    540

ccggcccggc agtggagagc cccgcttcat cgcagtgggc tacgtggacg acacgcagtt    600

cgtgcggttc gacagcgacg ccgcgagcca gaggatggag ccgcgggcgc cgtggataga    660

gcaggagagg cctgagtatt gggaccagga gacacggaat gtgaaggccc agtcacagac    720

tgaccgagtg gacctgggga ccctgcgcgg ctactacaac cagagcgagg ccggtgagtg    780

accccggccg gggcgcaggt cacgaccccc tcatccccca cggacgggcc aggtcgccca    840

cagtctccgg gtccgagatc caccccgaag ccgcgggacc ccgagaccct tgacccggga    900

gaggcccagg cgcctttacc cggtttcatt ttcagtttag gccaaaaatt cccccgggtt    960

ggtcggggct gggcggggct cgggggactg ggctgaccgc ggggtcgggg ccaggttctc   1020

acaccatcca gataatgtat ggctgcgacg tggggtcgga cgggcgcttc ctccgcgggt   1080

atgaacagca cgcctacgac ggcaaggatt acatcgccct gaacgaggac ctgcgctctt   1140

ggaccgcggc ggacatggcg gctcagatca cccagcgcaa gtgggaggcg gcccgttggg   1200

cggagcagtt gagagcctac ctggagggca cgtgcgtgga gtggctccgc agatacctgg   1260

agaacgggaa ggagacgctg cagcgcacgg gtaccagggg ccacggggcg ccttcctgat   1320

cgcctgtaga tctcccgggc tggcctccca caaggagggg agacaattgg gaccaacact   1380

agaatatcac cctccctctg gtcctgaggg agaggaatcc tcctgggttt ccagatcctg   1440

taccagagag tgactctgag gttccgccct gctctctgac acaattaagg gataaaatct   1500
```

```
ctgaaggagt gacgggaaga cgatccctcg aatactgatg agtggttccc tttgacaccg   1560

gcagcagcct tgggcccgtg acttttcctc tcaggccttg ttctctgctt cacactcaat   1620

gtgtgtgggg gtctgagtcc agcacttctg agtccctcag cctccactca ggtcaggacc   1680

agaagtcgct gttcccttct cagggaatag aagattatcc caggtgcctg tgtccaggct   1740

ggtgtctggg ttctgtgctc tcttccccat cccgggtgtc ctgtccattc tcaagatggc   1800

cacatgcgtg ctggtggagt gtcccatgac agatgcaaaa tgcctgaatt ttctgactct   1860

tcccgtcaga cccccccaag acacatatga cccaccaccc catctctgac catgaggcca   1920

ccctgaggtg ctgggccctg ggcttctacc ctgcggagat cacactgacc tggcagcggg   1980

atggggagga ccagacccag gacacggagc tcgtggagac caggcctgca ggggatggaa   2040

ccttccagaa gtgggcggct gtggtggtgc cttctggaga ggagcagaga tacacctgcc   2100

atgtgcagca tgagggtctg cccaagcccc tcaccctgag atggggtaag gagggagatg   2160

ggggtgtcat gtctcttagg gaaagcagga gcctctctgg agacctttag cagggtcagg   2220

gcccctcacc ttcccctctt ttcccagagc tgtcttccca gcccaccatc cccatcgtgg   2280

gcatcattgc tggcctggtt ctccttggag ctgtgatcac tggagctgtg gtcgctgccg   2340

tgatgtggag gaggaagagc tcaggtggag aaggggtgaa gggtggggtc tgagatttct   2400

tgtctcactg agggttccaa gccccagcta gaaatgtgcc ctgtctcatt actgggaagc   2460

accatccaca atcatgggcc tacccagcct gggccctgtg tgccagcact tactcttttg   2520

taaagcacct gttaaaatga aggacagatt tatcaccttg attacggcgg tgatgggacc   2580

tgatcccagc agtcacaagt cacaggggaa ggtccctgag gacagacctc aggagggcta   2640

ttggtccagg acccacacct gctttcttca tgtttcctga tcccgccctg ggtctgcagt   2700

cacacatttc tggaaacttc tctggggtcc aagactagga ggttcctcta ggaccttaag   2760

gccctggctc ctttctggta tctcacagga cattttcttc tcacagatag aaaaggaggg   2820

agttacactc aggctgcaag taagtatgaa ggaggctgat gcctgaggtc cttgggatat   2880

tgtgtttggg agcccatggg ggagctcacc caccccacaa ttcctcctct agccacatct   2940

tctgtgggat ctgaccaggt tctgtttttg ttctacccca ggcagtgaca gtgcccaggg   3000

ctctgatgtg tctctcacag cttgtaaagg tgagagcttg gaggacctaa tgtgtgttgg   3060

gtgttgggcg gaacagtgga cacagctgtg ctatggggtt tctttgcatt ggatgtattg   3120

agcatgcgat gggctgttta aggtgtgacc cctcactgtg atggatatga atttgttcat   3180

gaatattttt ttctatagtg tgagacagct gccttgtgtg ggactgagag gcaagagttg   3240

ttcctgccct tccctttgtg acttgaagaa ccctgacttt gtttctgcaa aggcacctgc   3300

atgtgtctgt gttcgtgtag gcataatgtg aggaggtggg gagaccaccc cacccccatg   3360

tccaccatga ccctcttccc acgctgacct gtgctccctc cccaatcatc tttcctgttc   3420

cagagaggtg gggctgaggt gtctccatct ctgtctcaac ttcatggtgc actgagctgt   3480

aacttcttcc ttccctatta aaa                                           3503
```

<210> SEQ ID NO 60
<211> LENGTH: 3518
<212> TYPE: DNA
<213> ORGANISM: Artificial Sequence
<220> FEATURE:
<223> OTHER INFORMATION: HLA-A33010101 nucleotide sequence

<400> SEQUENCE: 60
caggagcaga ggggtcaggg cgaagtacca gggccccagg cgtggctctc agggtctcag 60
gccccgaagg cggtgtatgg attggggagt cccagccttg ggattcccc aactccgcag 120 tttcttttct ccctctccca acctatgtag ggtccttctt cctggatact cacgacgcgg 180
acccagttct cactcccatt gggtgtcggg tttccagaga agccaatcag tgtcgtcgcg 240
gtcgcggttc taaagtccgc acgcacccac cgggactcag attctcccca gacgccgagg 300
atggccgtca tggcgccccg aaccctcctc ctgctactct tgggggccct ggccctgacc 360
cagacctggg cgggtgagtg cggggtcgtg gggaaaccgc ctctgcgggg agaagcaagg 420
ggcccgcccg gcgggggcgc aggacccggg tagccgcgcc gggaggaggg tcgggcggat 480
ctcagccact cctcgccccc aggctcccac tccatgaggt atttcaccac atccgtgtcc 540
cggcccggcc gcggggagcc ccgcttcatc gccgtgggct acgtggacga cacgcagttc 600
gtgcggttcg acagcgacgc cgcgagccag aggatggagc cgcgggcgcc gtggatagag 660
caggaggggc cggagtattg ggaccggaac acacggaatg tgaaggccca ctcacagatt 720
gaccgagtgg acctggggac cctgcgcggc tactacaacc agagcgaggc cggtgagtga 780
ccccagcccg gggcgcaggt cacgacctct catcccccac ggacgggcca ggtcacccac 840
agtctccggg tccgagatcc accccgaagc cgcgggaccc cgagaccctt gccccgggag 900
aggcccaggc gcctttaccc ggtttcattt tcagtttagg ccaaaaatcc ccccgggttg 960
gtcggggccg gacggggctc gggggactgg gctgaccgtg gggtcggggc caggttctca 1020
caccatccag atgatgtatg gctgcgacgt ggggtcggac gggcgcttcc tccgcgggta 1080
ccagcaggac gcctacgacg gcaaggatta catcgccttg aacgaggacc tgcgctcttg 1140
gaccgcggcg gacatggcgg ctcagatcac ccagcgcaag tgggaggcgg cccgtgtggc 1200
ggagcagttg agagcctacc tggagggcac gtgcgtggag tggctccgca gacacctgga 1260
gaacgggaag gagacgctgc agcgcacggg taccaggggc cacggggcgc ctccctgatc 1320
gcctgtagat ctcccgggct ggcctcccac aaggaggga gacaattggg accaacacta 1380
gaatatcacc ctccctctgg tcctgaggga gaggaatcct cctgggtttc cagatcctgt 1440
accagagagt gactctgagg ttccgccctg ctctgtgaca caattaaggg ataaaatctc 1500
tgaaggaatg acgggaagac gatccctcga atactgatga gtggttccct ttgacacaca 1560
ccggcagcag ccttgggccc gtgacttttc ctctcaggcc ttgttctctg cttcacactc 1620
aatgtgtgtg ggggtctgag tccagcactt ctgagtccct cagcctccac tcaggtcagg 1680
accagaagtc gctgttccct cttcagggac tagaattttc cacggaatag gagattatcc 1740
caggtgcctg tgtccaggct ggtgtctggg ttctgtgctc ccttccccat cccaggtgtc 1800
ctgtccattc tcaagatagc cacatgtgtg ctggaggagt gtcccattac agatgcaaaa 1860
tgcctgaatg ttctgactct tcctgacaga cccccccagg acgcatatga ctcaccacgc 1920
tgtctctgac catgaggcca ccctgaggtg ctgggccctg agcttctacc ctgcggagat 1980
cacactgacc tggcagcggg atggggagga ccagacccag gacacggagc tcgtggagac 2040
caggcctgca ggggatggaa ccttccagaa gtgggcgtct gtggtggtgc cttctggaca 2100
ggagcagaga tacacctgcc atgtgcagca tgagggtctc cccaagcccc tcaccctgag 2160
atggggtaag gagggagatg ggggtgtcat gtcttttagg gaaagcagga gcctctctga 2220
cctttagcag ggtcagggcc cctcaccttc ccctcttttc ccagagccgt cttcccagcc 2280
caccatcccc atcgtgggca tcattgctgg cctagttctc tttggagctg tgttcgctgg 2340
agctgtggtc gctgctgtga ggtggaggag gaagagctca ggtggggtga aggggtgaag 2400
ggtgggtctg agatttcttg tctcactgag ggttccaaga cccaggtaga agtgtgccct 2460
gcctcgttac tgggaagcac catccacaat tatgggccta cccagcctgg gccctgtgtg 2520
ccagcactta ctcttttgta aagcacctgt taaaatgaag gacagattta tcaccttgat 2580
tatggcggtg atgggacctg atcccagcag tcacaagtca caggggaagg tccctgagga 2640
ccttcaggag ggcggttggt ccaggaccca cacctgcttt cttcatgttt cctgatcccg 2700
ccctgggtct gcagtcacac atttctggaa acttctctga ggtccaagac ttggaggttc 2760
ctctaggacc ttaaggccct ggctcctttc tggtatctca caggacattt tcttcccaca 2820
gatagaaaag gagggagcta ctctcaggct gcaagtaagt atgaaggagg atgatccaag 2880
aaatcactgg gatattgtgt ttgggagccc gtgggggagc tcacccaccc cacaattcct 2940
cctctagcca catcttctgt gggatctgac caggttctgt tttgtcccta ccccaggcag 3000
tgacagtgcc cagggctctg atatgtctct cacagcttgt aaaggtgaga gcctggaggg 3060
cctgatgtgt gttgggtgtt gggcggaaca gtggacgcag ctgtgctatg ggtttcttt 3120 gcattggatg tattgagcat gcgatgggct gtttaaagtg tgactcctca ctgtgacaga 3180
tacgaatttg ttcatgaata tttttttcta tagtgtgaga cagctgcctt gtgtgggact 3240
gagaggcaag atttgttcct gcccttccct ttgtgacttg aagtaccctg actttgtttc 3300
tgcaaaggca cctgcatgtg tctgtgttct tgtaggcata atgtgaggag gtggggagac 3360
caccccaccc ccatgtccac catgaccctc ttcccacgct gacctgtgct ccctccccaa 3420
tcatctttcc tgttccagag aggtggggct gaggtgtctc catctctgcc tcaacttcat 3480
ggtgcactga gctgtaactt cttccttccc tattaaaa 3518

<210> SEQ ID NO 61
<211> LENGTH: 3502
<212> TYPE: DNA
<213> ORGANISM: Artificial Sequence
<220> FEATURE:
<223> OTHER INFORMATION: HLA-A03010101 nucleotide sequence

<400> SEQUENCE: 61
caggagcaga ggggtcaggg cgaagtccca gggccccagg cgtggctctc agagtctcag 60
gccccgaagg cggtgtatgg attggggagt cccagccttg gggattcccc aactccgcag 120
tttcttttct ccctctccca acctacgtag ggtccttcat cctggatact cacgacgcgg 180
acccagttct cactcccatt gggtgtcggg tttccagaga agccaatcag tgtcgtcgcg 240
gtcgctgttc taaagcccgc acgcacccac cgggactcag attctcccca gacgccgagg 300
atggccgtca tggcgccccg aaccctcctc ctgctactct cgggggccct ggccctgacc 360
cagacctggg cgggtgagtg cggggtcggg agggaaaccg cctctgcggg gagaagcaag 420
gggccctcct ggcgggggcg caggaccggg ggagccgcgc cgggacgagg gtcgggcagg 480
tctcagccac tgctcgcccc caggctccca ctccatgagg tatttcttca catccgtgtc 540
ccggcccggc cgcggggagc cccgcttcat cgccgtgggc tacgtggacg acacgcagtt 600
cgtgcggttc gacagcgacg ccgcgagcca gaggatggag ccgcgggcgc cgtggataga 660
gcaggagggg ccggagtatt gggaccagga gacacggaat gtgaaggccc agtcacagac 720
tgaccgagtg gacctgggga ccctgcgcgg ctactacaac cagagcgagg ccggtgagtg 780
accccggccg gggcgcaggg tcaggacccc tcatccccca cggacgggcc aggtcgccca 840

```
cagtctccgg gtccgagatc caccccgaag ccgcgggacc ccgagaccct tgccccggga    900
gaggcccagg cgcctttacc cggtttcatt ttcagtttag gccaaaaatc cccccgggtt    960
ggtcggggct gggcggggct cgggggactg ggctgaccgc ggggtcgggg ccaggttctc   1020
acaccatcca gataatgtat ggctgcgacg tggggtcgga cgggcgcttc ctccgcgggt   1080
accggcagga cgcctacgac ggcaaggatt acatcgccct gaacgaggac ctgcgctctt   1140
ggaccgcggc ggacatggcg gctcagatca ccaagcgcaa gtgggaggcg gcccatgagg   1200
cggagcagtt gagagcctac ctggatggca cgtgcgtgga gtggctccgc agatacctgg   1260
agaacgggaa ggagacgctg cagcgcacgg gtaccagggg ccacggggcg cctccctgat   1320
cgcctgtaga tctcccgggc tggcctccca caaggagggg agacaattgg gaccaacact   1380
agaatatcac cctccctctg gtcctgaggg agaggaatcc tcctgggttc cagatcctgt   1440
accagagagt gactctgagg ttccgccctg ctctctgaca caattaaggg ataaaatctc   1500
tgaaggagtg acgggaagac gatccctcga atactgatga gtggttccct ttgacaccgg   1560
cagcagcctt gggcccgtga cttttcctct caggccttgt tctctgcttc acactcaatg   1620
tgtgtggggg tctgagtcca gcacttctga gtccctcagc ctccactcag gtcaggacca   1680
gaagtcgctg ttcccttctc agggaataga agattatccc aggtgcctgt gtccaggctg   1740
gtgtctgggt tctgtgctct cttccccatc ccgggtgtcc tgtccattct caagatggcc   1800
acatgcgtgc tggtggagtg tcccatgaca gatgcaaaat gcctgaattt tctgactctt   1860
cccgtcagac ccccccaaga cacatatgac ccaccacccc atctctgacc atgaggccac   1920
cctgaggtgc tgggccctgg gcttctaccc tgcggagatc acactgacct ggcagcggga   1980
tggggaggac cagacccagg acacggagct cgtggagacc aggcctgcag gggatggaac   2040
cttccagaag tgggcggctg tggtggtgcc ttctggagag gagcagagat acacctgcca   2100
tgtgcagcat gagggtctgc ccaagcccct caccctgaga tggggtaagg agggagatgg   2160
gggtgtcatg tctcttaggg aaagcaggag cctctctgga gacctttagc agggtcaggg   2220
cccctcacct tcccctcttt tcccagagct gtcttcccag cccaccatcc ccatcgtggg   2280
catcattgct ggcctggttc tccttggagc tgtgatcact ggagctgtgg tcgctgccgt   2340
gatgtggagg aggaagagct caggtggaga aggggtgaag ggtggggtct gagatttctt   2400
gtctcactga gggttccaag ccccagctag aaatgtgccc tgtctcatta ctgggaagca   2460
ccgtccacaa tcatgggcct acccagtctg ggccctgtgt gccagcactt actcttttgt   2520
aaagcacctg ttaaaatgaa ggacagattt atcaccttga ttacggcggt gatgggacct   2580
gatcccagca gtcacaagtc acaggggaag gtccctgagg acagacctca ggagggctat   2640
tggtccagga cccacacctg ctttcttcat gtttcctgat cccgccctgg gtctgcagtc   2700
acacatttct ggaaacttct ctggggtcca agactaggag gttcctctag gaccttaagg   2760
ccctggctcc tttctggtat ctcacaggac attttcttct cacagataga aaaggaggga   2820
gttacactca ggctgcaagt aagtatgaag gaggctgatg cctgaggtcc ttgggatatt   2880
gtgtttggga gcccatgggg gagcccaccc acctcacaat tcctcctcta gccacatctt   2940
ctgtgggatc tgaccaggtt ctgtttttgt tctaccccag gcagtgacag tgcccagggc   3000
tctgatgtgt ccctcacagc ttgtaaaggt gagagcttgg aggacctaat gtgtgttggg   3060
tgttgggcgg aacagtggac acagctgtgc tatggggttt ctttgcattg gatgtattga   3120
gcatgcgatg ggctgtttaa ggtgtgaccc ctcactgtga tggatatgaa tttgttcatg   3180
```

aatatttttt tctatagtgt gagacagctg ccttgtgtgg gactgagagg caagagttgt 3240
tcctgccctt ccctttgtga cttgaagaac cctgactttg tttctgcaaa ggcacctgca 3300
tgtgtctgtg ttcgtgtagg cataatgtga ggaggtgggg agaccacccc acccccatgt 3360
ccaccatgac cctcttccca cgctgacctg tgctccctcc ccaatcatct ttcctgttcc 3420
agagaggtgg ggctgaggtg tctccatctc tgtctcaact tcatggtgca ctgagctgta 3480
acttcttcct tccctattaa aa 3502

<210> SEQ ID NO 62
<211> LENGTH: 3503
<212> TYPE: DNA
<213> ORGANISM: Artificial Sequence
<220> FEATURE:
<223> OTHER INFORMATION: HLA-A01010101 nucleotide sequence

<400> SEQUENCE: 62
caggagcaga ggggtcaggg cgaagtccca gggccccagg cgtggctctc agggtctcag 60
gccccgaagg cggtgtatgg attggggagt cccagccttg gggattcccc aactccgcag 120
tttcttttct ccctctccca acctacgtag ggtccttcat cctggatact cacgacgcgg 180
acccagttct cactcccatt gggtgtcggg tttccagaga agccaatcag tgtcgtcgcg 240
gtcgctgttc taaagtccgc acgcacccac cgggactcag attctcccca gacgccgagg 300
atggccgtca tggcgccccg aaccctcctc ctgctactct cggggggccct ggccctgacc 360 cagacctggg cgggtgagtg cggggtcggg agggaaaccg cctctgcggg gagaagcaag 420
gggccctcct ggcgggggcg caggaccggg ggagccgcgc cgggaggagg gtcgggcagg 480
tctcagccac tgctcgcccc caggctccca ctccatgagg tatttcttca catccgtgtc 540
ccggcccggc cgcggggagc cccgcttcat cgccgtgggc tacgtggacg acacgcagtt 600
cgtgcggttc gacagcgacg ccgcgagcca gaagatggag ccgcgggcgc cgtggataga 660
gcaggagggg ccggagtatt gggaccagga gacacggaat atgaaggccc actcacagac 720
tgaccgagcg aacctgggga ccctgcgcgg ctactacaac cagagcgagg acggtgagtg 780
accccggccc ggggcgcagg tcacgacccc tcatccccca cggacgggcc aggtcgccca 840
cagtctccgg gtccgagatc caccccgaag ccgcgggact ccgagaccct tgtcccggga 900
gaggcccagg cgcctttacc cggtttcatt ttcagtttag gccaaaaatc cccccgggtt 960
ggtcggggcg gggcggggct cgggggactg ggctgaccgc ggggtcgggg ccaggttctc 1020
acaccatcca gataatgtat ggctgcgacg tggggccgga cgggcgcttc ctccgcgggt 1080
accggcagga cgcctacgac ggcaaggatt acatcgccct gaacgaggac ctgcgctctt 1140
ggaccgcggc ggacatggca gctcagatca ccaagcgcaa gtgggaggcg gtccatgcgg 1200
cggagcagcg gagagtctac ctggagggcc ggtgcgtgga cgggctccgc agatacctgg 1260
agaacgggaa ggagacgctg cagcgcacgg gtaccagggg ccacggggcg cctccctgat 1320
cgcctataga tctcccgggc tggcctccca caaggagggg agacaattgg gaccaacact 1380
agaatatcac cctccctctg gtcctgaggg agaggaatcc tcctgggttt ccagatcctg 1440
taccagagag tgactctgag gttccgccct gctctctgac acaattaagg gataaaatct 1500
ctgaaggagt gacgggaaga cgatccctcg aatactgatg agtggttccc tttgacaccg 1560
gcagcagcct tgggcccgtg acttttcctc tcaggccttg ttctctgctt cacactcaat 1620
gtgtgtgggg gtctgagtcc agcacttctg agtctctcag cctccactca ggtcaggacc 1680
agaagtcgct gttcccttct cagggaatag aagattatcc caggtgcctg tgtccaggct 1740

```
ggtgtctggg ttctgtgctc tcttccccat cccgggtgtc ctgtccattc tcaagatggc   1800

cacatgcgtg ctggtggagt gtcccatgac agatgcaaaa tgcctgaatt ttctgactct   1860

tcccgtcaga cccccccaag acacatatga cccaccaccc catctctgac catgaggcca   1920

ccctgaggtg ctgggccctg ggcttctacc ctgcggagat cacactgacc tggcagcggg   1980

atggggagga ccagacccag gacacggagc tcgtggagac caggcctgca ggggatggaa   2040

ccttccagaa gtgggcggct gtggtggtgc cttctggaga ggagcagaga tacacctgcc   2100

atgtgcagca tgagggtctg cccaagcccc tcaccctgag atggggtaag gagggagatg   2160

ggggtgtcat gtctcttagg gaaagcagga gcctctctgg agacctttag cagggtcagg   2220

gcccctcacc ttcccctctt ttcccagagc tgtcttccca gcccaccatc cccatcgtgg   2280

gcatcattgc tggcctggtt ctccttggag ctgtgatcac tggagctgtg gtcgctgccg   2340

tgatgtggag gaggaagagc tcaggtggag aaggggtgaa gggtggggtc tgagatttct   2400

tgtctcactg agggttccaa gccccagcta gaaatgtgcc ctgtctcatt actgggaagc   2460

accttccaca atcatgggcc gacccagcct gggccctgtg tgccagcact tactcttttg   2520

taaagcacct gttaaaatga aggacagatt tatcaccttg attacggcgg tgatgggacc   2580

tgatcccagc agtcacaagt cacaggggaa ggtccctgag gacagacctc aggagggcta   2640

ttggtccagg acccacacct gctttcttca tgtttcctga tcccgccctg ggtctgcagt   2700

cacacatttc tggaaacttc tctggggtcc aagactagga ggttcctcta ggaccttaag   2760

gccctggctc ctttctggta tctcacagga cattttcttc ccacagatag aaaaggaggg   2820

agttacactc aggctgcaag taagtatgaa ggaggctgat gcctgaggtc cttgggatat   2880

tgtgtttggg agcccatggg ggagctcacc caccccacaa ttcctcctct agccacatct   2940

tctgtgggat ctgaccaggt tctgtttttg ttctacccca ggcagtgaca gtgcccaggg   3000

ctctgatgtg tctctcacag cttgtaaagg tgagagcttg gagggcctga tgtgtgttgg   3060

gtgttgggtg gaacagtgga cacagctgtg ctatggggtt tctttgcgtt ggatgtattg   3120

agcatgcgat gggctgttta aggtgtgacc cctcactgtg atggatatga atttgttcat   3180

gaatattttt ttctatagtg tgagacagct gccttgtgtg ggactgagag gcaagagttg   3240

ttcctgccct tccctttgtg acttgaagaa ccctgacttt gtttctgcaa aggcacctgc   3300

atgtgtctgt gttcgtgtag gcataatgtg aggaggtggg gagagcaccc cacccccatg   3360

tccaccatga ccctcttccc acgctgacct gtgctccctc tccaatcatc tttcctgttc   3420

cagagaggtg gggctgaggt gtctccatct ctgtctcaac ttcatggtgc actgagctgt   3480

aacttcttcc ttccctatta aaa                                           3503
```

<210> SEQ ID NO 63
<211> LENGTH: 3517
<212> TYPE: DNA
<213> ORGANISM: Artificial Sequence
<220> FEATURE:
<223> OTHER INFORMATION: HLA-A26010101 nucleotide sequence

<400> SEQUENCE: 63

```
caggagcaga ggggtcaggg cgaagtccca gggccccagg cgtggctctc agggtctcag     60

gccccgaagg cggtatatgg attggggagt cccagccttg gggattcccc aactccgcag    120

tttcttttct ccctctccca acctatgtag ggtccttctt cctggatact cacgacgcgg    180

acccagttct cactcccatt gggtgtcggg tttccagaga agccaatcag tgtcgtcgcg    240
```

-continued

```
gtcgcggttc taaagtccgc acgcacccac cgggactcag attctcccca gacgccgagg    300
atggccgtca tggcgccccg aaccctcgtc ctgctactct cggggggccct ggccctgacc    360
cagacctggg cgggtgagtg cggggtcggg agggaaacgg cctctgtggg gagaagcaag    420
gggcccgccc ggcgggggcg caggacccgg gaagccgcgc ctggaggagg gtcgggcggg    480
tctcagccac tcctcgcccc caggctccca ctccatgagg tatttctaca cctccgtgtc    540
ccggcccggc cgcggggagc cccgcttcat cgccgtgggc tacgtggacg acacgcagtt    600
cgtgcggttc gacagcgacg ccgcgagcca gaggatggag ccgcgggcgc cgtggataga    660
gcaggagggg ccggagtatt gggaccggaa cacacggaat gtgaaggccc actcacagac    720
tgaccgagcg aacctgggga ccctgcgcgg ctactacaac cagagcgagg acggtgagtg    780
accccggccc ggggcgcagg tcacgacccc tcatccccca cggacgggcc aggtcgccca    840
cagtctccgg gtccgagatc cgccccgaag ccgcgggacc ccgagaccct tgccccggga    900
gaggcccagg cgcctttacc cggtttcatt ttcagtttag gccaaaaatc cccccgggtt    960
ggtcggggcg gggcggggct cgggggaccg ggctgacctc ggggtccggg ccaggttctc   1020
acaccatcca gaggatgtat ggctgcgacg tggggccgga cgggcgcttc ctccgcgggt   1080
accagcagga cgcttacgac ggcaaggatt acatcgccct gaacgaggac ctgcgctctt   1140
ggaccgcggc ggacatggcg gctcagatca cccagcgcaa gtgggagacg gcccatgagg   1200
cggagcagtg gagagcctac ctggagggcc ggtgcgtgga gtggctccgc agatacctgg   1260
agaacgggaa ggagacgctg cagcgcacgg gtaccagggg ccacggggcg cctccctgat   1320
cgcctgtaga tctcccgggc tggcctccca caaggagggg agacaattgg gaccaacact   1380
agaatatcgc cctccctctg gtcctgaggg agaggaatcc tcctgggttt ccagatcctg   1440
taccagagag tgactctgag gttccgccct gctctctgac acaattaagg gataaaatct   1500
ctgaaggaat gacgggaaga cgatccctcg aatactgatg agtggttccc tttgacacac   1560
accggcagca gccttgggcc cgtgactttt cctctcaggc cttgttctct gcttcacact   1620
caatgtgtgt gggggtctga gtccagcact tctgagtccc tcagcctcca ctcaggtcag   1680
gaccagaagt cgctgttccc tcttcaggga ctagaatttt ccacggaata ggagattatc   1740
ccaggtgcct gtgtccaggc tggtgtctgg gttctgtgct cccttcccca tcccaggtgt   1800
cctgtccatt ctcaagatag ccacatgtgt gctggaggag tgtcccatga cagatgcaaa   1860
atgcctgaat gttctgactc ttcctgacag acgcccccaa gacgcatatg actcaccacg   1920
ctgtctctga ccatgaggcc accctgaggt gctgggccct gagcttctac cctgcggaga   1980
tcacactgac ctggcagcgg gatggggagg accagaccca ggacacggag ctcgtggaga   2040
ccaggcctgc aggggatggg accttccaga agtgggcgtc tgtggtggtg ccttctggac   2100
aggagcagag atacacctgc catgtgcagc atgagggtct gcccaagccc ctcaccctga   2160
gatggggtaa ggagggagac gggggtgtca tgtcttttag ggaaagcagg agcctctctg   2220
acctttagca gggtcagggc ccctcacctt cccctctttt cccagagccg tcttcccagc   2280
ccaccatccc catcgtgggc atcattgctg gcctggttct ctttggagct gtgatcgctg   2340
gagctgtggt cgctgctgtg atgtggagga ggaagagctc aggtggggaa gggatgaagg   2400
gtgggtctga gatttcttgt ctcactgagg gttccaagac ccaggtagaa gtgtgccctg   2460
cctcgttact gggaagcacc atccacaatt atgagcctac ccagcctggg ccctgtgtgc   2520
cagcacttac tcttttgtaa agcacctgtt aaaatgaagg acagatttat caccttgatt   2580
acggcggtga tgggacctga tcccagcagt cacaagtcac aggggaaggt ccctgaggac   2640
```

```
cttcaggagg gcggttggtc caggacccac acctgctttc ttcatgtttc ctgatcccgc   2700

cctgggtctg cagtcacaca tttctggaaa cttctctgag gtccaagact tggaggttcc   2760

tctaggacct taaggccctg gctcctttct ggtatctcac aggacatttt cttcccacag   2820

atagaaaagg agggagctac tctcaggctg caagtaagta tgaaggaggc tgatgcctga   2880

ggtccttggg atattgtgtt tgggagcccg tgggggagct cacccacccc acaattcctc   2940

ctctagccac atgttctgtg ggatctgacc aggttctgtt tttgtcctac cccaggcagt   3000

gacagtgccc agggctctga tatgtctctc acagcttgta aaggtgagag cctggagggc   3060

ctgatgtgtg ttgggtgttg ggcggaacag tggacgcagc tgtgctatgg ggtttctttg   3120

cattggatgt attgagcatg cgatgggctg tttaaagtgt gactcctcac tgtgacagat   3180

acgaatttgt tcatgaatat ttttttctat agtgtgagac agctgccttg tgtgggactg   3240

agaggcaaga tttgttcctg cccttccctt tgtgacttga agaaccctga ctttgtttct   3300

gcaaaggcac ctgcatgtgt ctgtgttctt gtaggcataa tgtgaggagg tggggagacc   3360

accccacccc catgtccacc atgaccctct tcccacgctg acctgtgctc cctccccaat   3420

catctttcct gttccagaga ggtggggctg aggtgtctcc atctctgcct caacttcatg   3480

gtgcactgag ctgtaacttt ttccttccct attaaaa                            3517
```

<210> SEQ ID NO 64
<211> LENGTH: 4107
<212> TYPE: DNA
<213> ORGANISM: Artificial Sequence
<220> FEATURE:
<223> OTHER INFORMATION: Cas9 nucleotide sequence

<400> SEQUENCE: 64

```
atggataaga aatactcaat aggcttagat atcggcacaa atagcgtcgg atgggcggtg     60

atcactgatg aatataaggt tccgtctaaa aagttcaagg ttctgggaaa tacagaccgc    120

cacagtatca aaaaaaatct tataggggct cttttatttg acagtggaga gacagcggaa    180

gcgactcgtc tcaaacggac agctcgtaga aggtatacac gtcggaagaa tcgtatttgt    240

tatctacagg agatttttc aaatgagatg gcgaaagtag atgatagttt ctttcatcga     300

cttgaagagt cttttttggt ggaagaagac aagaagcatg aacgtcatcc tatttttgga    360

aatatagtag atgaagttgc ttatcatgag aaatatccaa ctatctatca tctgcgaaaa    420

aaattggtag attctactga taaagcggat ttgcgcttaa tctatttggc cttagcgcat    480

atgattaagt ttcgtggtca tttttttgatt gagggagatt taaatcctga taatagtgat   540

gtggacaaac tatttatcca gttggtacaa acctacaatc aattatttga agaaaaccct    600

attaacgcaa gtggagtaga tgctaaagcg attctttctg cacgattgag taaatcaaga    660

cgattagaaa atctcattgc tcagctcccc ggtgagaaga aaaatggctt atttgggaat    720

ctcattgctt tgtcattggg tttgacccct aattttaaat caaattttga tttggcagaa    780

gatgctaaat tacagctttc aaaagatact tacgatgatg atttagataa tttattggcg    840

caaattggag atcaatatgc tgatttgttt ttggcagcta agaatttatc agatgctatt    900

ttactttcag atatcctaag agtaaatact gaaataacta aggctcccct atcagcttca    960

atgattaaac gctacgatga acatcatcaa gacttgactc ttttaaaagc tttagttcga   1020

caacaacttc cagaaaagta taaagaaatc ttttttgatc aatcaaaaaa cggatatgca   1080

ggttatattg atgggggagc tagccaagaa gaattttata aatttatcaa accaatttta   1140
```

```
gaaaaaatgg atggtactga ggaattattg gtgaaactaa atcgtgaaga tttgctgcgc   1200
aagcaacgga cctttgacaa cggctctatt ccccatcaaa ttcacttggg tgagctgcat   1260
gctattttga gaagacaaga agacttttat ccatttttaa aagacaatcg tgagaagatt   1320
gaaaaaatct tgacttttcg aattccttat tatgttggtc cattggcgcg tggcaatagt   1380
cgttttgcat ggatgactcg gaagtctgaa gaaacaatta ccccatggaa ttttgaagaa   1440
gttgtcgata aaggtgcttc agctcaatca tttattgaac gcatgacaaa ctttgataaa   1500
aatcttccaa atgaaaaagt actaccaaaa catagtttgc tttatgagta ttttacggtt   1560
tataacgaat tgacaaaggt caaatatgtt actgaaggaa tgcgaaaacc agcatttctt   1620
tcaggtgaac agaagaaagc cattgttgat ttactcttca aaacaaatcg aaaagtaacc   1680
gttaagcaat taaaagaaga ttatttcaaa aaaatagaat gttttgatag tgttgaaatt   1740
tcaggagttg aagatagatt taatgcttca ttaggtacct accatgattt gctaaaaatt   1800
attaaagata aagatttttt ggataatgaa gaaaatgaag atatcttaga ggatattgtt   1860
ttaacattga ccttatttga agatagggag atgattgagg aaagacttaa aacatatgct   1920
cacctctttg atgataaggt gatgaaacag cttaaacgtc gccgttatac tggttgggga   1980
cgtttgtctc gaaaattgat taatggtatt agggataagc aatctggcaa aacaatatta   2040
gatttttga aatcagatgg ttttgccaat cgcaatttta tgcagctgat ccatgatgat   2100
agtttgacat ttaaagaaga cattcaaaaa gcacaagtgt ctggacaagg cgatagttta   2160
catgaacata ttgcaaattt agctggtagc cctgctatta aaaaaggtat tttacagact   2220
gtaaaagttg ttgatgaatt ggtcaaagta atggggcggc ataagccaga aaatatcgtt   2280
attgaaatgg cacgtgaaaa tcagacaact caaaagggcc agaaaaattc gcgagagcgt   2340
atgaaacgaa tcgaagaagg tatcaaagaa ttaggaagtc agattcttaa agagcatcct   2400
gttgaaaata ctcaattgca aaatgaaaag ctctatctct attatctcca aaatggaaga   2460
gacatgtatg tggaccaaga attagatatt aatcgtttaa gtgattatga tgtcgatcac   2520
attgttccac aaagtttcct taaagacgat tcaatagaca ataaggtctt aacgcgttct   2580
gataaaaatc gtggtaaatc ggataacgtt ccaagtgaag aagtagtcaa aaagatgaaa   2640
aactattgga gacaacttct aaacgccaag ttaatcactc aacgtaagtt tgataattta   2700
acgaaagctg aacgtggagg tttgagtgaa cttgataaag ctggttttat caaacgccaa   2760
ttggttgaaa ctcgccaaat cactaagcat gtggcacaaa ttttggatag tcgcatgaat   2820
actaaatacg atgaaaatga taaacttatt cgagaggtta aagtgattac cttaaaatct   2880
aaattagttt ctgacttccg aaaagatttc caattctata aagtacgtga gattaacaat   2940
taccatcatg cccatgatgc gtatctaaat gccgtcgttg gaactgcttt gattaagaaa   3000
tatccaaaac ttgaatcgga gtttgtctat ggtgattata aagtttatga tgttcgtaaa   3060
atgattgcta agtctgagca agaaataggc aaagcaaccg caaaatattt cttttactct   3120
aatatcatga acttcttcaa aacagaaatt acacttgcaa atggagagat tcgcaaacgc   3180
cctctaatcg aaactaatgg ggaaactgga gaaattgtct gggataaagg gcgagatttt   3240
gccacagtgc gcaaagtatt gtccatgccc caagtcaata ttgtcaagaa aacagaagta   3300
cagacaggcg gattctccaa ggagtcaatt ttaccaaaaa gaaattcgga caagcttatt   3360
gctcgtaaaa aagactggga tccaaaaaaa tatggtggtt ttgatagtcc aacggtagct   3420
tattcagtcc tagtggttgc taaggtggaa aaagggaaat cgaagaagtt aaaatccgtt   3480
aaagagttac tagggatcac aattatggaa agaagttcct ttgaaaaaaa tccgattgac   3540
```

tttttagaag ctaaaggata taaggaagtt aaaaaagact taatcattaa actacctaaa 3600
tatagtcttt ttgagttaga aaacggtcgt aaacggatgc tggctagtgc cggagaatta 3660
caaaaaggaa atgagctggc tctgccaagc aaatatgtga attttttata tttagctagt 3720
cattatgaaa agttgaaggg tagtccagaa gataacgaac aaaaacaatt gtttgtggag 3780
cagcataagc attatttaga tgagattatt gagcaaatca gtgaattttc taagcgtgtt 3840
attttagcag atgccaattt agataaagtt cttagtgcat ataacaaaca tagagacaaa 3900
ccaatacgtg aacaagcaga aaatattatt catttattta cgttgacgaa tcttggagct 3960
cccgctgctt ttaaatattt tgatacaaca attgatcgta aacgatatac gtctacaaaa 4020
gaagttttag atgccactct tatccatcaa tccatcactg gtctttatga aacacgcatt 4080
gatttgagtc agctaggagg tgactga 4107

<210> SEQ ID NO 65
<211> LENGTH: 1368
<212> TYPE: PRT
<213> ORGANISM: Artificial Sequence
<220> FEATURE:
<223> OTHER INFORMATION: Cas9 amino acid sequence

<400> SEQUENCE: 65

Met Asp Lys Lys Tyr Ser Ile Gly Leu Asp Ile Gly Thr Asn Ser Val
1 5 10 15

Gly Trp Ala Val Ile Thr Asp Glu Tyr Lys Val Pro Ser Lys Lys Phe
20 25 30

Lys Val Leu Gly Asn Thr Asp Arg His Ser Ile Lys Lys Asn Leu Ile
35 40 45

Gly Ala Leu Leu Phe Asp Ser Gly Glu Thr Ala Glu Ala Thr Arg Leu
50 55 60

Lys Arg Thr Ala Arg Arg Arg Tyr Thr Arg Arg Lys Asn Arg Ile Cys
65 70 75 80

Tyr Leu Gln Glu Ile Phe Ser Asn Glu Met Ala Lys Val Asp Asp Ser
85 90 95

Phe Phe His Arg Leu Glu Glu Ser Phe Leu Val Glu Glu Asp Lys Lys
100 105 110

His Glu Arg His Pro Ile Phe Gly Asn Ile Val Asp Glu Val Ala Tyr
115 120 125

His Glu Lys Tyr Pro Thr Ile Tyr His Leu Arg Lys Lys Leu Val Asp
130 135 140

Ser Thr Asp Lys Ala Asp Leu Arg Leu Ile Tyr Leu Ala Leu Ala His
145 150 155 160

Met Ile Lys Phe Arg Gly His Phe Leu Ile Glu Gly Asp Leu Asn Pro
165 170 175

Asp Asn Ser Asp Val Asp Lys Leu Phe Ile Gln Leu Val Gln Thr Tyr
180 185 190

Asn Gln Leu Phe Glu Glu Asn Pro Ile Asn Ala Ser Gly Val Asp Ala
195 200 205

Lys Ala Ile Leu Ser Ala Arg Leu Ser Lys Ser Arg Arg Leu Glu Asn
210 215 220

Leu Ile Ala Gln Leu Pro Gly Glu Lys Lys Asn Gly Leu Phe Gly Asn
225 230 235 240

Leu Ile Ala Leu Ser Leu Gly Leu Thr Pro Asn Phe Lys Ser Asn Phe
245 250 255

```
Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670
```

```
Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys  Tyr Pro Lys Leu Glu  Ser Glu Phe
        995                 1000                1005

Val Tyr  Gly Asp Tyr Lys Val  Tyr Asp Val Arg Lys  Met Ile Ala
    1010                1015                1020

Lys Ser  Glu Gln Glu Ile Gly  Lys Ala Thr Ala Lys  Tyr Phe Phe
    1025                1030                1035

Tyr Ser  Asn Ile Met Asn Phe  Phe Lys Thr Glu Ile  Thr Leu Ala
    1040                1045                1050

Asn Gly  Glu Ile Arg Lys Arg  Pro Leu Ile Glu Thr  Asn Gly Glu
    1055                1060                1065

Thr Gly  Glu Ile Val Trp Asp  Lys Gly Arg Asp Phe  Ala Thr Val
    1070                1075                1080
```

```
Arg Lys  Val Leu Ser Met Pro  Gln Val Asn Ile Val  Lys Lys Thr
    1085                 1090                 1095

Glu Val  Gln Thr Gly Gly Phe  Ser Lys Glu Ser Ile  Leu Pro Lys
    1100                 1105                 1110

Arg Asn  Ser Asp Lys Leu Ile  Ala Arg Lys Lys Asp  Trp Asp Pro
    1115                 1120                 1125

Lys Lys  Tyr Gly Gly Phe Asp  Ser Pro Thr Val Ala  Tyr Ser Val
    1130                 1135                 1140

Leu Val  Val Ala Lys Val Glu  Lys Gly Lys Ser Lys  Lys Leu Lys
    1145                 1150                 1155

Ser Val  Lys Glu Leu Leu Gly  Ile Thr Ile Met Glu  Arg Ser Ser
    1160                 1165                 1170

Phe Glu  Lys Asn Pro Ile Asp  Phe Leu Glu Ala Lys  Gly Tyr Lys
    1175                 1180                 1185

Glu Val  Lys Lys Asp Leu Ile  Ile Lys Leu Pro Lys  Tyr Ser Leu
    1190                 1195                 1200

Phe Glu  Leu Glu Asn Gly Arg  Lys Arg Met Leu Ala  Ser Ala Gly
    1205                 1210                 1215

Glu Leu  Gln Lys Gly Asn Glu  Leu Ala Leu Pro Ser  Lys Tyr Val
    1220                 1225                 1230

Asn Phe  Leu Tyr Leu Ala Ser  His Tyr Glu Lys Leu  Lys Gly Ser
    1235                 1240                 1245

Pro Glu  Asp Asn Glu Gln Lys  Gln Leu Phe Val Glu  Gln His Lys
    1250                 1255                 1260

His Tyr  Leu Asp Glu Ile Ile  Glu Gln Ile Ser Glu  Phe Ser Lys
    1265                 1270                 1275

Arg Val  Ile Leu Ala Asp Ala  Asn Leu Asp Lys Val  Leu Ser Ala
    1280                 1285                 1290

Tyr Asn  Lys His Arg Asp Lys  Pro Ile Arg Glu Gln  Ala Glu Asn
    1295                 1300                 1305

Ile Ile  His Leu Phe Thr Leu  Thr Asn Leu Gly Ala  Pro Ala Ala
    1310                 1315                 1320

Phe Lys  Tyr Phe Asp Thr Thr  Ile Asp Arg Lys Arg  Tyr Thr Ser
    1325                 1330                 1335

Thr Lys  Glu Val Leu Asp Ala  Thr Leu Ile His Gln  Ser Ile Thr
    1340                 1345                 1350

Gly Leu  Tyr Glu Thr Arg Ile  Asp Leu Ser Gln Leu  Gly Gly Asp
    1355                 1360                 1365
```

<210> SEQ ID NO 66
<211> LENGTH: 22
<212> TYPE: DNA
<213> ORGANISM: Artificial Sequence
<220> FEATURE:
<223> OTHER INFORMATION: TRAC upstream primer

<400> SEQUENCE: 66
cttgtccatc actggcatct gg 22

<210> SEQ ID NO 67
<211> LENGTH: 20
<212> TYPE: DNA
<213> ORGANISM: Artificial Sequence
<220> FEATURE:
<223> OTHER INFORMATION: TRAC downstream primer

<400> SEQUENCE: 67
cgtgtcattc tctggactgc 20

<210> SEQ ID NO 68
<211> LENGTH: 22
<212> TYPE: DNA
<213> ORGANISM: Artificial Sequence
<220> FEATURE:
<223> OTHER INFORMATION: HLA-A02 upstream primer 1

<400> SEQUENCE: 68
gattccccaa ctccgcagtt tc 22

<210> SEQ ID NO 69
<211> LENGTH: 21
<212> TYPE: DNA
<213> ORGANISM: Artificial Sequence
<220> FEATURE:
<223> OTHER INFORMATION: HLA-A02 downstream primer1

<400> SEQUENCE: 69
atacctcatg gagtgagagc c 21

<210> SEQ ID NO 70
<211> LENGTH: 21
<212> TYPE: DNA
<213> ORGANISM: Artificial Sequence
<220> FEATURE:
<223> OTHER INFORMATION: HLA-A02 upstream primer 2

<400> SEQUENCE: 70
aaacggcctc tgtggggaga a 21

<210> SEQ ID NO 71
<211> LENGTH: 20
<212> TYPE: DNA
<213> ORGANISM: Artificial Sequence
<220> FEATURE:
<223> OTHER INFORMATION: HLA-A02 downstream primer2

<400> SEQUENCE: 71
gatctcggac ccggagactg 20

<210> SEQ ID NO 72
<211> LENGTH: 21
<212> TYPE: DNA
<213> ORGANISM: Artificial Sequence
<220> FEATURE:
<223> OTHER INFORMATION: HLA-A02 upstream primer 3

<400> SEQUENCE: 72
ttaggccaaa aatcccccca g 21

<210> SEQ ID NO 73
<211> LENGTH: 22
<212> TYPE: DNA
<213> ORGANISM: Artificial Sequence
<220> FEATURE:
<223> OTHER INFORMATION: HLA-A02 downstream primer3

<400> SEQUENCE: 73
ggatctggaa acccaggagg at 22

<210> SEQ ID NO 74

<211> LENGTH: 18
<212> TYPE: DNA
<213> ORGANISM: Artificial Sequence
<220> FEATURE:
<223> OTHER INFORMATION: HLA-A02 upstream primer 4

<400> SEQUENCE: 74
gccttgttct ctgcttca 18

<210> SEQ ID NO 75
<211> LENGTH: 19
<212> TYPE: DNA
<213> ORGANISM: Artificial Sequence
<220> FEATURE:
<223> OTHER INFORMATION: HLA-A02 downstream primer4

<400> SEQUENCE: 75
gtgtatctct gctcctgtc 19

<210> SEQ ID NO 76
<211> LENGTH: 20
<212> TYPE: DNA
<213> ORGANISM: Artificial Sequence
<220> FEATURE:
<223> OTHER INFORMATION: HLA-A11 upstream primer 1

<400> SEQUENCE: 76
cagagaagcc aatcagtgtc 20

<210> SEQ ID NO 77
<211> LENGTH: 20
<212> TYPE: DNA
<213> ORGANISM: Artificial Sequence
<220> FEATURE:
<223> OTHER INFORMATION: HLA-A11 downstream primer 1

<400> SEQUENCE: 77
atctcggacc cggagactgt 20

<210> SEQ ID NO 78
<211> LENGTH: 21
<212> TYPE: DNA
<213> ORGANISM: Artificial Sequence
<220> FEATURE:
<223> OTHER INFORMATION: HLA-A11 upstream primer 2

<400> SEQUENCE: 78
ggcgccttta cccggtttca t 21

<210> SEQ ID NO 79
<211> LENGTH: 22
<212> TYPE: DNA
<213> ORGANISM: Artificial Sequence
<220> FEATURE:
<223> OTHER INFORMATION: HLA-A11 downstream primer 2

<400> SEQUENCE: 79
gtgttggtcc caattgtctc cc 22

<210> SEQ ID NO 80
<211> LENGTH: 20
<212> TYPE: DNA
<213> ORGANISM: Artificial Sequence
<220> FEATURE:
<223> OTHER INFORMATION: HLA-A24 upstream primer

<400> SEQUENCE: 80
ccattgggtg tcgggtttcc 20

<210> SEQ ID NO 81
<211> LENGTH: 22
<212> TYPE: DNA
<213> ORGANISM: Artificial Sequence
<220> FEATURE:
<223> OTHER INFORMATION: HLA-A24 downstream primer

<400> SEQUENCE: 81
tctttccgtc attccgtcag ag 22

<210> SEQ ID NO 82
<211> LENGTH: 978
<212> TYPE: RNA
<213> ORGANISM: Artificial Sequence
<220> FEATURE:
<223> OTHER INFORMATION: TRAC transcribed RNA sequence

<400> SEQUENCE: 82
auauccagaa cccugacccu gccguguacc agcugagaga cucuaaaucc agugacaagu 60
cugucugccu auucaccgau uuugauucuc aaacaaaugu gucacaaagu aaggauucug 120
auguguauau cacagacaaa acugugcuag acaugagguc uauggacuuc aagagcaaca 180
gugcuguggc cuggagcaac aaaucugacu uugcaugugc aaacgccuuc aacaacagca 240
uuauuccaga agacaccuuc uuccccagcc cagaaaguuc cugugauguc aagcuggucg 300
agaaaagcuu ugaaacagau acgaaccuaa acuuucaaaa ccugucagug auuggguucc 360
gaauccuccu ccugaaagug gccggguuua aucugcucau gacgcugcgg cuguggucca 420
gcugagaucu gcaagauugu aagacagccu gugcucccuc gcuccuuccu cugcauugcc 480
ccucuucucc cucuccaaac agagggaacu cuccuacccc caaggaggug aaagcugcua 540
ccaccucugu gcccccccgg caaugccacc aacuggaucc uacccgaauu uaugauuaag 600
auugcugaag agcugccaaa cacugcugcc accccccucug uucccuuauu gcugcuuguc 660
acugccugac auucacggca gaggcaaggc ugcugcagcc uccccuggcu gugcacauuc 720
ccuccugcuc cccagagacu gccuccgcca ucccacagau gauggaucuu cagugggguuc 780 ucuugggcuc uagguccugc agaauguugu gaggggguuua uuuuuuuuua auaguguuca 840
uaaagaaaua cauaguauuc uucuucucaa gacguggggg gaaauuaucu cauuaucgag 900
gcccugcuau gcuguguauc ugggcguguu guauguccug cugccgaugc cuucauuaaa 960
augauuugga agagcaga 978

<210> SEQ ID NO 83
<211> LENGTH: 1098
<212> TYPE: RNA
<213> ORGANISM: Artificial Sequence
<220> FEATURE:
<223> OTHER INFORMATION: HLA-A02010101 transcribed RNA sequence

<400> SEQUENCE: 83
auggccguca uggcgccccg aacccucguc cugcuacucu cgggggcucu ggcccugacc 60
cagaccuggg cgggcucuca cuccaugagg uauuucuuca cauccguguc ccggcccggc 120
cgcggggagc cccgcuucau cgcagugggc uacguggacg acacgcaguu cgugcgguuc 180
gacagcgacg ccgcgagcca gaggauggag ccgcgggcgc cguggauaga gcaggagggu 240
ccggaguauu gggacgggga gacacggaaa gugaaggccc acucacagac ucaccgagug 300
gaccugggga cccugcgcgg cuacuacaac cagagcgagg ccgguucuca caccguccag 360
aggauguaug gcugcgacgu ggggucggac uggcgcuucc uccgcgggua ccaccaguac 420
gccuacgacg gcaaggauua caucgcccug aaagaggacc ugcgcucuug gaccgcggcg 480
gacauggcag cucagaccac caagcacaag ugggaggcgg cccauguggc ggagcaguug 540
agagccuacc uggagggcac gugcguggag uggcuccgca gauaccugga gaacgggaag 600
gagacgcugc agcgcacgga cgcccccaaa acgcauauga cucaccacgc ugucucugac 660
caugaagcca cccugaggug cugggcccug agcuucuacc cugcggagau cacacugacc 720
uggcagcggg auggggagga ccagacccag gacacggagc ucguggagac caggccugca 780
ggggauggaa ccuuccagaa gugggcggcu gugguggugc cuucuggaca ggagcagaga 840
uacaccugcc augugcagca ugaggguuug cccaagcccc ucacccugag augggagccg 900
ucuucccagc ccaccauccc caucgugggc aucauugcug gccugguucu cuuuggagcu 960
gugaucacug gagcuguggu cgcugcugug auguggagga ggaagagcuc agauagaaaa 1020
ggagggagcu acucucaggc ugcaagcagu gacagugccc agggcucuga ugugucucuc 1080
acagcuugua aaguguga 1098

<210> SEQ ID NO 84
<211> LENGTH: 1098
<212> TYPE: RNA
<213> ORGANISM: Artificial Sequence
<220> FEATURE:
<223> OTHER INFORMATION: HLA-A11010101 transcribed RNA sequence

<400> SEQUENCE: 84
auggccguca uggcgccccg aacccuccuc cugcuacucu cgggggcccu ggcccugacc 60
cagaccuggg cgggcuccca cuccaugagg uauuucuaca ccuccguguc ccggcccggc 120
cgcggggagc cccgcuucau cgccgugggc uacguggacg acacgcaguu cgugcgguuc 180
gacagcgacg ccgcgagcca gaggauggag ccgcgggcgc cguggauaga gcaggagggg 240
ccggaguauu gggaccagga gacacggaau gugaaggccc agucacagac ugaccgagug 300
gaccugggga cccugcgcgg cuacuacaac cagagcgagg acgguucuca caccauccag 360
auaauguaug gcugcgacgu ggggccggac gggcgcuucc uccgcgggua ccggcaggac 420
gccuacgacg gcaaggauua caucgcccug aacgaggacc ugcgcucuug gaccgcggcg 480
gacauggcag cucagaucac caagcgcaag ugggaggcgg cccaugcggc ggagcagcag 540
agagccuacc uggagggccg gugcguggag uggcuccgca gauaccugga gaacgggaag 600
gagacgcugc agcgcacgga ccccccccaag acacauauga cccaccaccc caucucugac 660
caugaggcca cccugaggug cugggcccug ggcuucuacc cugcggagau cacacugacc 720
uggcagcggg auggggagga ccagacccag gacacggagc ucguggagac caggccugca 780
ggggauggaa ccuuccagaa gugggcggcu gugguggugc cuucuggaga ggagcagaga 840
uacaccugcc augugcagca ugagggucug cccaagcccc ucacccugag augggagcug 900
ucuucccagc ccaccauccc caucgugggc aucauugcug gccugguucu ccuuggagcu 960
gugaucacug gagcuguggu cgcugccgug auguggagga ggaagagcuc agauagaaaa 1020
ggagggaguu acacucaggc ugcaagcagu gacagugccc agggcucuga ugugucucuc 1080
acagcuugua aaguguga 1098

<210> SEQ ID NO 85
<211> LENGTH: 1098
<212> TYPE: RNA
<213> ORGANISM: Artificial Sequence
<220> FEATURE:
<223> OTHER INFORMATION: HLA-A240201 transcribed RNA sequence

<400> SEQUENCE: 85
auggccguca uggcgccccg aacccucguc cugcuacucu cgggggcccu ggcccugacc 60
cagaccuggg caggcuccca cuccaugagg uauuucucca cauccguguc ccggcccggc 120
cgcggggagc cccgcuucau cgccgugggc uacguggacg acacgcaguu cgugcgguuc 180
gacagcgacg ccgcgagcca gaggauggag ccgcgggcgc cguggauaga gcaggagggg 240
ccggaguauu gggacgagga gacagggaaa gugaaggccc acucacagac ugaccgagag 300
aaccugcgga ucgcgcuccg cuacuacaac cagagcgagg ccgguucuca cacccuccag 360
augauguuug gcugcgacgu ggggucggac gggcgcuucc uccgcgggua ccaccaguac 420
gccuacgacg gcaaggauua caucgcccug aaagaggacc ugcgcucuug gaccgcggcg 480
gacauggcgg cucagaucac caagcgcaag ugggaggcgg cccauguggc ggagcagcag 540
agagccuacc uggagggcac gugcguggac gggcuccgca gauaccugga gaacgggaag 600
gagacgcugc agcgcacgga cccccccaag acacauauga cccaccaccc caucucugac 660
caugaggcca cucugagaug cugggcccug ggcuucuacc cugcggagau cacacugacc 720
uggcagcggg augggggagga ccagacccag gacacggagc uuguggagac caggccugca 780
ggggauggaa ccuuccagaa gugggcagcu gugguggguac cuucuggaga ggagcagaga 840
uacaccugcc augugcagca ugagggucug cccaagcccc ucacccugag augggagcca 900
ucuucccagc ccaccguccc caucgugggc aucauugcug gccugguucu ccuuggagcu 960
gugaucacug gagcuguggu cgcugcugug auguggagga ggaacagcuc agauagaaaa 1020
ggagggagcu acucucaggc ugcaagcagu gacagugccc agggcucuga ugugucucuc 1080
acagcuugua aaguguga 1098

<210> SEQ ID NO 86
<211> LENGTH: 1098
<212> TYPE: RNA
<213> ORGANISM: Artificial Sequence
<220> FEATURE:
<223> OTHER INFORMATION: HLA-A30010101 transcribed RNA sequence

<400> SEQUENCE: 86
auggccguca uggcgccccg aacccuccuc cugcuacucu cgggggcccu ggcccugacc 60
cagaccuggg cgggcuccca cuccaugagg uauuucucca cauccguguc ccggcccggc 120
aguggagagc cccgcuucau cgcagugggc uacguggacg acacgcaguu cgugcgguuc 180
gacagcgacg ccgcgagcca gaggauggag ccgcgggcgc cguggauaga gcaggagagg 240
ccugaguauu gggaccagga gacacggaau gugaaggccc agucacagac ugaccgagug 300 gaccuggga cccugcgcgg cuacuacaac cagagcgagg ccgguucuca caccauccag 360
auaauguaug gcugcgacgu ggggucggac gggcgcuucc uccgcgggua ugaacagcac 420
gccuacgacg gcaaggauua caucgcccug aacgaggacc ugcgcucuug gaccgcggcg 480
gacauggcgg cucagaucac ccagcgcaag ugggaggcgg cccguugggc ggagcaguug 540
agagccuacc uggagggcac gugcguggag uggcuccgca gauaccugga gaacgggaag 600
gagacgcugc agcgcacgga cccccccaag acacauauga cccaccaccc caucucugac 660
caugaggcca cccugaggug cugggcccug ggcuucuacc cugcggagau cacacugacc 720
uggcagcggg auggggagga ccagacccag gacacggagc ucguggagac caggccugca 780
ggggauggaa ccuuccagaa gugggcggcu gugguggugc cuucuggaga ggagcagaga 840
uacaccugcc augugcagca ugagggucug cccaagcccc ucacccugag augggagcug 900
ucuucccagc ccaccauccc caucgugggc aucauugcug gccugguucu ccuuggagcu 960
gugaucacug gagcuguggu cgcugccgug auguggagga ggaagagcuc agauagaaaa 1020
ggagggaguu acacucaggc ugcaagcagu gacagugccc agggcucuga ugugucucuc 1080
acagcuugua aaguguga 1098

<210> SEQ ID NO 87
<211> LENGTH: 1098
<212> TYPE: RNA
<213> ORGANISM: Artificial Sequence
<220> FEATURE:
<223> OTHER INFORMATION: HLA-A33010101 transcribed RNA sequence

<400> SEQUENCE: 87
auggccguca uggcgccccg aacccuccuc cugcuacucu ugggggcccu ggcccugacc 60
cagaccuggg cgggcuccca cuccaugagg uauuucacca cauccguguc ccggcccggc 120
cgcggggagc cccgcuucau cgccgugggc uacguggacg acacgcaguu cgugcgguuc 180
gacagcgacg ccgcgagcca gaggauggag ccgcgggcgc cguggauaga gcaggagggg 240
ccggaguauu gggaccggaa cacacggaau gugaaggccc acucacagau ugaccgagug 300
gaccugggga cccugcgcgg cuacuacaac cagagcgagg ccgguucuca caccauccag 360
augauguaug gcugcgacgu ggggucggac gggcgcuucc uccgcgggua ccagcaggac 420
gccuacgacg gcaaggauua caucgccuug aacgaggacc ugcgcucuug gaccgcggcg 480
gacauggcgg cucagaucac ccagcgcaag ugggaggcgg cccguguggc ggagcaguug 540
agagccuacc uggagggcac gugcguggag uggcuccgca gacaccugga gaacgggaag 600
gagacgcugc agcgcacgga cccccccagg acgcauauga cucaccacgc ugucucugac 660
caugaggcca cccugaggug cugggcccug agcuucuacc cugcggagau cacacugacc 720
uggcagcggg auggggagga ccagacccag gacacggagc ucguggagac caggccugca 780
ggggauggaa ccuuccagaa gugggcgucu gugguggugc cuucuggaca ggagcagaga 840
uacaccugcc augugcagca ugagggucuc cccaagcccc ucacccugag augggagccg 900
ucuucccagc ccaccauccc caucgugggc aucauugcug gccuaguucu cuuuggagcu 960
guguucgcug gagcuguggu cgcugcugug agguggagga ggaagagcuc agauagaaaa 1020
ggagggagcu acucucaggc ugcaagcagu gacagugccc agggcucuga uaugucucuc 1080
acagcuugua aaguguga 1098

<210> SEQ ID NO 88
<211> LENGTH: 1098
<212> TYPE: RNA
<213> ORGANISM: Artificial Sequence
<220> FEATURE:
<223> OTHER INFORMATION: HLA-A03010101 transcribed RNA sequence

<400> SEQUENCE: 88
auggccguca uggcgccccg aacccuccuc cugcuacucu cgggggcccu ggcccugacc 60
cagaccuggg cgggcuccca cuccaugagg uauuucuuca cauccguguc ccggcccggc 120
cgcggggagc cccgcuucau cgccgugggc uacguggacg acacgcaguu cgugcgguuc 180

```
gacagcgacg ccgcgagcca gaggauggag ccgcgggcgc cguggauaga gcaggagggg    240

ccggaguauu gggaccagga gacacggaau gugaaggccc agucacagac ugaccgagug    300

gaccugggga cccugcgcgg cuacuacaac cagagcgagg ccgguucuca caccauccag    360

auaauguaug gcugcgacgu ggggucggac gggcgcuucc uccgcgggua ccggcaggac    420

gccuacgacg gcaaggauua caucgcccug aacgaggacc ugcgcucuug gaccgcggcg    480

gacauggcgg cucagaucac caagcgcaag ugggaggcgg cccaugaggc ggagcaguug    540

agagccuacc uggauggcac gugcguggag uggcuccgca gauaccugga gaacgggaag    600

gagacgcugc agcgcacgga cccccccaag acacauauga cccaccaccc caucucugac    660

caugaggcca cccugaggug cugggcccug ggcuucuacc cugcggagau cacacugacc    720

uggcagcggg auggggagga ccagacccag gacacggagc ucguggagac caggccugca    780

ggggauggaa ccuuccagaa gugggcggcu gugguggugc cuucuggaga ggagcagaga    840

uacaccugcc augugcagca ugagggucug cccaagcccc ucacccugag augggagcug    900

ucuucccagc ccaccauccc caucgugggc aucauugcug gccugguucu ccuuggagcu    960

gugaucacug gagcuguggu cgcugccgug auguggagga ggaagagcuc agauagaaaa   1020

ggagggaguu acacucaggc ugcaagcagu gacagugccc agggcucuga ugugucccuc   1080

acagcuugua aaguguga                                                 1098
```

```
<210> SEQ ID NO 89
<211> LENGTH: 1098
<212> TYPE: RNA
<213> ORGANISM: Artificial Sequence
<220> FEATURE:
<223> OTHER INFORMATION: HLA-A01010101 transcribed RNA sequence

<400> SEQUENCE: 89
```

```
auggccguca uggcgccccg aacccuccuc cugcuacucu cggggggcccu ggcccugacc     60

cagaccuggg cgggcuccca cuccaugagg uauuucuuca cauccguguc ccggcccggc    120

cgcggggagc cccgcuucau cgccgugggc uacguggacg acacgcaguu cgugcgguuc    180

gacagcgacg ccgcgagcca gaagauggag ccgcgggcgc cguggauaga gcaggagggg    240

ccggaguauu gggaccagga gacacggaau augaaggccc acucacagac ugaccgagcg    300

aaccugggga cccugcgcgg cuacuacaac cagagcgagg acgguucuca caccauccag    360

auaauguaug gcugcgacgu ggggccggac gggcgcuucc uccgcgggua ccggcaggac    420

gccuacgacg gcaaggauua caucgcccug aacgaggacc ugcgcucuug gaccgcggcg    480

gacauggcag cucagaucac caagcgcaag ugggaggcgg uccaugcggc ggagcagcgg    540

agagucuacc uggagggccg gugcguggac gggcuccgca gauaccugga gaacgggaag    600

gagacgcugc agcgcacgga cccccccaag acacauauga cccaccaccc caucucugac    660

caugaggcca cccugaggug cugggcccug ggcuucuacc cugcggagau cacacugacc    720

uggcagcggg auggggagga ccagacccag gacacggagc ucguggagac caggccugca    780

ggggauggaa ccuuccagaa gugggcggcu gugguggugc cuucuggaga ggagcagaga    840

uacaccugcc augugcagca ugagggucug cccaagcccc ucacccugag augggagcug    900

ucuucccagc ccaccauccc caucgugggc aucauugcug gccugguucu ccuuggagcu    960

gugaucacug gagcuguggu cgcugccgug auguggagga ggaagagcuc agauagaaaa   1020
```

ggagggaguu acacucaggc ugcaagcagu gacagugccc agggcucuga ugugucucuc 1080
acagcuugua aaguguga 1098

<210> SEQ ID NO 90
<211> LENGTH: 1098
<212> TYPE: RNA
<213> ORGANISM: Artificial Sequence
<220> FEATURE:
<223> OTHER INFORMATION: HLA-A26010101 transcribed RNA sequence

<400> SEQUENCE: 90
auggccguca uggcgccccg aacccucguc cugcuacucu cgggggcccu ggcccugacc 60
cagaccuggg cgggcuccca cuccaugagg uauuucuaca ccuccguguc ccggcccggc 120
cgcggggagc cccgcuucau cgccgugggc uacguggacg acacgcaguu cgugcgguuc 180
gacagcgacg ccgcgagcca gaggauggag ccgcgggcgc cguggauaga gcaggagggg 240
ccggaguauu gggaccggaa cacacggaau gugaaggccc acucacagac ugaccgagcg 300
aaccugggga cccugcgcgg cuacuacaac cagagcgagg acgguucuca caccauccag 360
aggauguaug gcugcgacgu ggggccggac gggcgcuucc uccgcgggua ccagcaggac 420
gcuuacgacg gcaaggauua caucgcccug aacgaggacc ugcgcucuug gaccgcggcg 480
gacauggcgg cucagaucac ccagcgcaag ugggagacgg cccaugaggc ggagcagugg 540
agagccuacc uggagggccg gugcguggag uggcuccgca gauaccugga gaacgggaag 600
gagacgcugc agcgcacgga cgcccccaag acgcauauga cucaccacgc ugucucugac 660
caugaggcca cccugaggug cugggcccug agcuucuacc cugcggagau cacacugacc 720
uggcagcggg auggggagga ccagacccag gacacggagc ucguggagac caggccugca 780
ggggauggga ccuuccagaa gugggcgucu gugguggugc cuucuggaca ggagcagaga 840
uacaccugcc augugcagca ugagggucug cccaagcccc ucacccugag augggagccg 900
ucuucccagc ccaccauccc caucgugggc aucauugcug gccugguucu cuuuggagcu 960
gugaucgcug gagcuguggu cgcugcugug auguggagga ggaagagcuc agauagaaaa 1020
ggagggagcu acucucaggc ugcaagcagu gacagugccc agggcucuga uaugucucuc 1080
acagcuugua aaguguga 1098

<210> SEQ ID NO 91
<211> LENGTH: 20
<212> TYPE: RNA
<213> ORGANISM: Artificial Sequence
<220> FEATURE:
<223> OTHER INFORMATION: HLA-A11 sg21

<400> SEQUENCE: 91
ggccccuccu gcucuaucca 20

<210> SEQ ID NO 92
<211> LENGTH: 20
<212> TYPE: RNA
<213> ORGANISM: Artificial Sequence
<220> FEATURE:
<223> OTHER INFORMATION: HLA-A11 Rsg2

<400> SEQUENCE: 92
cguccugccg guacccgcgg 20

<210> SEQ ID NO 93

<211> LENGTH: 21
<212> TYPE: RNA
<213> ORGANISM: Artificial Sequence
<220> FEATURE:
<223> OTHER INFORMATION: HLA-A-homo-551

<400> SEQUENCE: 93
gcggagcagu ugagagccua c 21

<210> SEQ ID NO 94
<211> LENGTH: 21
<212> TYPE: RNA
<213> ORGANISM: Artificial Sequence
<220> FEATURE:
<223> OTHER INFORMATION: HLA-A-homo-NEG

<400> SEQUENCE: 94
gcucagauca ccaagcgcaa g 21

<210> SEQ ID NO 95
<211> LENGTH: 21
<212> TYPE: RNA
<213> ORGANISM: Artificial Sequence
<220> FEATURE:
<223> OTHER INFORMATION: TRAC-homo-375

<400> SEQUENCE: 95
gaaaguggcc ggguuuaauc u 21

<210> SEQ ID NO 96
<211> LENGTH: 21
<212> TYPE: RNA
<213> ORGANISM: Artificial Sequence
<220> FEATURE:
<223> OTHER INFORMATION: TRAC-homo-NEG

<400> SEQUENCE: 96
gaaacagaua cgaaccuaaa c 21

<210> SEQ ID NO 97
<211> LENGTH: 32
<212> TYPE: DNA
<213> ORGANISM: Artificial Sequence
<220> FEATURE:
<223> OTHER INFORMATION: Fig1-the first line

<400> SEQUENCE: 97
atccagaacc ctgaccctgc cgtgtaccag ct 32

<210> SEQ ID NO 98
<211> LENGTH: 33
<212> TYPE: DNA
<213> ORGANISM: Artificial Sequence
<220> FEATURE:
<223> OTHER INFORMATION: Fig1-the second line

<400> SEQUENCE: 98
atccagaacc ctgaccctgc cgtgtaacca gct 33

<210> SEQ ID NO 99
<211> LENGTH: 52
<212> TYPE: DNA
<213> ORGANISM: Artificial Sequence
<220> FEATURE:
<223> OTHER INFORMATION: Fig2-the first line, as well as the third line

<400> SEQUENCE: 99
tccagaaccc tgaccctgcc gtgtaccagc tgagagactc taaatccagt ga 52

<210> SEQ ID NO 100
<211> LENGTH: 52
<212> TYPE: DNA
<213> ORGANISM: Artificial Sequence
<220> FEATURE:
<223> OTHER INFORMATION: Fig2-the second line

<400> SEQUENCE: 100
aggtcttggg actgggacgg cacatggtcg actctctgag atttaggtca ct 52

<210> SEQ ID NO 101
<211> LENGTH: 53
<212> TYPE: DNA
<213> ORGANISM: Artificial Sequence
<220> FEATURE:
<223> OTHER INFORMATION: TA-1

<400> SEQUENCE: 101
tccagaaccc tgaccctgcc gtctaaccag ctgagagact ctaaatccag tga 53

<210> SEQ ID NO 102
<211> LENGTH: 53
<212> TYPE: DNA
<213> ORGANISM: Artificial Sequence
<220> FEATURE:
<223> OTHER INFORMATION: TA-2,4,6,8,10

<400> SEQUENCE: 102
tccagaaccc tgaccctgcc gtgtaaccag ctgagagact ctaaatccag tga 53

<210> SEQ ID NO 103
<211> LENGTH: 46
<212> TYPE: DNA
<213> ORGANISM: Artificial Sequence
<220> FEATURE:
<223> OTHER INFORMATION: TA-3

<400> SEQUENCE: 103
tccagaaccc tgaccctggc cagctgagag actctaaatc cagtga 46

<210> SEQ ID NO 104
<211> LENGTH: 47
<212> TYPE: DNA
<213> ORGANISM: Artificial Sequence
<220> FEATURE:
<223> OTHER INFORMATION: TA-5

<400> SEQUENCE: 104
tccagaaccc tgaccctgcc gtgtcactct ctgacagagt ctaattc 47

<210> SEQ ID NO 105
<211> LENGTH: 50
<212> TYPE: DNA
<213> ORGANISM: Artificial Sequence
<220> FEATURE:
<223> OTHER INFORMATION: TA-7

<400> SEQUENCE: 105
tccagaaccc tgaccctgcc gtgtcagctg agagactcta aatccagtga 50

<210> SEQ ID NO 106

<211> LENGTH: 49
<212> TYPE: DNA
<213> ORGANISM: Artificial Sequence
<220> FEATURE:
<223> OTHER INFORMATION: TA-9

<400> SEQUENCE: 106
tccagaaccc tgaccctgcc gtgtagctga gagactctaa atccagtga 49

<210> SEQ ID NO 107
<211> LENGTH: 35
<212> TYPE: DNA
<213> ORGANISM: Artificial Sequence
<220> FEATURE:
<223> OTHER INFORMATION: TA-11

<400> SEQUENCE: 107
tccagaaccc tgaccctgcc gtgtaaatcc agtga 35

<210> SEQ ID NO 108
<211> LENGTH: 45
<212> TYPE: DNA
<213> ORGANISM: Artificial Sequence
<220> FEATURE:
<223> OTHER INFORMATION: TA-12

<400> SEQUENCE: 108
tccagaaccc tgaccctgcc agctgagaga ctctaaatcc agtga 45

<210> SEQ ID NO 109
<211> LENGTH: 63
<212> TYPE: DNA
<213> ORGANISM: Artificial Sequence
<220> FEATURE:
<223> OTHER INFORMATION: Fig4 1

<400> SEQUENCE: 109
ggggtcggac tggcgcttcc tccgcgggta ccaccagtac gcctacgacg gcaaggatta 60
cat 63

<210> SEQ ID NO 110
<211> LENGTH: 61
<212> TYPE: DNA
<213> ORGANISM: Artificial Sequence
<220> FEATURE:
<223> OTHER INFORMATION: Fig4 2
<220> FEATURE:
<221> NAME/KEY: misc_feature
<222> LOCATION: (4)..(4)
<223> OTHER INFORMATION: n = a, c, g or t
<220> FEATURE:
<221> NAME/KEY: misc_feature
<222> LOCATION: (9)..(9)
<223> OTHER INFORMATION: n = a, c, g or t
<220> FEATURE:
<221> NAME/KEY: misc_feature
<222> LOCATION: (10)..(10)
<223> OTHER INFORMATION: n = a, c, g or t
<220> FEATURE:
<221> NAME/KEY: misc_feature
<222> LOCATION: (32)..(32)
<223> OTHER INFORMATION: n = a, c, g or t
<220> FEATURE:
<221> NAME/KEY: misc_feature
<222> LOCATION: (34)..(34)
<223> OTHER INFORMATION: n = a, c, g or t
<220> FEATURE:
<221> NAME/KEY: misc_feature
<222> LOCATION: (35)..(35)
<223> OTHER INFORMATION: n = a, c, g or t

<400> SEQUENCE: 110
ggtntgggnn gggctttttc tccgggtacc ancnntacgc ctacgacggc aaggattaca 60
t 61

<210> SEQ ID NO 111
<211> LENGTH: 56
<212> TYPE: DNA
<213> ORGANISM: Artificial Sequence
<220> FEATURE:
<223> OTHER INFORMATION: Fig 5 1

<400> SEQUENCE: 111
atatgactca ccacgctgtc tctgaccatg aagccaccct gaggtgctgg gccctg 56

<210> SEQ ID NO 112
<211> LENGTH: 55
<212> TYPE: DNA
<213> ORGANISM: Artificial Sequence
<220> FEATURE:
<223> OTHER INFORMATION: Fig 5 2

<400> SEQUENCE: 112
atatgactca ccacgctgtc tctgaccatg aagccacctg aggtgctggg ccctg 55

<210> SEQ ID NO 113
<211> LENGTH: 56
<212> TYPE: DNA
<213> ORGANISM: Artificial Sequence
<220> FEATURE:
<223> OTHER INFORMATION: Fig 6 1

<400> SEQUENCE: 113
acgccgcgag ccagaggatg gagccgcggg cgccgtggat agagcaggag gggccg 56

<210> SEQ ID NO 114
<211> LENGTH: 56
<212> TYPE: DNA
<213> ORGANISM: Artificial Sequence
<220> FEATURE:
<223> OTHER INFORMATION: Fig 6 2
<220> FEATURE:
<221> NAME/KEY: misc_feature
<222> LOCATION: (3)..(3)
<223> OTHER INFORMATION: n = a, c, g or t
<220> FEATURE:
<221> NAME/KEY: misc_feature
<222> LOCATION: (6)..(6)
<223> OTHER INFORMATION: n = a, c, g or t
<220> FEATURE:
<221> NAME/KEY: misc_feature
<222> LOCATION: (10)..(10)
<223> OTHER INFORMATION: n = a, c, g or t
<220> FEATURE:
<221> NAME/KEY: misc_feature
<222> LOCATION: (19)..(19)
<223> OTHER INFORMATION: n = a, c, g or t

<400> SEQUENCE: 114
acnccncgan ccagaggang gagccgcggg ccccgtggat agagcaggag gggccg 56

<210> SEQ ID NO 115
<211> LENGTH: 52
<212> TYPE: DNA
<213> ORGANISM: Artificial Sequence
<220> FEATURE:
<223> OTHER INFORMATION: Fig 7 1

-continued

```
<400> SEQUENCE: 115

gggccggacg ggcgcttcct ccgcgggtac cggcaggacg cctacgacgg ca            52


<210> SEQ ID NO 116
<211> LENGTH: 52
<212> TYPE: DNA
<213> ORGANISM: Artificial Sequence
<220> FEATURE:
<223> OTHER INFORMATION: Fig 7 2

<400> SEQUENCE: 116

gggccggacg ggcgcttcct ccgggggtac caccgggacc cttacaacgg ca            52


<210> SEQ ID NO 117
<211> LENGTH: 36
<212> TYPE: DNA
<213> ORGANISM: Artificial Sequence
<220> FEATURE:
<223> OTHER INFORMATION: Fig 8 1

<400> SEQUENCE: 117

ctctgaccat gaagccaccc tgaggtgctg ggccct                              36


<210> SEQ ID NO 118
<211> LENGTH: 19
<212> TYPE: DNA
<213> ORGANISM: Artificial Sequence
<220> FEATURE:
<223> OTHER INFORMATION: Fig 8 3

<400> SEQUENCE: 118

ccctgaggtg ctgggccct                                                 19


<210> SEQ ID NO 119
<211> LENGTH: 40
<212> TYPE: DNA
<213> ORGANISM: Artificial Sequence
<220> FEATURE:
<223> OTHER INFORMATION: Fig 8 4

<400> SEQUENCE: 119

accctgccgt gtaccagctg agagactcta aatccagtga                          40


<210> SEQ ID NO 120
<211> LENGTH: 41
<212> TYPE: DNA
<213> ORGANISM: Artificial Sequence
<220> FEATURE:
<223> OTHER INFORMATION: Fig 8 6

<400> SEQUENCE: 120

accctgccgt gtaaccagct gagagactct aaatccagtg a                        41
```